US 9,018,397 B2

(12) United States Patent
Hao et al.

(10) Patent No.: US 9,018,397 B2
(45) Date of Patent: *Apr. 28, 2015

(54) PYRROLOPYRROLE DERIVATIVES, THEIR MANUFACTURE AND USE

(71) Applicant: BASF SE, Ludwigshafen (DE)

(72) Inventors: Zhimin Hao, Allschwil (CH); Beat Schmidhalter, Bubendorf (CH); Jean-Luc Budry, Courroux (CH); Margherita Fontana, Thalwil (CH); Matheiu G. R. Turbiez, Rixheim (FR); Frank Bienewald, Hagenheim (FR); Mathias Duggeli, Sissach (CH); Oliver Frederic Aebischer, Dudingen (CH); Pascal Hayoz, Hofstetten (CH); Marta Fondrodona Turon, Blanes (ES)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/776,884

(22) Filed: Feb. 26, 2013

(65) Prior Publication Data

US 2013/0172575 A1 Jul. 4, 2013

Related U.S. Application Data

(62) Division of application No. 12/680,904, filed as application No. PCT/EP2008/062586 on Sep. 22, 2008, now Pat. No. 8,404,864.

(30) Foreign Application Priority Data

Oct. 9, 2007 (EP) ..................... 07118071

(51) Int. Cl.
*C07D 487/02* (2006.01)
*H01L 51/00* (2006.01)
*C07D 487/04* (2006.01)
*C09B 57/00* (2006.01)

(52) U.S. Cl.
CPC .......... *H01L 51/0071* (2013.01); *C07D 487/04* (2013.01); *H01L 51/0053* (2013.01); *H01L 51/0058* (2013.01); *H01L 51/0068* (2013.01); *C09B 57/004* (2013.01); *H01L 51/0095* (2013.01); *Y02E 10/549* (2013.01)

(58) Field of Classification Search
CPC ..................................................... C07D 487/02
USPC .............................................. 548/452, 453
See application file for complete search history.

(56) References Cited

U.S. PATENT DOCUMENTS

| | | | |
|---|---|---|---|
| 5,484,943 A | 1/1996 | Zambounis et al. | |
| 5,527,922 A | 6/1996 | Zambounis et al. | |
| 6,451,459 B1 | 9/2002 | Tieke et al. | |
| 6,603,020 B1 | 8/2003 | Moretti et al. | |
| 7,541,424 B2 | 6/2009 | Jeong et al. | |
| 7,939,818 B2 | 5/2011 | Heim et al. | |
| 8,008,507 B2 | 8/2011 | Yamamoto et al. | |
| 8,404,864 B2* | 3/2013 | Hao et al. ..... | 548/453 |
| 8,629,238 B2* | 1/2014 | Dueggeli et al. ..... | 528/377 |
| 2007/0228359 A1 | 10/2007 | Heim et al. | |
| 2009/0065766 A1 | 3/2009 | Li | |
| 2009/0065878 A1 | 3/2009 | Li | |

FOREIGN PATENT DOCUMENTS

| | | |
|---|---|---|
| JP | 2006117591 A | 5/2006 |
| JP | 2006117672 A | 5/2006 |
| JP | 2007266285 A | 10/2007 |
| WO | 2004/090046 A | 10/2004 |

OTHER PUBLICATIONS

English language abstract of JP 2006/117591.
English language abstract of JP 2007/266285 Oct. 11, 2007.

* cited by examiner

*Primary Examiner* — Golam M M Shameem
(74) *Attorney, Agent, or Firm* — Shruti Costales

(57) ABSTRACT

The present invention relates to compounds of the formula I $$R^4-[Ar^6]_f-[Ar^5]_e-[Ar^4]_d \cdots \cdots [Ar^1]_a-[Ar^2]_b-[Ar^3]_c-R^3 \quad (I)$$

wherein the substituents are as defined in claim 1, and their use as organic semiconductor in organic devices, like diodes, organic field effect transistors and/or a solar cells.

The compounds of the formula I have excellent solubility in organic solvents. High efficiency of energy conversion, excellent field-effect mobility, good on/off current ratios and/or excellent stability can be observed, when said compounds are used in semiconductor devices or organic photovoltaic (PV) devices (solar cells).

7 Claims, No Drawings

PYRROLOPYRROLE DERIVATIVES, THEIR MANUFACTURE AND USE

The present invention relates to 1,4-diketopyrrolo[3,4-c]pyrrole (DPP) derivatives of the below formula I, wherein the substituents are as defined herein below, to their manufacture; to their use as organic semiconductors, e.g. in semiconductor devices, especially a sensor, a diode, a photodiode, an organic field effect transistor, a transistor for flexible displays, and/or a solar cell (photovoltaic cell); to such semiconductor devices comprising diketopyrrolopyrrol derivatives of the formula I as a semiconducting effective means, and to devices containing said semiconductor devices.

JP 2006117591-A to Toyo Ink Manufacturing Co. discloses diketopyrrolopyrrol derivatives for use in organic electroluminescent elements, like flat panel displays and liquid crystal displays, but not for use as organic semiconductors.

WO 2004/090046 A1 to Ciba discloses fluorescent diketopyrrolopyrrol (DPP) derivatives, mainly for use in inks, toners, colorants, pigmented plastics, color changing media, solid dye lasers and electroluminescent devices. Said DPP derivatives have a smaller or shorter side chain on both sides of the diketopyrrolopyrrol moiety than the diketopyrrolopyrrol derivatives claimed per se in the present specification. In addition, specifically disclosed, i.e. individualized, compounds include only those derivatives wherein the DPP nitrogen atoms are substituted by alkyl groups having no more than 5 carbon atoms. As has been found by the present invention, for the overall efficiency of photovoltaic cells the number of carbon atoms in each of the alkyl substituents on the DPP nitrogen atoms is of major importance and should be at least 7, preferably at least 10.

It has surprisingly been found that certain monomeric diketopyrrolopyrrol derivatives, especially those having longer side chains, can be used as organic semiconductors. Said derivatives have excellent solubility in non-halogenated organic solvents (allowing easy handling). They can be synthesized easier than polymers (allowing cost savings), and they are easy to purify (allowing very pure products to be obtained at low cost).

For semiconducting devices, like solar cells, the power conversion efficiency (PCE), i.e. the the percentage of power converted from absorbed light to electrical energy, is decisive. While silicon based solar cells reach already a PCE of up to 20%, the PCE of solar cells based on organic semiconductors is still much lower, i.e. in the range of 5% for polymeric semiconductors. For monomeric, i.e. small molecule based semiconductors the PCE, as reported before the priority date of the present invention, is even lower than for polymeric semiconductors. Solution processed solar cells so far were reaching a PCE just up to about 1.3%.

Despite the lower PCE attained thus far, small molecules potentially offer several advantages over polymer and silicon based materials. With respect to silicon based materials said advantages include lower cost fabrication by solution processing, lightweight and compatibility with flexible substrates. With respect to polymeric materials small molecules do not suffer from batch to batch variations, broad molecular weight distributions, end group contamination, and difficult purification methods. Furthermore, small molecules may display higher hole and electron mobilities than their polymeric analogues, presumably as a result of better molecular ordering.

The task of the present invention was the identification of small molecules with improved PCE, high field effect mobility (charge carrier mobility), high on/off current ratio, and low threshold voltage. A high on/off current ratio is especially useful for an organic field effect transistor (OFET).

According to the present invention it has been found that certain small molecules of the diketopyrrolopyrrol class surprisingly exhibit extremely high PCEs in solar cells. Some compounds exhibit PCEs exceeding 4%! Such values have not been reported for any small molecule before! It should be kept in mind that these efficiencies have not even been optimized. Optimisation may be effected in various ways, e.g. by variation of the donor-acceptor ratio, e.g. to 70:30 by weight, or by coating the anode with a very thin (5 to 10 nanometers thick) and smooth layer of nickel oxide.

The invention relates especially to diketopyrrolopyrrol derivatives of the formula I

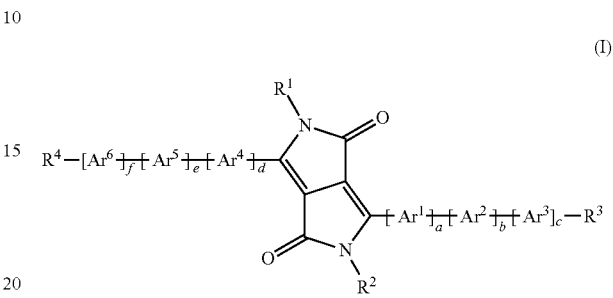

wherein $R^1$ and $R^2$ are independently of each other an aliphatic, cycloaliphatic, cycloaliphatic-aliphatic, aromatic, aromatic-aliphatic, heteroaromatic or heteroaromatic-aliphatic group having up to 49 carbon atoms, a and d independently of each other are 0, 1, 2 or 3, $Ar^1$ and $Ar^4$ are independently of each other a bivalent group of the formula II or IV

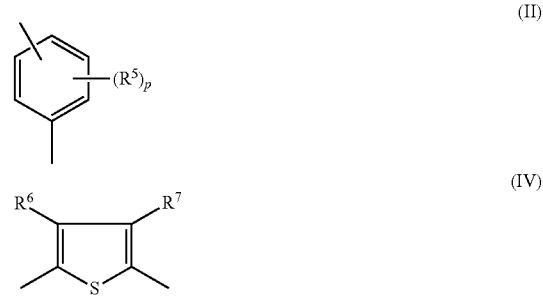

wherein $R^6$ and $R^7$ are as defined below, p represents 0, 1, or 2, $R^5$ is an aliphatic hydrocarbon group having up to 25 carbon atoms, or two vicinal groups $R^5$ together represent alkylene or alkenylene having up to 7 carbon atoms, it being possible that two groups $R^5$ present in the group of formula II differ from each other, b, c, e, and f independently of each other represent 1, 2 or 3, $Ar^2$, $Ar^3$, $Ar^5$, and $Ar^6$ are independently of each other a bivalent group of one of the formulae IV to X and L,

-continued

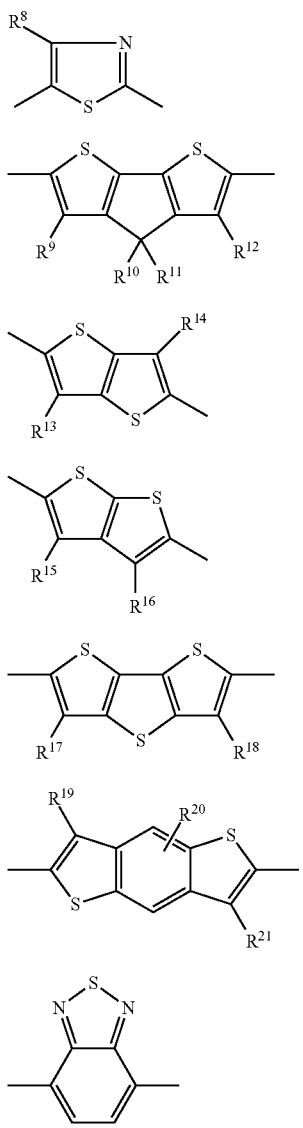

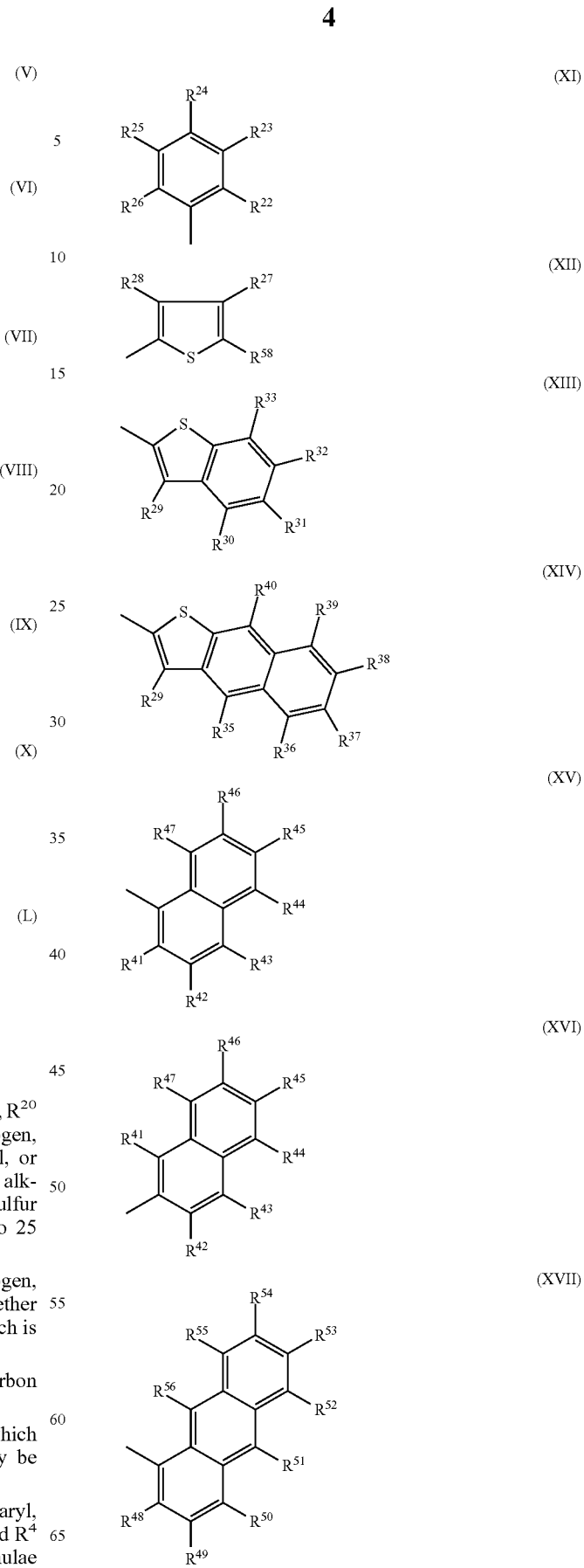

wherein $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ are independently of each other hydrogen, $C_1$-$C_{25}$alkyl, $C_1$-$C_{18}$alkoxy, $C_6$-$C_{24}$aryl, $C_7$-$C_{25}$aralkyl, or heteroaryl, or $R^6$ and $R^7$ together represent alkylene or alkenylene which may be both bonded via oxygen and/or sulfur to the thienyl residue and which may both have up to 25 carbon atoms, $R^{10}$ and $R^{11}$ are independently of each other hydrogen, $C_1$-$C_{18}$alkyl, $C_6$-$C_{24}$aryl, heteroaryl, or $R^{10}$ and $R^{11}$ together represent oxo or form a five or six membered ring, which is unsubstituted or substituted by a) an aliphatic hydrocarbon group having up to 18 carbon atoms, b) $C_1$-$C_{18}$alkoxy or $C_2$-$C_{18}$alkylenedioxy in both of which carbon atoms which are not adjacent to oxygen may be replaced by oxygen, or c) $C_6$-$C_{24}$aryl, $C_7$-$C_{25}$aralkyl, heteroaryl, $C_3$-$C_{12}$cycloalkyl or $C_4$-$C_{12}$cycloalkyl-alkyl, and $R^3$ and $R^4$ are independently of each other a group of one of the formulae XI to XIX,

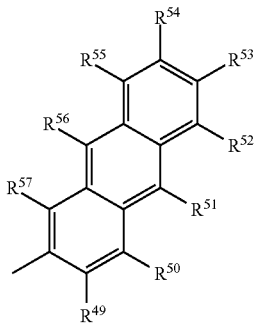

(XVIII)

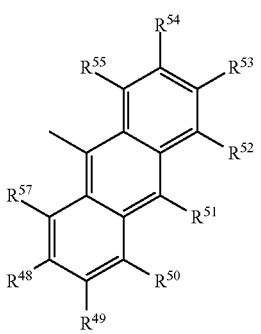

(XIX)

wherein $R^{22}$ to $R^{26}$ and $R^{29}$ to $R^{58}$ represent independently of each other hydrogen, an aliphatic hydrocarbon group having up to 25 carbon atoms, alkoxy or alkenyloxy having up to 18 carbon atoms, halogen, a cycloaliphatic, cycloaliphatic-aliphatic, aromatic, aromatic-aliphatic, heteroaromatic or heteroaromatic-aliphatic group having up to 25 carbon atoms, or a group of the formula (III)

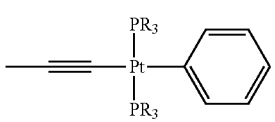

(III)

wherein R represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein R represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms.

The general terms used above have the following meanings:

An aliphatic group having up to 49 carbon atoms, as represented e.g. by the substituents $R^1$ and $R^2$, is an unsubstituted or substituted aliphatic hydrocarbon group having up to 49, e.g. up to 25 carbon atoms wherein the free valency extends from a carbon atom. Preferably, aliphatic groups as represented by the substituents $R^1$ and $R^2$ have at least 7, more preferably at least 8, even more preferably at least 10, and most preferably at least 14 carbon atoms. An aliphatic hydrocarbon group having up to 49, e.g. up to 25 carbon atoms is a linear or branched alkyl, alkenyl or alkynyl (also spelled alkinyl) group having up to 49, e.g. up to 25 carbon atoms. Preferred are aliphatic hydrocarbon groups, like especially alkyl groups, having 7-49, especially 8-49, e.g. 7-25, especially 8-25, preferably 14-25 carbon atoms. An example of a preferred alkyl group, as represented by the substituents $R^1$ and $R^2$, is 2-decyl-tetradecyl.

Examples for $C_1$-$C_{25}$alkyl groups are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 3,7-dimethyl-octyl, 1,1,3,3-tetramethylbutyl, 2-ethylhexyl, 2-n-butyl-hexyl, n-nonyl, decyl, 2-hexyl-decyl, undecyl, dodecyl, tridecyl, tetradecyl, 2-decyl-tetradecyl, pentadecyl, hexadecyl, heptadecyl, octadecyl, eicosyl, heneicosyl, docosyl, tetracosyl and pentacosyl, of which 2-decyl-tetradecyl is especially preferred as a meaning of $R^1$ and $R^2$.

Examples for $C_2$-$C_{25}$alkenyl groups are vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

Examples for $C_{2-25}$alkynyl groups are ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic group having up to 49, e.g. up to 25 carbon atoms, as represented e.g. by the substituents $R^1$ and $R^2$, is an unsubstituted or substituted cycloaliphatic hydrocarbon group having up to 49, e.g. up to 25 carbon atoms wherein the free valency extends from a ring carbon atom.

A cycloaliphatic hydrocarbon group is a cycloalkyl or cycloalkenyl group which may be substituted by one or more aliphatic and/or cycloaliphatic hydrocarbon groups.

A cycloalkyl group has at least 3, preferably at least 5 carbon atoms and is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted by one or more aliphatic and/or cycloaliphatic hydrocarbon groups and/or condensed with phenyl groups as defined herein and/or condensed with phenyl groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

For example, a cycloalkyl or cycloalkenyl group, in particular a cyclohexyl group, can be condensed one or two times with phenyl which can be substituted one to three times with $C_1$-$C_4$-alkyl. Examples of such condensed cyclohexyl groups are groups of the formulae XX to XXIV:

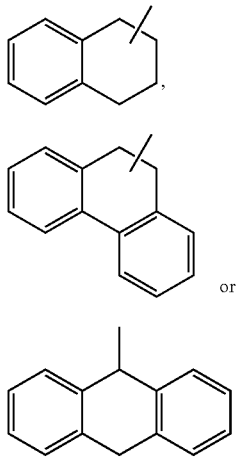

in particular

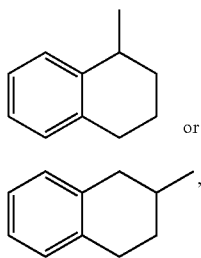

which can be substituted in the phenyl moieties one to three times with $C_1$-$C_4$-alkyl.

Preferred substituents of a substituted cycloaliphatic hydrocarbon group are e.g. $C_1$-$C_8$alkoxy or $C_1$-$C_8$alkylthio groups.

Preferably, a and d, independently of each other, are 0, 1 or 2. Also preferably a and d have the same meaning.

An aliphatic hydrocarbon group having up to 25 carbon atoms $R^5$ is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

A bivalent group of the formula II wherein two vicinal groups $R^5$ together represent alkylene or alkenylene having up to 7 carbon atoms, it being possible that two groups $R^5$ present in the group of formula II differ from each other, is for example a group of the formula

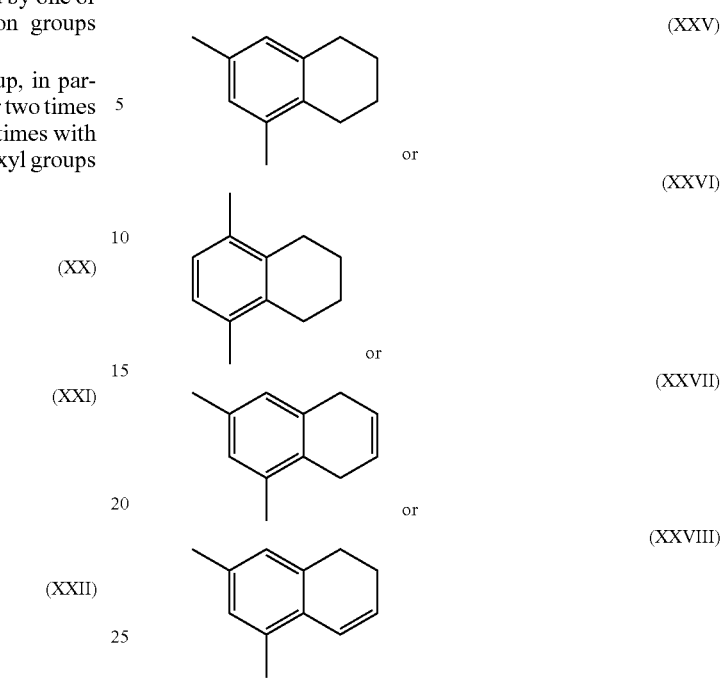

$C_1$-$C_{25}$alkyl as represented by $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ has the meanings given above.

$C_1$-$C_{18}$alkoxy, as represented e.g. by $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ to $R^{26}$, is e.g. methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy, 2-ethylhexoxy, n-nonoxy, decoxy, undecoxy, dodecoxy, tridecoxy, tetradecoxy, pentadecoxy, hexadecoxy, heptadecoxy, and octadecoxy, preferably $C_1$-$C_4$alkoxy.

The term "alkylthio group" means the same groups as the alkoxy groups, except that the oxygen atom of ether linkage is replaced by a sulfur atom.

An aromatic group as represented e.g. by $R^1$ and $R^2$ is preferably $C_6$-$C_{24}$aryl.

$C_6$-$C_{24}$aryl, as represented e.g. by $R^1$, $R^2$, $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$, is e.g. substituted or preferably unsubstituted phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 3- or 4-biphenyl, 9-phenanthryl, 2- or 9-fluorenyl, 3- or 4-biphenyl, which all may be unsubstituted or substituted, e.g. by alkyl or alkoxy.

An aromatic-aliphatic group as represented e.g. by $R^1$ and $R^2$ is an aliphatic group which is substituted by an aromatic group, wherein the terms "aromatic" and "aliphatic" are as defined herein, e.g. an aralkyl group, like 3-phenyl-propyl.

$C_7$-$C_{25}$aralkyl, as represented e.g. by $R^6$, $R^7$, $R^8$, $R^9$, $R^{12}$, $R^{13}$, $R^{15}$, $R^{16}$, $R^{17}$, $R^{18}$, $R^{19}$, $R^{20}$, $R^{21}$, $R^{27}$, or $R^{28}$ is e.g. phenyl-alkyl, like benzyl, 2-benzyl-2-propyl, β-phenyl-ethyl, α,α-dimethylbenzyl, 3-phenyl-propyl, ω-phenyl-butyl, ω,ω-dimethyl-ω-phenyl-butyl, ω-phenyl-dodecyl, ω-phenyl-octadecyl, ω-phenyl-eicosyl, and ω-phenyl-docosyl, wherein the phenyl moiety may be unsubstituted or substituted, e.g. by alkyl, alkoxy or halogen. A preferred meaning for $C_7$-$C_{25}$aralkyl, as represented by $R^6$, $R^7$, $R^{27}$, or $R^{28}$ is e.g. 3-phenyl-propyl.

A heteroaromatic group having up to 49, preferably up to 25 carbon atoms as represented e.g. by $R^1$ and $R^2$ is a heteroaryl group as defined below, but not having more than 49, preferably not more than 25 carbon atoms.

Heteroaryl, as represented e.g. by $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$, is e.g. $C_2$-$C_{26}$heteroaryl, i.e. e.g. a ring with five to seven ring atoms or a condensed ring system, wherein nitrogen, oxygen or sulfur are the possible hetero atoms, and is typically an unsaturated heterocyclic group with five to 30 atoms (including both carbon and hetero atoms) having at least six conjugated π-electrons, such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted, e.g. by alkyl.

A heteroaromatic-aliphatic group having up to 49, preferably up to 25 carbon atoms as represented e.g. by $R^1$ and $R^2$ is an aliphatic group substituted by an heteroaromatic group wherein the terms "aliphatic" and "heteroaromatic" are as defined herein except for the total number of carbon atoms which must not exceed 49, preferably 25, and wherein the free valency extends from the aliphatic moiety, e.g. heteroarylmethyl.

A bivalent group of the formula IV wherein $R^6$ and $R^7$ together represent alkylene or alkenylene which may be both bonded via oxygen and/or sulfur to the thienyl residue and which may both have up to 25 carbon atoms, is e.g. a group of the formula XXIX or XXX

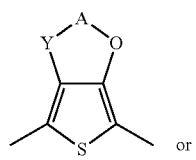

(XXIX)

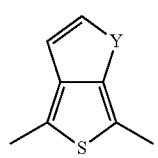

(XXX)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—CH$_2$—CH$_2$—O— or —O—CH$_2$—CH$_2$—CH$_2$—O—.

A bivalent group of the formula VI wherein $R^{10}$ and $R^{11}$ together represent oxo is a group of the formula (XXXI).

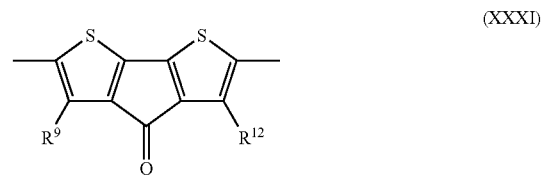

(XXXI)

$C_1$-$C_{18}$alkoxy in which carbon atoms which are not adjacent to oxygen may be replaced by oxygen is e.g. a group of one of the formulae —O—CH$_2$—O—CH$_2$—CH$_2$—O—CH$_3$, —O—(CH$_2$)$_2$OCH$_3$, —O—(CH$_2$CH$_2$O)$_2$CH$_2$CH$_3$, —O—CH$_2$—O—CH$_3$, —O—CH$_2$CH$_2$—O—CH$_2$CH$_3$, —O—CH$_2$CH$_2$CH$_2$—O—CH(CH$_3$)$_2$, —O—[CH$_2$CH$_2$O]$_n$—CH$_3$ wherein n=1-10, —O—CH$_2$—CH(CH$_3$)—O—CH$_2$—CH$_2$CH$_3$ and —O—CH$_2$—CH(CH$_3$)—O—CH$_2$—CH$_3$.

$C_2$-$C_{18}$alkylenedioxy in which carbon atoms which are not adjacent to oxygen may be replaced by oxygen is e.g. a group of the formula —O—CH$_2$—O—CH$_2$—CH$_2$—O—.

An aliphatic, cycloaliphatic, cycloaliphatic-aliphatic, aromatic, aromatic-aliphatic, heteroaromatic or heteroaromatic-aliphatic group having up to 25 carbon atoms as substituent $R^{22}$ to $R^{26}$ of a group of the formula XI has the meanings defined above. A preferred group of the formula XI is the 4-biphenyl group, which may be unsubstituted or substituted within the scope of the above terms.

An example for alkenyloxy is e.g. 3-butenyloxy.

Halogen is fluoro, chloro, bromo or iodo.

A group of the formula XI wherein two groups $R^{22}$ to $R^{26}$ which are in the neighborhood of each other, together represent alkylene or alkenylene having up to 8 carbon atoms, thereby forming a ring, is e.g. a group of the formula XXXII or XXXIII

(XXXII)

(XXXIII)

wherein in the group of the formula XXXII $R^{23}$ and $R^{24}$ together represent 1,4-butylene and wherein in the group of the formula XXXIII $R^{23}$ and $R^{24}$ together represent 1,4-but-2-en-ylene.

A group of the formula XII, wherein $R^{27}$ and $R^{28}$ together represent alkylene or alkenylene which may be both bonded via oxygen and/or sulfur to the thienyl residue and which may both have up to 25 carbon atoms, is e.g. a group of the formula XXXIV or XXXV

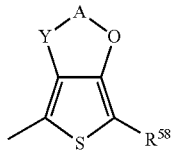
(XXXIV)

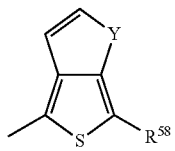
(XXXV)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—CH$_2$—CH$_2$—O— or —O—CH$_2$—CH$_2$—CH$_2$—O—.

Preferred are compounds of the formula I wherein R$^1$ and R$^2$ are independently of each other an aliphatic, cycloaliphatic, cycloaliphatic-aliphatic, aromatic, aromatic-aliphatic, heteroaromatic or heteroaromatic-aliphatic group having up to 25 carbon atoms, R$^3$ and R$^4$ are independently of each other a group of one of the formulae XI to XIX,

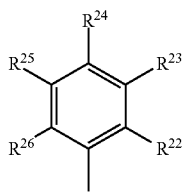
(XI)

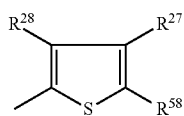
(XII)

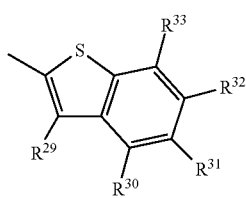
(XIII)

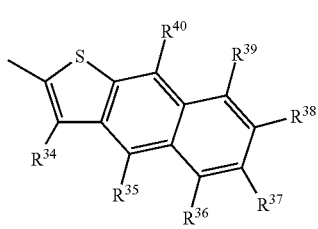
(XIV)

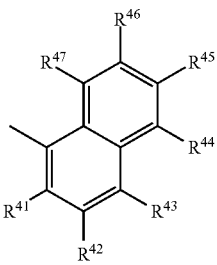
(XV)

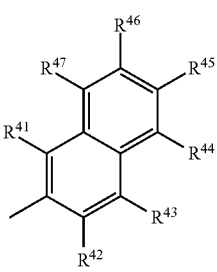
(XVI)

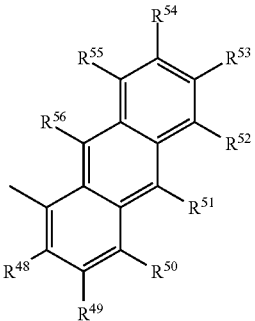
(XVII)

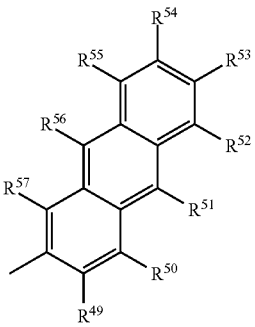
(XVIII)

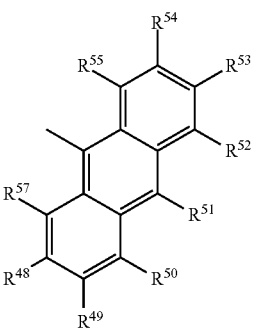
(XIX)

wherein R$^{22}$ to R$^{26}$ and R$^{29}$ to R$^{58}$ represent independently of each other hydrogen, an aliphatic hydrocarbon group having up to 25 carbon atoms, or a group of the formula (III)

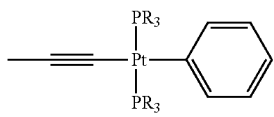

(III)

wherein R represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein R represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms, and the remaining substituents have the meanings given above.

Especially preferred are compounds of the formula I wherein $R^1$ and $R^2$ are independently of each other an aliphatic, cycloaliphatic or cycloaliphatic-aliphatic hydrocarbon group having up to 25 carbon atoms, a and d represent 0, b, c, e, and f represent 1, $Ar^2$, $Ar^3$, $Ar^5$, and $Ar^6$ are independently of each other a bivalent group of the formula IV,

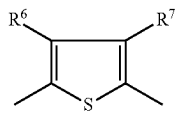

(IV)

wherein $R^6$ and $R^7$ are independently of each other hydrogen or $C_1$-$C_{25}$alkyl, and $R^3$ and $R^4$ are independently of each other a group of the formula

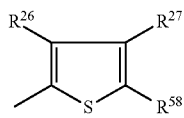

(XII)

wherein $R^{58}$ represents hydrogen or an aliphatic hydrocarbon group having up to 25 carbon atoms, and $R^{27}$ and $R^{28}$ are independently of each other hydrogen or $C_1$-$C_{25}$alkyl.

More especially preferred are compounds of the formula I wherein $R^1$ and $R^2$ are independently of each other an aliphatic, cycloaliphatic or cycloaliphatic-aliphatic hydrocarbon group having up to 25 carbon atoms, a and d represent 0, b, c, e, and f represent 1, $Ar^2$ and $Ar^5$ are independently of each other a bivalent group of the formula IV,

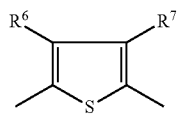

(IV)

wherein one of $R^6$ and $R^7$ represents $C_1$-$C_{25}$alkyl while the other of $R^6$ and $R^7$ represents hydrogen or $C_1$-$C_{25}$alkyl, $Ar^3$ and $Ar^6$ are a bivalent group of the formula IV, wherein each of $R^6$ and $R^7$ represents hydrogen, and $R^3$ and $R^4$ are independently of each other a group of the formula

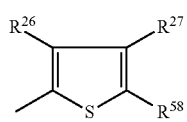

(XII)

wherein $R^{58}$ represents hydrogen or an aliphatic hydrocarbon group having up to 25 carbon atoms, and one of $R^{27}$ and $R^{28}$ represents $C_1$-$C_{25}$alkyl while the other of $R^{27}$ and $R^{28}$ represents hydrogen or $C_1$-$C_{25}$alkyl.

Very preferred are compounds of the formula I wherein $R^1$ and $R^2$ are independently of each other an alkyl group having up to 49 carbon atoms, a and d are independently of each other 0, 1 or 2, $Ar^1$ and $Ar^4$ are independently of each other a bivalent group of the formula IV

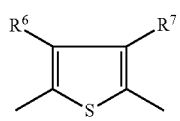

(IV)

wherein $R^6$ and $R^7$ are independently of each other hydrogen or $C_1$-$C_{25}$alkyl, b, c, e, and f independently of each other represent 1, 2 or 3

$Ar^2$, $Ar^3$, $Ar^5$, and $Ar^6$ are independently of each other a bivalent group of the formula IV,

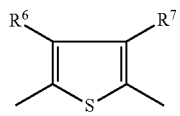

(IV)

wherein $R^6$ and $R^7$ are independently of each other hydrogen, $C_1$-$C_{25}$alkyl, or $C_7$-$C_{25}$aralkyl, and $R^3$ and $R^4$ are independently of each other a group of one of the formulae XI to XIII, XV, XVI and XIX (XI)
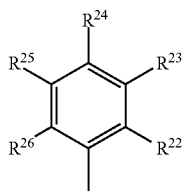

(XII)
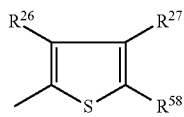

(XIII)
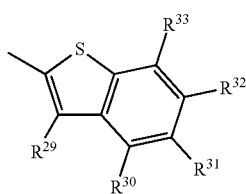

(XV)
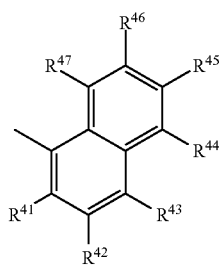

(XVI)
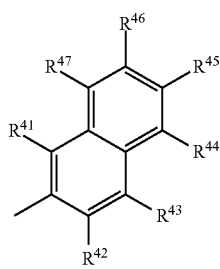

(XIX)
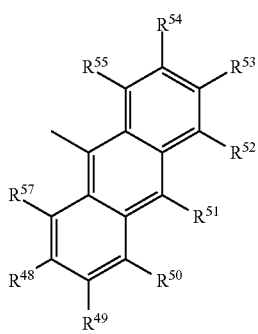

wherein $R^{22}$ to $R^{26}$, $R^{29}$ to $R^{33}$, $R^{41}$ to $R^{55}$, $R^{57}$ and $R^{58}$ represent independently of each other hydrogen, an aliphatic hydrocarbon group having up to 25 carbon atoms, aryl, alkoxy having up to 18 carbon atoms, or halogen, or two groups $R^{22}$ to $R^{26}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms.

Very preferred are especially the above-mentioned compounds of the formula I wherein $R^1$ and $R^2$ have the same meaning and the side chains of the formulae XLV and XLVI are identical to each other.

$$-[Ar^1]_a[Ar^2]_b[Ar^3]_c-R^3 \quad (XLV)$$

$$R^4-[Ar^6]_f[Ar^5]_e[Ar^4]_d- \quad (XLVI)$$

Most preferred are the compounds of the formula I described in the Examples, especially a compound of the general formula I selected from the compounds having the formulae 13, 22, 23, 24, 25, 26, 32, 38, 44, 45, 50, 55, 56, 58, 59, 60, 61, 63, 64, 70, 74, 76, 78, 80, 81, 82, 83, 84, 85, 86, 87, 88 and 89, respectively, which are depicted in the Examples.

The compounds of the formula I can be manufactured by known methods.

A possible route of manufacture starts from a compound of the formula XXXIV $$\text{(XXXIV)}$$

$$H-[-Ar^4]_d \begin{array}{c} H \\ N \\ \diagdown \\ O \end{array} \begin{array}{c} O \\ \diagup \\ \diagdown \\ N \\ H \end{array} [Ar^1]_a-H$$

wherein a and d represent 1 and $Ar^1$ and $Ar^4$ have the meanings given above, or from a compound of the formula XXXV $$\text{(XXXV)}$$

$$H-[-Ar^5]_e[Ar^4]_d \begin{array}{c} H \\ N \\ \diagdown \\ O \end{array} \begin{array}{c} O \\ \diagup \\ \diagdown \\ N \\ H \end{array} [Ar^1]_a[Ar^2]_b-H$$

wherein a and d represent 0, b and e represent 1, and $Ar^2$ and $Ar^5$ have the meanings given above.

Said starting compounds of the formulae XXXIV and XXXV can be obtained as described in U.S. Pat. No. 4,579,949 by reacting (in the presence of a strong base) one mole of a disuccinate, like dimethyl succinate, with 1 mole of a nitrile of the formulae XXXVI or XXXVII H—$Ar^1$—CN (XXXVI) H—$Ar^4$—CN (XXXVII) and 1 mole of a nitrile of the formulae XXXVIII or XXXIX. H—$Ar^2$—CN (XXXVIII) H—$Ar^5$—CN (XXXIX)

Alternatively, said starting compounds of the formulae XXXIV and XXXV can be obtained as described in U.S. Pat. No. 4,659,775 by reacting a nitrile with a suitable ester, like a pyrrolinon-3-carboxylic ester derivative.

The thus obtained compound of the formula XXXIV or the thus obtained compound of the formula XXXV is then N-alkylated for introduction of the groups $R^1$ and $R^2$, e.g. by reaction with a bromide of the formula $R^1$—Br or $R^2$—Br in the presence of a suitable base, like potassium carbonate, in a suitable solvent, like N-methyl-pyrrolidone. The reaction is carried out at a temperature from about room temperature to about 180° C., preferably from about 100° C. to about 170° C., e.g. at 140° C.

The thus obtained compound of the formula XL

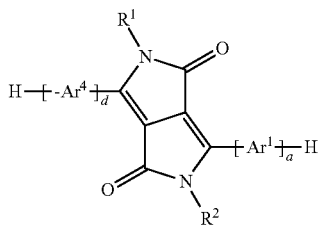

(XL)

wherein a and d represent 1, and $R^1$, $R^2$, $Ar^1$ and $Ar^4$ have the meanings given above, or the thus obtained compound of the formula XLI

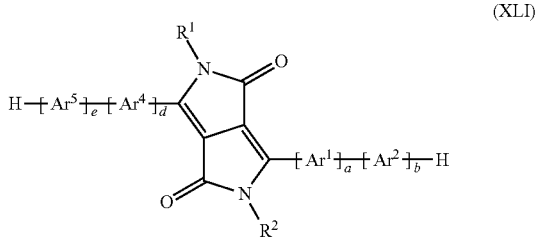

(XLI)

wherein a and d represent 0, b and e represent 1, and $R^1$, $R^2$, $Ar^2$ and $Ar^5$ have the meanings given above, is then reacted with a suitable brominating agent, like N-bromo-succinimide, to yield a compound of the formulae XLII and XLIII, respectively.

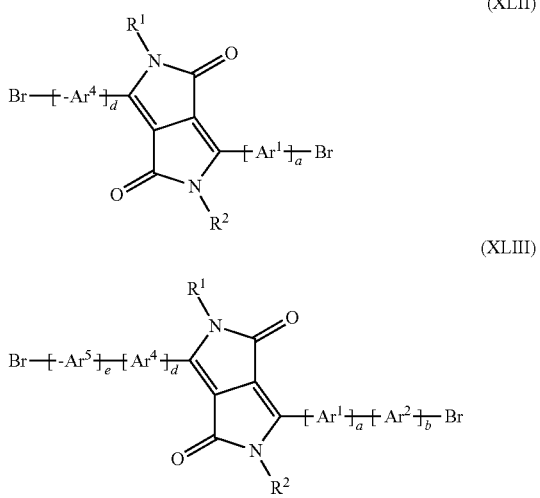

(XLII)

(XLIII)

The bromination is carried out in a suitable solvent, like chloroform, using two equivalents of N-bromo-succinimide at a temperature between −30° C. and +50° C., preferably between −10° C. and room temperature, e.g. at 0° C.

The compounds of the formulae XLII or XLIII can then be "side-chain-elongated", by step-wise adding further groups $Ar^1$—H, $Ar^4$—H, $Ar^2$—H, $Ar^5$—H, $Ar^3$—$R^3$, and $Ar^6$—$R^4$. The step-wise addition of these groups can be effected e.g. by reacting a compound of the formulae XLII or XLIII with a suitable tin compound of the formula XLIV

(XLIV)

wherein $R^{59}$ represents $C_{1-7}$alkyl, like butyl, and $Ar^{1-6}$ represents $Ar^1$—H, $Ar^4$—H, $Ar^2$—H, $Ar^5$—H, $Ar^3$—$R^3$, or $Ar^6$—$R^4$, respectively.

The reaction is carried out in the presence of a suitable palladium catalyst, like $Pd(P[C_6H_5]_3)_4$, in a suitable solvent, e.g. an aromatic hydrocarbon solvent, like toluene, at a temperature between about 50° C. and 180° C., e.g. under reflux, and under inert conditions including, inter alia, the use of dry solvents. After cooling down, the reaction mixture may be e.g. filtrated, e.g. on a double layer silica gel/Hyflo®, concentrated and the desired compound precipitated, e.g. by addition of methanol.

The "side-chain-elongation" of the compounds of the formulae XLII or XLIII with an additional thienyl residue can also be effected e.g. by reaction with a mixture of 2-thienylboronic acid pinacol ester, $Pd_2(dba)_3$ [tris(dibenzylideneacetone)-di-palladium)] and tri-tert-butyl-phosphonium-tetrafluoroborate in tetrahydrofurane.

The 2-thienylboronic acid pinacol ester may be obtained e.g. by adding substituted or unsubstituted thiophene to a mixture prepared from n-butyl-lithium and diisopropylamine and by adding 2-isopropoxy-4,4,5,5-tetramethyl-1,3,2-dioxaborolane to the thus obtained mixture.

Analogously, the "side-chain-elongation" of the compounds of the formulae XLII or XLIII with an additional phenyl or biphenyl residue may be effected with phenyl-boronic acid pinacol ester or biphenyl-boronic acid pinacol ester.

Alternatively, for the manufacture of compounds of the formula I wherein the side chains of the formulae XLV and XLVI

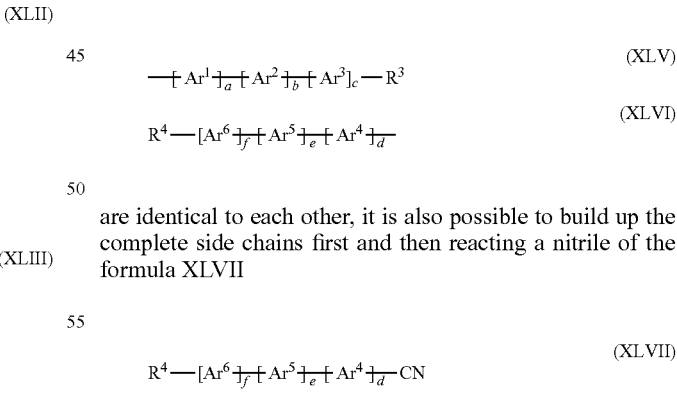

(XLV)

(XLVI)

are identical to each other, it is also possible to build up the complete side chains first and then reacting a nitrile of the formula XLVII

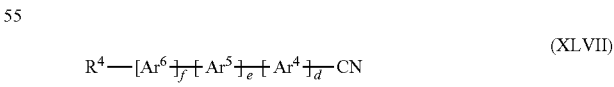

(XLVII)

with a suitable disuccinate, e.g. di-tert-amyl succinate. For example, a mixture of iron(III)chloride ($FeCl_3$), sodium, and tert-amylalcohol may be heated to 60-160° C., e.g. 110° C., before a mixture of the nitrile of the formula XLVII and di-tert-amyl succinate is added drop wise. After stirring the reaction mixture until the reaction is complete, e.g. for about 19 hours at 110° C., the reaction mixture is poured onto a water-methanol mixture.

Compounds of the formulae XLVa and XLVIa containing the complete side chains can be

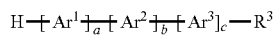 (XLVa)

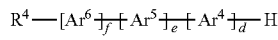 (XLVIa)

manufactured e.g. by reacting a bromo derivative of the formula Br—Ar$^1$ etc. first with magnesium in diethyl ether and then adding the thus obtained Grignard solution to a solution in diethyl ether of Ni(dppp)Cl$_2$ and a mono- or, if desired, dibromo compound of the formula Br—Ar$^2$ or Br—Ar$^2$T-Br, respectively.

The conversion of a compound of the formula XLVIa into the nitrile of the formula XLVII may be effected e.g. by adding a solution of a compound of the formula XLVIa, e.g. in toluene, to the reaction mixture obtained by adding triflic anhydride to a solution of N-formylmethylaniline in e.g. toluene, and reacting the obtained aldehyde of the formula XLVIIa

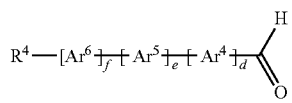 (XLVIIa)

with hydroxylamine sulfate in e.g. dimethyl formamide.

The thus obtained compound of the formula I wherein R$^1$ and R$^2$ are hydrogen may then be transformed into a desired end product of the formula I wherein R$^1$ and R$^2$ are e.g. an aliphatic, cycloaliphatic, cycloaliphatic-aliphatic, or aromatic-aliphatic group, like especially such an hydrocarbon group, by N-alkylation, e.g. analogously as described above, or by heating a solution thereof and potassium carbonate in dimethyl formamide followed by addition of R$^1$—Br or R$^2$—Br, or by reaction with a suitable iodide of the formula R$^1$—I or R$^2$—I. For example, a mixture of a compound of the formula I wherein R$^1$ and R$^2$ are hydrogen in N-methylpyrrolidone is treated, preferably under cooling, e.g. to a temperature between about 0° C. and 10° C., e.g. about 5° C., with a suitable strong base, e.g. a suitable hydride, like an alkali metal hydride, e.g. sodium hydride. Thereafter, the iodide of the formula R$^1$—I or R$^2$—I is added.

The nitrile of the formula XLVII used as starting material may be prepared e.g. from the corresponding aldehyde of the formula XLVIII,

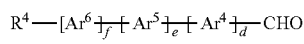 (XLVIII)

e.g. by reaction with hydroxylamine.

Said aldehyde of the formula XLVIII may be prepared e.g. from a compound of the formula IL,

 (IL)

e.g. by adding a solution of a compound of the formula IL in a suitable solvent, like toluene, to the reaction mixture of N-formylmethylaniline in a suitable solvent, like toluene, and triflic anhydride.

The present invention relates also to new starting materials, especially to compounds of the formula I wherein one or both of R$^1$ and R$^2$ are hydrogen, prefererably to such compounds which, like the end products of the formula I can also be used as the semiconductor layer in semiconductor devices. Preferred are those starting materials of the formula I wherein one or both of R$^1$ and R$^2$ are hydrogen and which contain at least two or three Ar groups in each side chain.

The compounds of the formula I show clear p-type transistor behavior and can be used as the semiconductor layer in semiconductor devices. Accordingly, the present invention also relates to a semiconductor device comprising as a semiconducting effective means a compound of the formula I

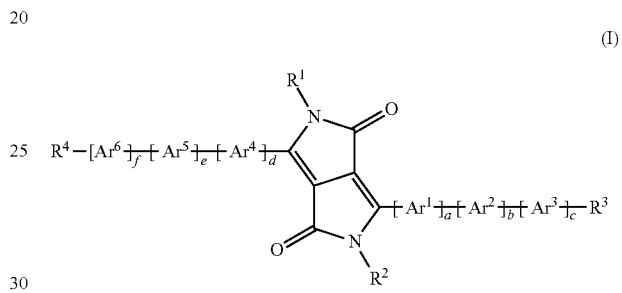 (I)

wherein R$^1$ and R$^2$ are independently of each other an aliphatic group having 7 to 25 carbon atoms, or a cycloaliphatic, cycloaliphatic-aliphatic, aromatic, aromatic aliphatic, heteroaromatic or heteroaromatic-aliphatic group having up to 25 carbon atoms, a and d independently of each other are 0, 1, 2 or 3, Ar$^1$ and Ar$^4$ are independently of each other a bivalent group of the formula II or IV

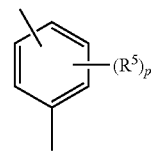 (II)

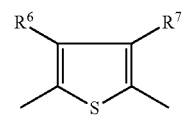 (IV)

wherein

R$^6$ and R$^7$ are as defined below, p represents 0, 1, or 2,

R$^5$ is an aliphatic hydrocarbon group having up to 25 carbon atoms, or two vicinal groups R$^5$ together represent alkylene or alkenylene having up to 7 carbon atoms, it being possible that two groups R$^5$ present in the group of formula II differ from each other, b and e independently of each other represent 1, 2 or 3, c and f independently of each other represent 0, 1, 2 or 3, Ar$^2$, Ar$^3$, Ar$^5$, and Ar$^6$ are independently of each other a bivalent group of one of the formulae IV to X and L,

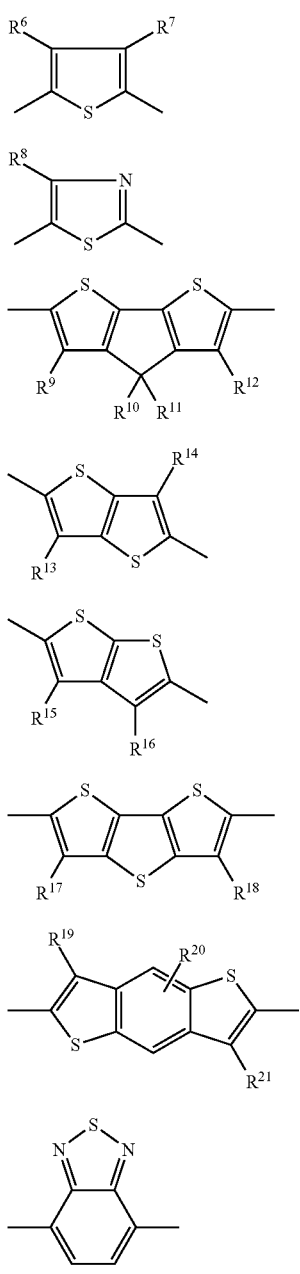

(IV)

(V)

(VI)

(VII)

(VIII)

(IX)

(X)

(L)

wherein $R^6, R^7, R^8, R^9, R^{12}, R^{13}, R^{15}, R^{16}, R^{17}, R^{18}, R^{19}, R^{20}$ and $R^{21}$ are independently of each other hydrogen, $C_1$-$C_{25}$alkyl, $C_1$-$C_{18}$alkoxy, $C_6$-$C_{24}$aryl, $C_7$-$C_{25}$aralkyl, or heteroaryl, or $R^6$ and $R^7$ together represent alkylene or alkenylene which may be both bonded via oxygen and/or sulfur to the thienyl residue and which may both have up to 25 carbon atoms, $R^{10}$ and $R^{11}$ are independently of each other hydrogen, $C_1$-$C_{18}$alkyl, $C_6$-$C_{24}$aryl, heteroaryl, or $R^{10}$ and $R^{11}$ together represent oxo or form a five or six membered ring, which is unsubstituted or substituted by a) an aliphatic hydrocarbon group having up to 18 carbon atoms, b) $C_1$-$C_{18}$alkoxy or $C_2$-$C_{18}$alkylenedioxy in both of which carbon atoms which are not adjacent to oxygen may be replaced by oxygen, or c) $C_6$-$C_{24}$aryl, $C_7$-$C_{25}$aralkyl, heteroaryl, $C_3$-$C_{12}$cycloalkyl or $C_4$-$C_{12}$cycloalkyl-alkyl, and $R^3$ and $R^4$ are independently of each other a group of one of the formulae XI to XIX,

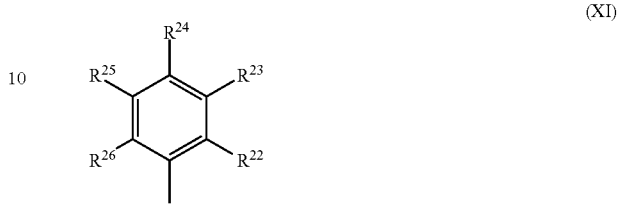

(XI)

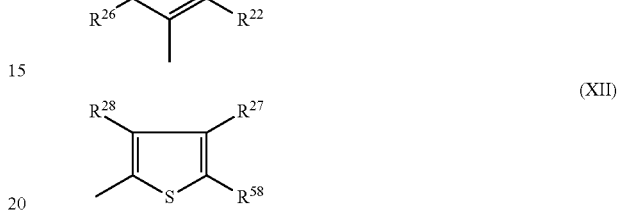

(XII)

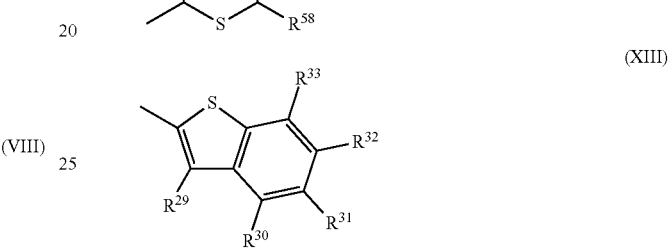

(XIII)

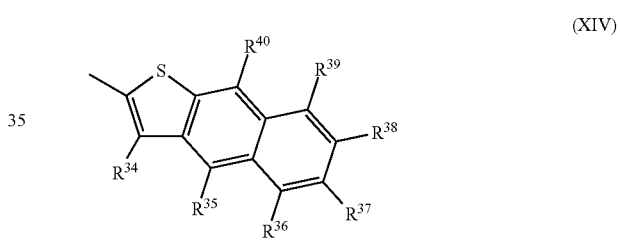

(XIV)

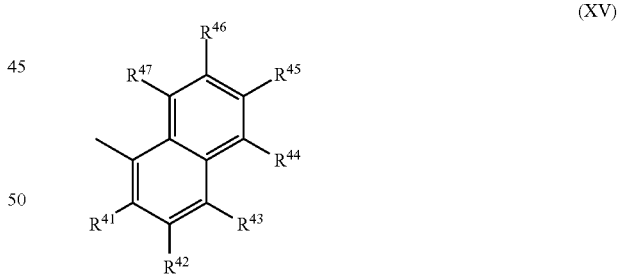

(XV)

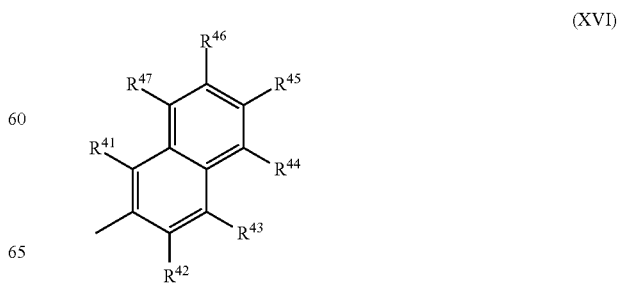

(XVI)

-continued

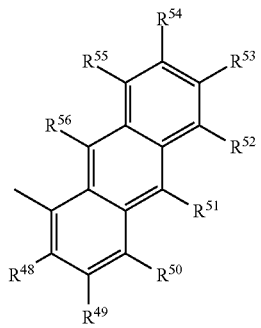

(XVII)

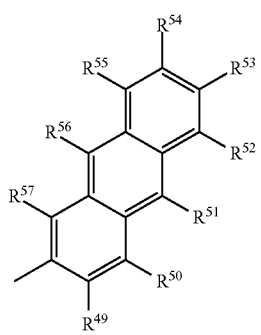

(XVIII)

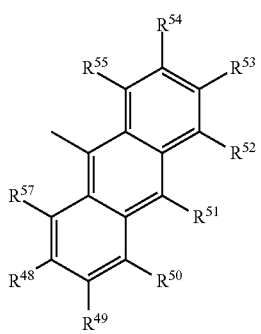

(XIX)

wherein $R^{22}$ to $R^{26}$ and $R^{29}$ to $R^{58}$ represent independently of each other hydrogen, an aliphatic hydrocarbon group having up to 25 carbon atoms, or a group of the formula (III)

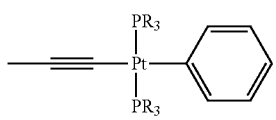

(III)

wherein R represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein R represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms, especially to a semiconductor device comprising as a semiconducting effective means a compound of the formula I as defined in this paragraph with the proviso that at least one of $R^6$, $R^7$, $R^{27}$, $R^{28}$ and $R^{58}$ is different from hydrogen.

The invention relates especially to a semiconductor device comprising as as a semiconducting effective means a compound of the formula I described in the Examples selected from the compounds having the formulae 3, 16, 53, 67, 68, 69, 71, and 77, respectively, which are depicted in the Examples.

Preferably, the invention relates to a semiconductor device comprising as as a semiconducting effective means a compound of the general formula I selected from the compounds having the formulae 13, 22, 23, 24, 25, 26, 32, 38, 44, 45, 50, 55, 56, 58, 59, 60, 61, 63, 64, 70, 74, 76, 78, 80, 81, 82, 83, 84, 85, 86, 87, 88, and 89, respectively, which are depicted in the Examples.

Preferably said semiconductor device is a diode, a photodiode, a sensor, an organic field effect transistor (OFET), a transistor for flexible displays, or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly (ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide (ITO), or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly(vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybrid materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising
a plurality of electrically conducting gate electrodes disposed on a substrate;
a gate insulator layer disposed on said electrically conducting gate electrodes;
a plurality of sets of electrically conductive source and drain electrodes disposed on said insulator layer such that each of said sets is in alignment with each of said gate electrodes;
an organic semiconductor layer disposed in the channel between source and drain electrodes on said insulator layer substantially overlapping said gate electrodes; wherein said organic semiconductor layer comprise a compound of the formula I.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer comprising a compound of the formula I on said insulator layer such that said layer comprising the compound of formula I substantially overlaps said gate electrodes, thereby producing the thin film transistor device.

The above-mentioned layer comprising a compound of formula I may additionally comprise at least another material. The other material can be, but is not restricted to another compound of the formula I, a semi-conducting polymer, a polymeric binder, organic small molecules different from a compound of the formula I, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more small molecules of the formula I and a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO 2008/001123 A1).

For heterojunction solar cells (bulk heterojunction solar cells) the active layer comprises preferably a mixture of a compound of the formula I and a fullerene, such as [60] PCBM (=6,6-phenyl-$C_{61}$-butyric acid methyl ester), or [70] PCBM, in a weight ratio of 1:1 to 1:3. Methanofullerene Phenyl-$C_{61}$-Butyric-Acid-Methyl-Ester ([60]PCBM), i.e. 1-[3-(methoxy-carbonyl)propyl]-1-phenyl-[6.6]$C_{61}$-3'H-cyclopropa[1,9][5,6]fullerene-$C_{60}$-1h-3'-butanoic acid 3'-phenyl methyl ester, is an effective solution processable n-type organic semiconductor. It is blended with conjugated polymers with nano-particles such as $C_{60}$.

Any suitable substrate can be used to prepare the thin films of the compounds of the formula I. Preferably, the substrate used to prepare the above thin films is a metal, silicon, plastic, paper, coated paper, fabric, glass or coated glass.

Alternatively, a TFT is fabricated, for example, by solution deposition of a compound of the formula I on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the compound of the formula I to form a thin film.

The gate electrode could also be a patterned metal gate electrode on a substrate or a conducting material such as a conducting polymer, which is then coated with an insulator applied either by solution coating or by vacuum deposition on the patterned gate electrodes.

Any suitable solvent can be used to dissolve, and/or disperse a compound of the formula I, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl formamide, dichlorobenzene, trichlorobenzene, propylene glycol monomethyl ether acetate (PGMEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising a compound of the formula I, which is not fully dissolved in a solvent. The dispersion can be done selecting a composition including at least a compound of formula I, or a mixture containing a compound of formula I, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;

dissolving at the elevated temperature at least a portion of the compound of the formula I in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of formula I, or a mixture containing a compound of formula I of the present invention. The degree of solubility of the compound of formula I in the solvent may vary for example from 0.5% to about 20% solubility, particularly from 1% to about 5% solubility.

Preferably, the thickness of the organic semiconductor layer is in the range of from about 5 to about 1000 nm, especially the thickness is in the range of from about 10 to about 100 nm.

The compounds of the formula I can be used alone or in combination as the organic semiconductor layer of the semiconductor device. The layer can be provided by any useful means, such as, for example, vapor deposition and printing techniques. The compounds of the formula I which are sufficiently soluble in organic solvents can be solution deposited and patterned (for example, by spin coating, dip coating, ink jet printing, gravure printing, flexo printing, offset printing, screen printing, microcontact (wave)-printing, drop or zone casting, or other known techniques).

The compounds of the formula I can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambi-polarity the material can also be used in Organic Light Emitting Transistors (OLET).

The invention provides organic photovoltaic (PV) devices (solar cells) comprising a compound of the formula I.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula I. Preferably, the photoactive layer is made of a compound of the formula I, as an electron donor and an acceptor material, like a fullerene, particularly a functionalized fullerene PCBM, as an electron acceptor. As stated above, the photoactive layer may also contain a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another polymer of formula I or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form. Highly transparent, non-metallic, low resistance cathodes or highly efficient, low resistance metallic/non-metallic compound cathodes are, for example, disclosed in U.S. Pat. No. 6,420,031 and U.S. Pat. No. 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxythiophene:polystyrene-sulfonate (PEDOT:PSS).

In a preferred embodiment of the present invention, the photovoltaic cell comprises, as described for example, in U.S. Pat. No. 6,933,436 a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few urn depending on the application method, and is applied onto this smoothing layer. The photoactive layer is made of a compound of the formula I, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to the photoactive layer. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment of the invention, one or more of the layers may be treated with plasma prior to depositing the next layer. It is particularly advantageous that prior to the deposition of the PEDOT:PSS layer the anode material is subjected to a mild plasma treatment.

As an alternative to PEDOT:PSS a crosslinkable hole-transport material based on triarylamines as referenced in Macromol. Rapid Commun. 20, 224-228 (1999) can be used.

In addition to the triarylamine material the layer can also include an electron acceptor to improve electron transport. Such compounds are disclosed in US 2004/0004433. Preferably, the electron acceptor material is soluble in one or more organic solvents. Typically, the electron acceptor material is present in the range of 0.5 to 20% by weight of the triarylamine material.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:

(a) a cathode (electrode), (b) optionally a transition layer, such as an alkali halogenide, especially lithium fluoride, (c) a photoactive layer, (d) optionally a smoothing layer, (e) a middle electrode (such as Au, Al, ZnO, $TiO_2$ etc.)

(f) optionally an extra electrode to match the energy level, (g) optionally a transition layer, such as an alkali halogenide, especially lithium fluoride, (h) a photoactive layer, (i) optionally a smoothing layer, (j) an anode (electrode), (k) a substrate.

The PV device can also be processed on a fiber as described, for example, in US20070079867 and US 20060013549.

Due to their excellent self-organising properties the materials or films comprising the compounds of the formula I can also be used alone or together with other materials in or as alignment layers in LCD or OLED devices, as described for example in US200310021913.

The following examples illustrate the invention.

Abbreviations:

m.p. melting point

In the reported NMR spectra the following abbreviations are used:

d: dublet dd: dublet of dublet m: multiplet s: singulet t: triplet quint: quintet sext: sextet

EXAMPLE 1

Manufacture of the Semiconducting Compound of the Formula 3

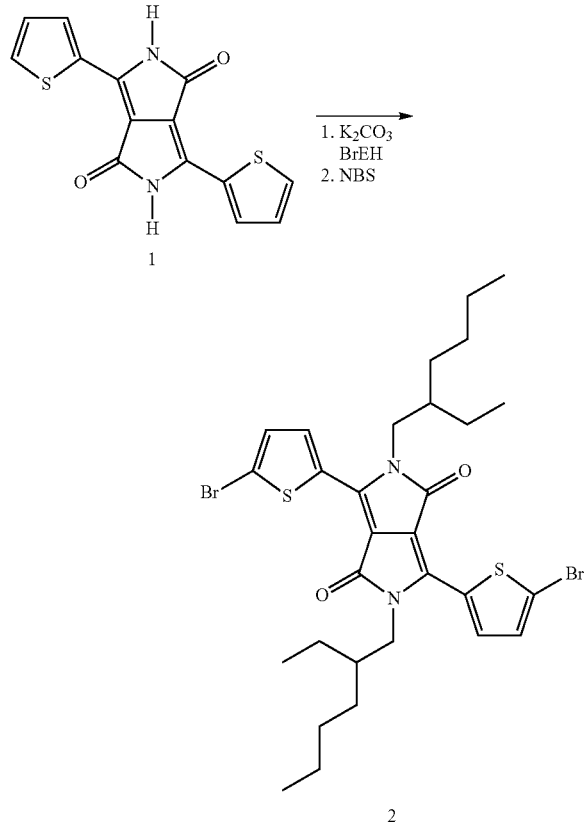 [SMILES: O=C1NC(c2cccs2)=C2C(=O)NC(c3cccs3)=C12 ; CCCCC(CC)CN1C(=O)C2=C(c3ccc(Br)s3)N(CC(CC)CCCC)C(=O)C2=C1c1ccc(Br)s1]

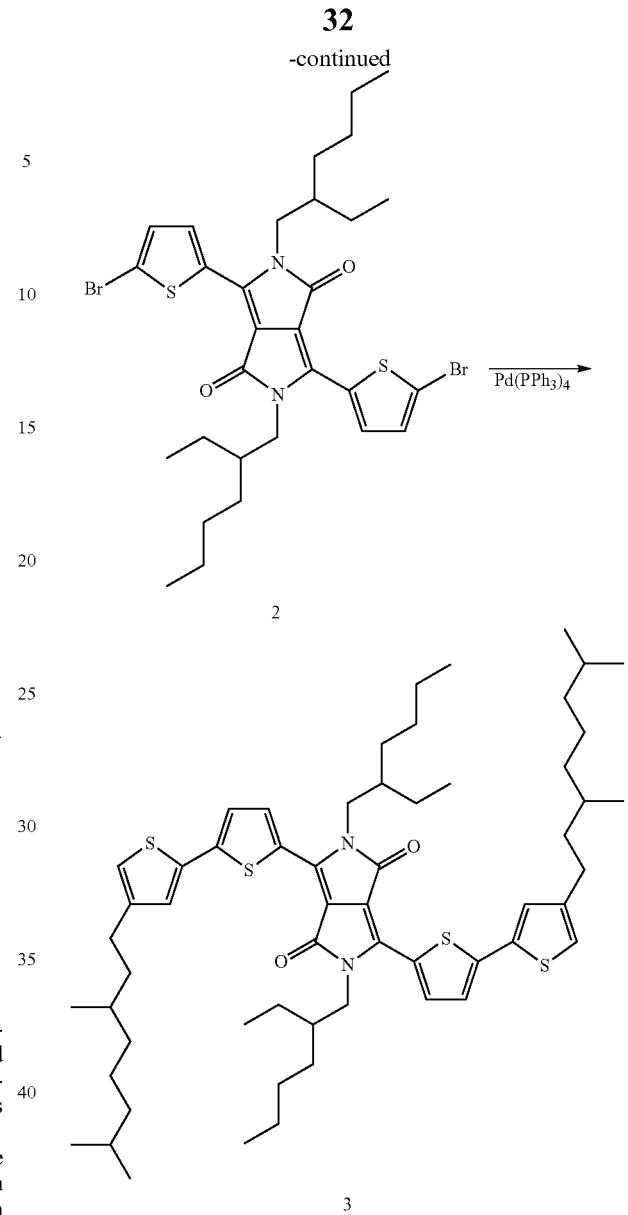

a) A solution of 4.5 g of the 1,4-diketopyrrolo[3,4-c]pyrrole (DPP) derivative of the formula 1, 6.23 g of $K_2CO_3$ and 8.68 g of 1-bromo-2-ethyl-hexyl in 60 ml of N-methyl-pyrrolidone (NMP) is heated to 140° C. for 6 h. The mixture is washed with water and extracted with dichloromethane.

The organic phase is then dried and filtered on a double layer of silica gel and Hyflo® (CAS 91053-39-3; Fluka 56678) before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 1.90 g of a violet powder of the DPP derivative of the formula 2.

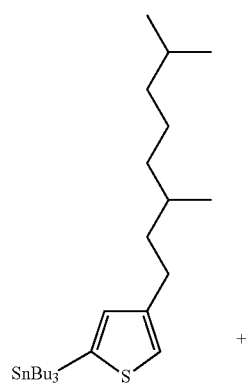

b) A solution of 1.28 g of the dibrominated DPP derivative of the formula 2, 2.41 g of the tin derivative depicted above, and 215 mg of $Pd(PPh_3)_4$ in 30 ml of dry toluene is refluxed overnight under inert conditions. After cooling down, the mixture is filtrated on a double layer silica gel/Hyflo®, concentrated and precipitated with methanol. The precipitate is filtrated and rinsed with methanol to give 1.17 g of a blue solid of the DPP derivative of the formula 3.

EXAMPLE 2

Application of the Semiconducting Compound of the Formula 3

Bottom-gate thin film transistor (TFT) structures with p-Si gate (10 cm) are used for all experiments. A high-quality thermal $SiO_2$ layer of 300 nm thickness served as gate-insulator of $C_i$=32.6 nF/cm² capacitance per unit area. Source and drain electrodes are patterned by photolithography directly on the gate-oxide. Gold source drain electrodes defining channels of width W=10 mm and varying lengths L=4, 8, 15, 30 m are used. Prior to deposition of the organic semiconductor the SiO$_2$ surface is derivatized either with hexadimethylsilazane (HMDS) by exposing to a saturated silane vapour at 160° C. for 2 hours or treating the substrate at 60° C. with a 0.1 m solution of octadecyltrichlorosilane (OTS) in toluene for 20 minutes. After rinsing with iso-propanol the substrates are dried.

The semiconductor thin film is prepared either by spin-coating or drop casting the DPP derivative of the formula 3 obtained in example 1 in a 1% (w/w) solution in toluene. Before use the solution is filtered through 0.2 m filter. The spin coating is accomplished at a spinning speed of 800 rpm (rounds per minute) for about 20 seconds in ambient conditions. The devices are dried at 80° C. for 1 hour before evaluation.

Transistor Performance

The transistor behaviour is measured on an automated transistor prober (TP-10, CSEM Zürich). From a linear fit to the square root of the saturated transfer characteristics a field effect mobility of $1\times10^{-03}$ cm$^2$/Vs with an on/off current ratio of $8.9\times10^5$ can be determined. The threshold voltage is at −3.0 V.

Electrochemical Measurements According to Method A

Electrochemical data are obtained by cyclic voltammetry (Princeton Applied Research-Versastat II) in solution. The experiments are performed under argon in a saturated solution of anhydrous methylene chloride with 0.1 m tetrabutyl-ammonium hexafluorophosphate as the supporting electrolyte. A silver Ag/AgCl couple is used as pseudoreference electrode. All data are referenced to the ferrocene/ferrocenium redox couple, that is measured after the scan in the same system. Ferrocene is bis($\eta^5$-cyclopentadienyl)iron. Ferrocenium is the oxidated form of ferrocene. The scan rate is 50 mV/s.

For each sample, the level is estimated using the formal potential ($E_{1/2}$) with the assumption that ferrocene, used as the internal standard, has a HOMO (highest occupied molecular orbital) level of −4.8 eV.

The resulting level HOMO level of example 1, i.e. of the compound of the formula 3, corresponds to a HOMO level of approx. −5.21 eV, respectively a LUMO (lowest unoccupied molecular orbital) level of −3.31 eV.

Electrochemical Measurements According to Method B

For the example 2 and the following examples electrochemical data are obtained by cyclic voltammetry (Princeton Applied Research-Versastat II) following a slightly different method as described above for method A (inter alia, thin film instead of saturated solution). The experiments are performed at room temperature under argon on drop-cast thin films in anhydrous acetonitrile with 0.1 m tetrabutyl-ammonium tetrafluoroborate as the supporting electrolyte. A silver Ag/AgCl couple was used as pseudoreference electrode. All data are referenced to the ferrocene/ferrocenium redox couple, that is measured after the scan in the same system. The scan rate is 100 mV/s (millivolt per second).

For each sample, the level is estimated using the formal potential ($E_{1/2}$) with the assumption that ferrocene, used as the internal standard, has a HOMO level of −5.15 eV (electron volt).

The resulting level of the DPP derivative of formula 3 corresponds to a HOMO level of approx. −5.5 eV, respectively a LUMO level of −3.8 eV.

In the perspective of using the compound of formula 3 blended with [60]PCBM in a solar cell device electrochemical data of [60]PCBM are also obtained by cyclic voltammetry of a thin film. The resulting level of [60]PCBM corresponds to a HOMO level of approx. −6.0 eV, respectively a LUMO level of −4.3 eV.

EXAMPLE 3

Photovoltaic Application of the Semiconducting Compound of Formula 3

A glass substrate (0.55 mm thickness) with patterned ITO (indium tin oxide) layer (65 nm thickness, Rs=15 Ohm) is used as basis for manufacturing the photovoltaic cell. A hole injection and smoothing layer (PEDOT:PSS Baytron P, Bayer A G) is applied onto the patterned ITO layer by spin coating at a rotating speed of 1500 rpm for 1 minute and then accelerating up to 4000 rpm. 10 mg of the compound of the formula 3 together with 10 mg of [60]PCBM fullerene are dissolved in 1 ml of toluene, heated up to 50° C. and stirred for 3 hours and finally applied onto the electron blocking layer by spin-coating at 500 rpm. The so-formed active layer is then covered with a 1 nm thick LiF (lithium fluoride) hole blocking layer and 100 nm Al (aluminium) electrode, both applied under vacuum in a vapour deposition equipment (Bestec, Germany). The actual area of active layer sandwiched between both ITO and Al electrodes is about 9 mm$^2$.

The so-formed photovoltaic solar cell is exhibiting surprisingly good performance and efficiency when exposed to AM (Air Mass) 1.5 solar photon flux (photon flux: number of photons per second per unit area).

EXAMPLE 4

Manufacture of the Semiconducting Compound of the Formula 13

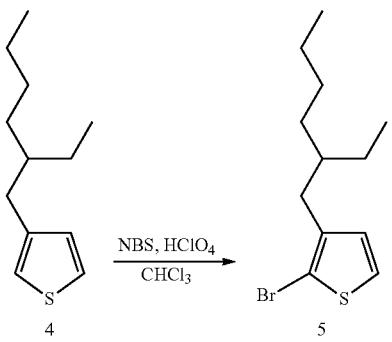

a) To a solution of 40 g of 3-(2-ethylhexyl)thiophene of the formula 4 and 0.4 ml of perchloric acid in 350 ml of chloroform at 12° C. are added portion wise 36.2 g N-bromosuccinimide. At the end of the addition the mixture is allowed to regain room temperature and is stirred for one hour. The reaction mixture is extracted with water, dried and concentrated. The product is thereafter fractionated over a Vigreux column to yield 39.7 g of compound 5 as colorless liquid; 1H-NMR data (ppm, CDCl$_3$): 7.11 1H d, 6.69 1H d, 2.43 2H d, 1.47-1.51 1H m, 1.15-1.23 8H m, 0.81 6H t.

b) Synthesis of Compound 7

Version 1 Via a Kumada Cross-Coupling Reaction

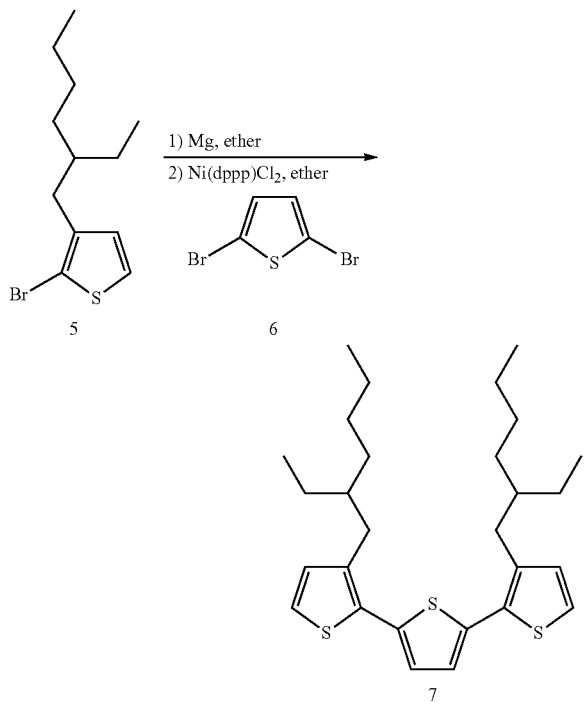

In a reactor 0.28 g of freshly activated magnesium turnings are suspended in 20 ml of diethyl ether and 2.7 g of the compound of the formula 5 are added carefully. The mixture is stirred for 2 hours at room temperature and then refluxed overnight.

Into a second reactor 22 mg of Ni(dppp)Cl₂ [dppp=propane-1,3-diylbis(diphenylphosphane)] and 1.0 g of 2,5-dibromothiophene of the formula 6 are suspended in 20 ml of diethyl ether and cooled to 7° C. before the freshly prepared Grignard solution of the compound of the formula 5 is added drop wise. The obtained dark mixture is stirred at room temperature over night. The reaction is quenched by the addition of 10% of hydrochloric acid (HCl). After completion the mixture is washed with water, dried and concentrated. Purification by distillation followed by column chromatography on silica gel affords 1.05 g of compound 7 as slightly yellow oil.

Version 2 Via a Suzuki Cross-Coupling Reaction

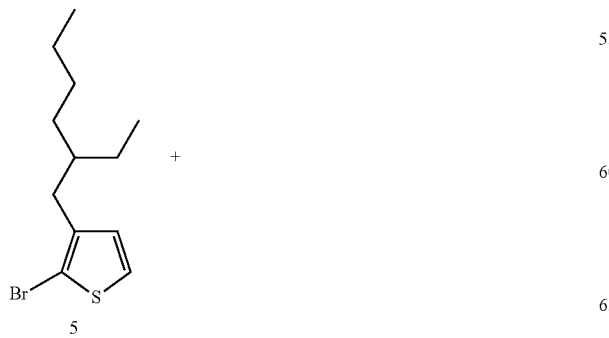

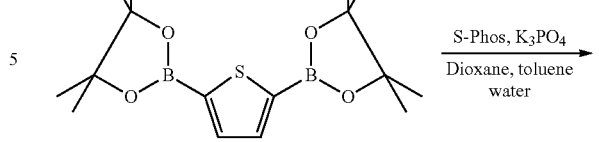

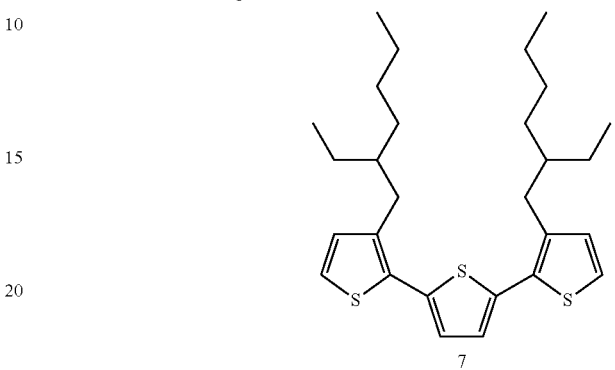

A mixture of 4.1 g of compound 5, 2.0 g of the diboronic ester of the formula 8, 6.9 g of potassium phosphate ($K_3PO_4$), 0.7 g of 2-dicyclohexylphosphino-2',6'-dimethoxybiphenyl (S-Phos), 67 mg of palladium(II)acetate, 20 ml of dioxane, 20 ml of toluene and 12 ml of water is heated to 95° C. for 21 hours. The obtained mixture is diluted with diethyl ether and extracted with water, dried and concentrated. Purification is performed by bulb to bulb distillation followed by column chromatography on silica gel and yields 1.9 g of compound 7 as slightly yellow oil; 1H-NMR data (ppm, CDCl₃): 7.18 2H d, 7.04 2H s, 6.91 2H d, 2.72 4H d, 1.63-1.67 2H m, 1.23-1.36 16H m, 0.81-0.86 12H m.

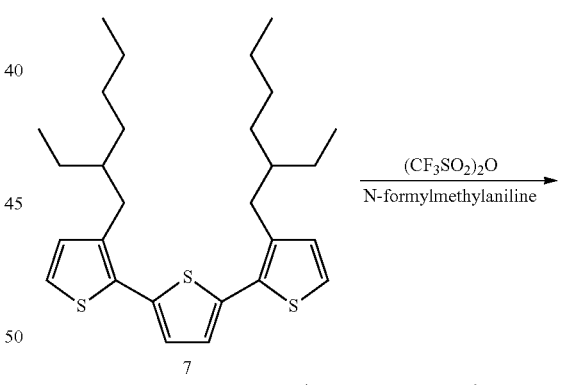

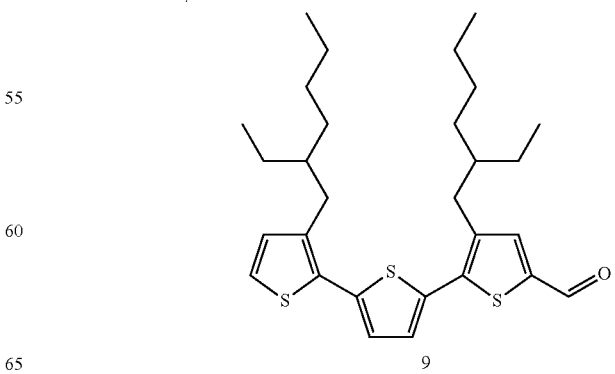

c) To a solution of 0.66 g of N-formylmethylaniline in 10 ml of toluene are added at 5° C. 1.34 g of triflic anhydride, while a white precipitate is formed. The reaction mixture is allowed to return to room temperature before 2.0 g of compound 7 are added, dissolved in 10 ml of toluene. The mixture is heated to 110° C. for 22 hours. After cooling to room temperature 5 ml of a 10% sodium hydroxide solution are added. The mixture is then extracted with water, dried and concentrated. Final purification is achieved by column chromatography on silica gel yielding 1.58 g of compound 9 as yellow oil; 1H-NMR data (ppm, CDCl$_3$): 9.84 1H s, 7.56 1H s, 7.23 1H d, 7.22 1H d, 7.01 1H d, 6.92 1H s, 2.76 2H, d, 2.72 2H d, 1.61-1.71 2H m, 1.23-1.39 16H m, 0.81-0.89 12H m.

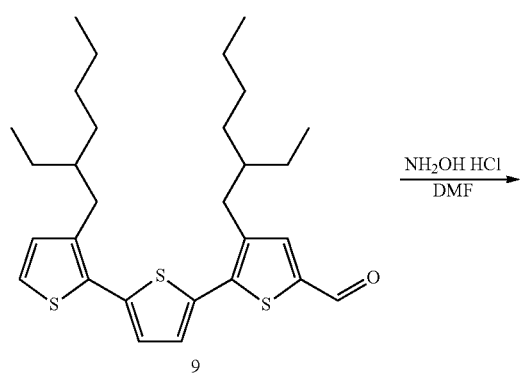

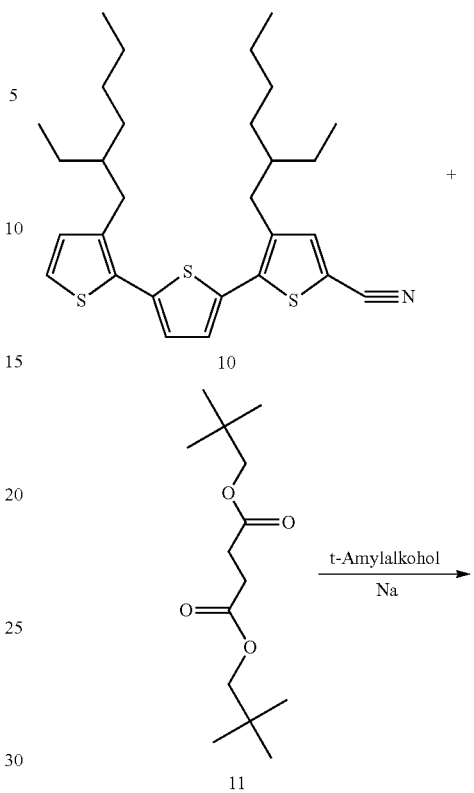

d) A mixture of 1.2 g of the aldehyde of the formula 9 and 0.2 g of hydroxylamine hydrochloride in 10 ml of dimethyl formamide (DMF) is heated to 145° C. for 16 hours. After cooling to room temperature the mixture is diluted with diethyl ether, washed with water, dried and concentrated. The crude product is purified by filtration over a silica gel plug under reduced pressure affording 0.91 g of the desired nitrile of the formula 10 as dark oil.

1H-NMR data (ppm, CDCl$_3$): 7.41 1H s, 7.22 1H d, 7.14 1H d, 7.08 1H d, 6.92 1H s, 2.71 4H, d, 1.60-1.66 2H m, 1.17-1.35 16H m, 0.81-0.87 12H m.

e) A mixture of 5 mg iron trichloride (FeCl$_3$), 64 mg of sodium and 10 ml of t-Amylalcohol is heated to 110° C. for 20 minutes before a mixture of 0.5 g of the nitrile of the formula 10 and 0.16 g of di-tert-amyl succinate of the formula 11 is added drop wise. The reaction mixture is stirred at 110° C. for 19 hours before it is poured onto a water-methanol mixture. Büchner filtration and exhaustive washing with methanol affords 340 mg of the desired 1,4-diketopyrrolo[3,4-c]pyrrole (DPP) derivative of the formula 12 as dark blue powder; ESI-MS m/z (% int.): 1077.5 ([M+H]+, 100%).

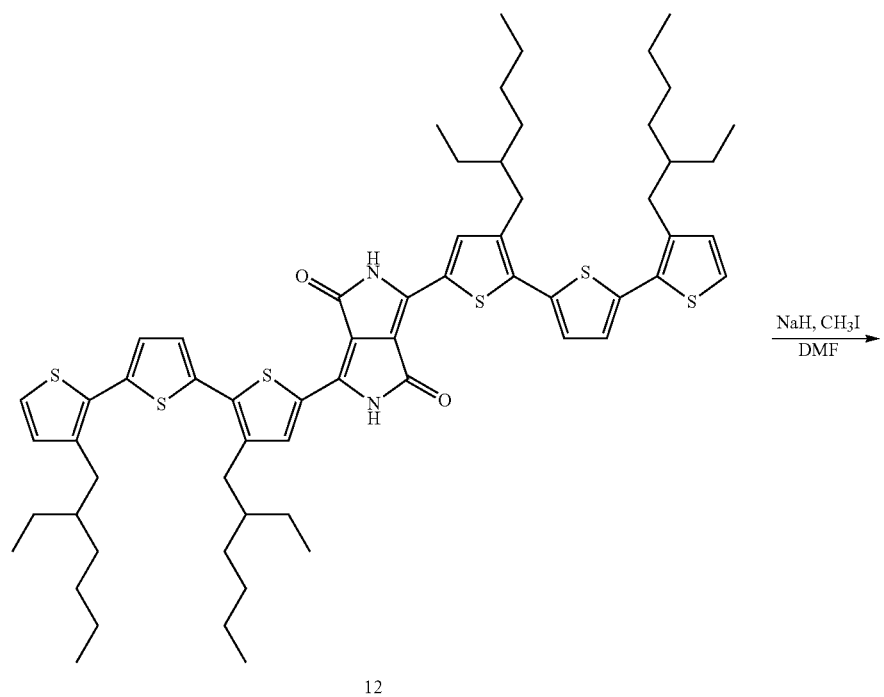

12

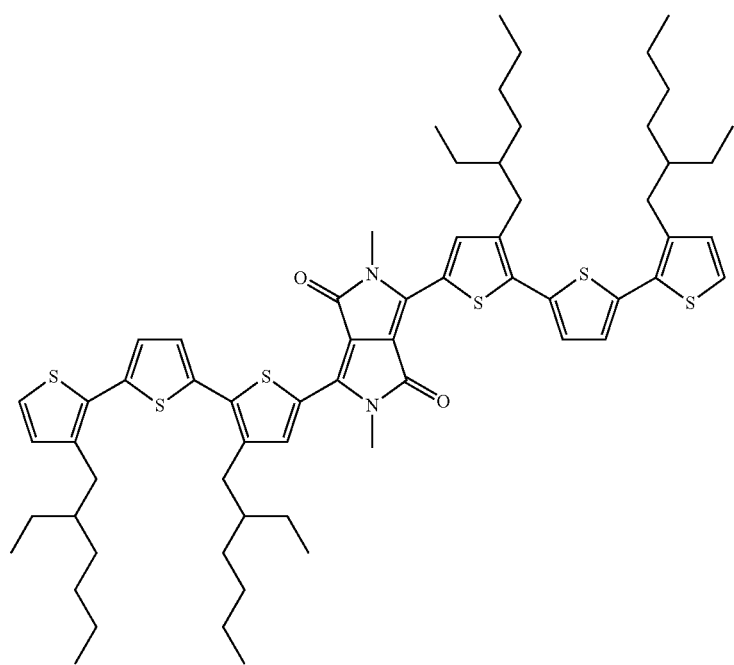

13 f) To a mixture of 0.25 g of the DPP derivative of the formula 12 in 10 ml of N-methyl-pyrrolidone (NMP) are added at 5° C. 28 mg of sodium hydride (NaH; 60% by weight in mineral oil). The mixture is allowed to warm to room temperature and is stirred for 2 hours at this temperature. After cooling to 5° C. 100 mg of methyl iodide (CH$_3$I) are added. The stirring is continued for 3 hours at room temperature before water is slowly added. The mixture is then poured into dichloromethane, washed with water and concentrated to 1 ml before methanol is added. The precipitate is collected by Büchner filtration and is washed several times with methanol to yield 180 mg of the DPP derivative of the formula 13 as dark blue powder; 1H-NMR data (ppm, CDCl$_3$): 8.85 2H s, 7.25 2H d, 7.23 2H d, 7.10 2H d, 6.92 2H s, 2.83 4H, d, 2.74 4H d, 1.80-1.85 2H m, 1.65-1.67 2H m, 1.24-1.42 32H m, 0.82-0.91 24H m.

EXAMPLE 5

Manufacture of the Semiconducting Compound of the Formula 16

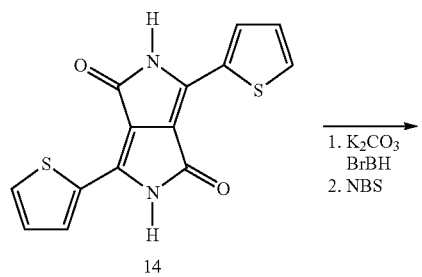

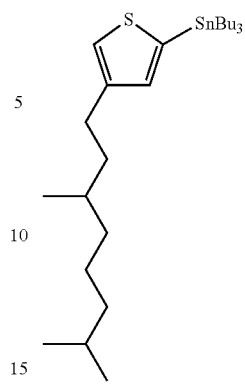

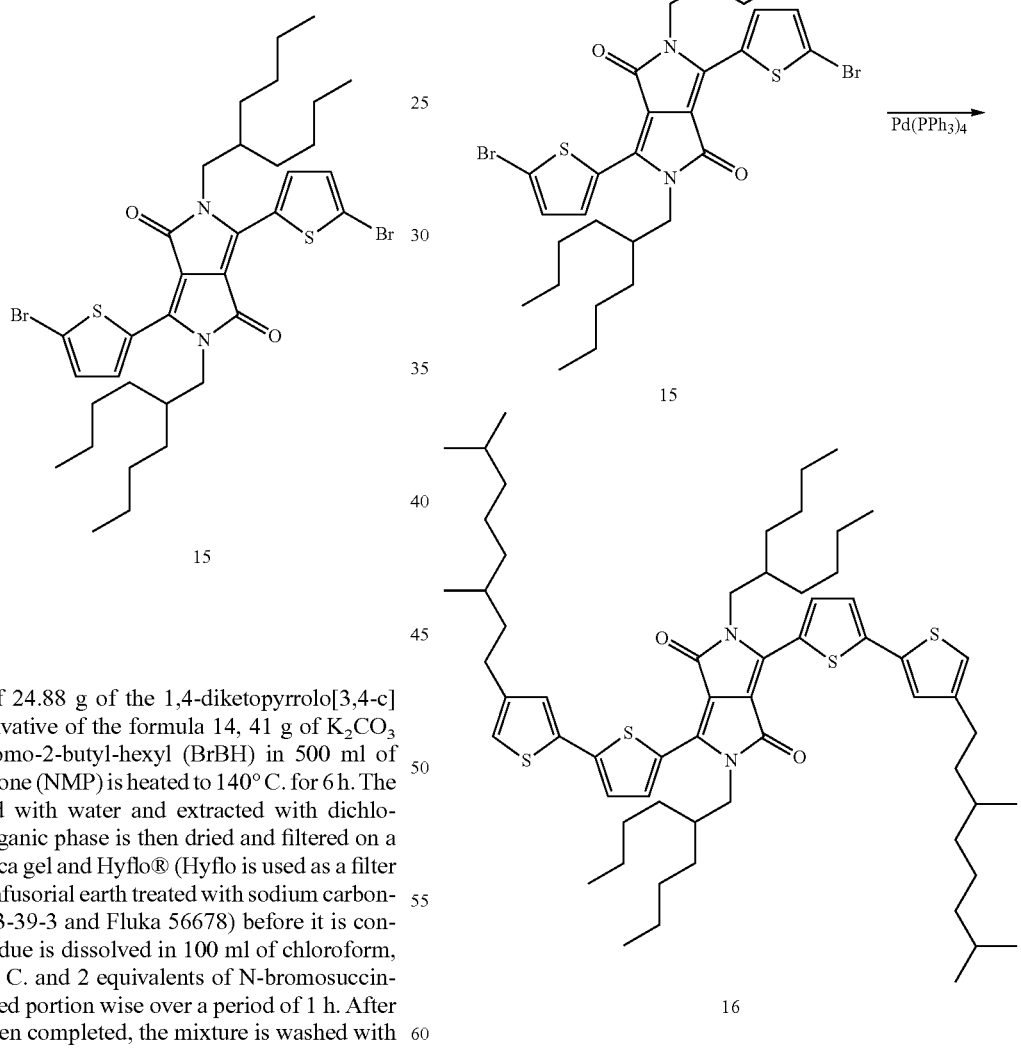

a) A solution of 24.88 g of the 1,4-diketopyrrolo[3,4-c]pyrrole (DPP) derivative of the formula 14, 41 g of $K_2CO_3$ and 55 g of 1-bromo-2-butyl-hexyl (BrBH) in 500 ml of N-methyl-pyrrolidone (NMP) is heated to 140° C. for 6 h. The mixture is washed with water and extracted with dichloromethane. The organic phase is then dried and filtered on a double layer of silica gel and Hyflo® (Hyflo is used as a filter aid. It is calcined infusorial earth treated with sodium carbonate, cf. CAS 91053-39-3 and Fluka 56678) before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 9.5 g of a violet powder of the DPP derivative of the formula 15. $^1$H-NMR data (ppm, $CDCl_3$): 8.59, d, 4.1 Hz; 7.21, d, 4.1 Hz; 3.91, d; 7.6 Hz; 1.88, m; 1.30, m; 0.86, t, 7.4 Hz. $^{13}$C NMR ($CDCl_3$) 161.54; 139.57; 135.40; 131.61; 119.14; 108.28; 46.68; 38.06; 31.23; 28.76; 23.39; 14.37.

b) A solution of 2.24 g of the dibrominated DPP derivative of the formula 15, 3.9 g of the tin derivative depicted above, and 351 mg of $Pd(PPh_3)_4$ in 50 ml of dry toluene is refluxed overnight under inert conditions. After cooling down, the mixture is filtrated on a double layer silica gel/Hyflo®, concentrated and precipitated with methanol. The precipitate is filtrated and rinsed with methanol to give 1.56 g of a blue solid of the DPP derivative of the formula 16; m.p. 139.5° C.; $^1$H-NMR data (ppm, CDCl$_3$): 8.85 2H d 4.1 Hz; 7.27 2H d 4.1 Hz; 7.16 2H s; 6.92 2H s, 4.03 4H d 7.3 Hz; 2.61 4H m; 2.00 2H m; 1.4 44H m; 0.88 30H m.

EXAMPLE 6

Application of the Semiconducting Compound of the Formula 16

The semiconductor thin film is prepared either by spin-coating or drop casting the DPP derivative of the formula 16 obtained in example 5 in a 0.5% (w/w) solution in chloroform. The spin coating is accomplished at a spinning speed of 3000 rpm (rounds per minute) for about 20 seconds in ambient conditions. The devices are evaluated as deposited and after being annealed by heating at 100° C. for 15 minutes.

Transistor Performance

The transistor behavior is measured on an automated transistor prober (TP-10, CSEM Zürich) and showed clear p-type transistor behavior. From a linear fit to the square root of the saturated transfer characteristics a field effect mobility of $3.7 \times 10^{-3}$ cm$^2$/Vs with an on/off current ratio of $1.7 \times 10^5$ can be determined. The threshold voltage is about 2 V to 4 V.

Electrochemical Measurements

Electrochemical data are obtained by cyclic voltammetry (Princeton Applied Research-Versastat II) following exactly the same procedure as described in example 2, method B, i.e. the thin-film method. The resulting level of the DPP derivative of formula 16 corresponds to a HOMO level of approx. −5.5 eV, respectively a LUMO (lowest unoccupied molecular orbital) level of −3.8 eV.

EXAMPLE 7

Photovoltaic Application of the Semiconducting Compound of Formula 16

DPP-Monomer Based Bulk Heterojunction Solar Cell

The solar cell has the following structure: Al (aluminium) electrode/LiF (lithium fluoride) layer/organic layer, including the compound of the formula 16 and the fullerene [60]PCBM/poly(3,4-ethylenedioxy-thiophene) (PEDOT) in admixture with poly(styrenesulfonic acid) (PSS)]/ITO (indium tin oxide) electrode/glass substrate. The solar cells are made by spin coating a layer of the PEDOT-PSS on a pre-patterned ITO on glass substrate. Then a 1:1 mixture by weight of compound 16 (1% by weight in chloroform) and [60]PCBM (a substituted C$_{60}$ fullerene) (also 1% by weight in chloroform) is spin coated (organic layer). LiF and Al are sublimed under high vacuum through a shadow-mask.

Solar Cell Performance of the Bulk Heterojunction Solar Cell

The solar cell is measured under a solar light simulator. Then with the External Quantum Efficiency (EQE) graph the current is estimated under AM1.5 conditions. This leads to a value of $J_{sc}$=7.1 mA/cm$^2$ (milliampere per square centimeter, $J_{sc}$ means short circuit current), FF=0.45 (FF=fill factor) and $V_{oc}$=0.83 V ($V_{oc}$=open circuit voltage), wherefrom an overall efficiency of 2.65% is calculated.

DPP-Monomer Based Bilayer Solar Cell

The bilayer solar cell has the following structure: Al electrode/LiF layer/[60]PCBM (a substituted C$_{60}$ fullerene)/organic layer of the compound 16/poly(3,4-ethylenedioxy-thiophene) (PEDOT) in admixture with poly(styrenesulfonic acid) (PSS)]/ITO electrode/glass substrate. The solar cells are made by spin coating a layer of the PEDOT-PSS on a pre-patterned ITO on glass substrate. Then a layer of the compound of formula 16 (1% by weight) is spin coated (organic layer). C$_{60}$, LiF and Al are sublimed under high vacuum through a shadow-mask.

Solar Cell Performance of the Bilayer Solar Cell

The solar cell is measured under a solar light simulator. Then with the External Quantum Efficiency (EQE) graph the current is estimated under AM1.5 conditions. This leads to a value of $J_{sc}$=0.013 mA/cm$^2$, FF=0.26 and $V_{oc}$=0.65 V, wherefrom an overall efficiency of 0.0023% is calculated.

As evident from a comparison of the above bulk heterojunction solar cell with the bilayer solar cell the overall solar cell performance of the bulk heterojunction solar cell is much higher.

EXAMPLE 8

Manufacture of the Semiconducting Compound of the Formula 22

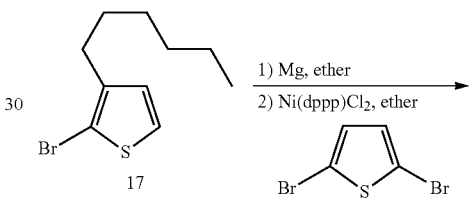

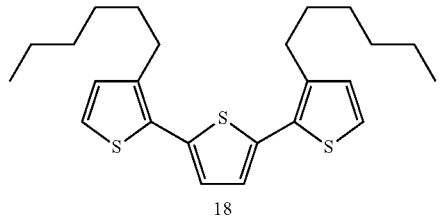

a) In a reactor 6.6 g of freshly activated magnesium turnings are suspended in 250 ml diethyl ether. 50.0 g of compound 17 are added carefully. The mixture is stirred first for 2 hours at room temperature then refluxed overnight.

Into a second reactor 0.46 g of Ni(dppp)Cl$_2$ and 20.4 g 2,5-dibromothiophene are suspended in 250 ml ether and cooled to 15° C. To this suspension the freshly prepared Grignard solution of 17 is added drop wise at such a rate to maintain 20° C. The obtained dark mixture is thereafter stirred at room temperature over night. The reaction is quenched by the addition of 10% HCl. After completion the mixture is washed with water, dried and concentrated. The compound is purified by distillation followed by column chromatography on silica gel affording 29.9 g of compound 18 as slightly yellow oil.

$^1$H-NMR data (ppm, CDCl$_3$): 7.17 2H d, 7.05 2H s, 6.93 2H d, 2.78 4H t, 1.65 4H quint, 1.27-1.40 12H m, 0.88 6H t.

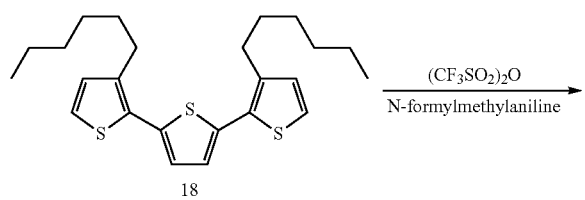

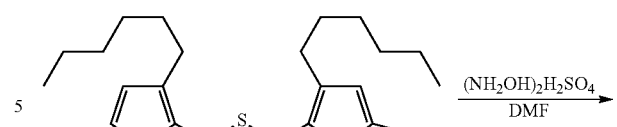

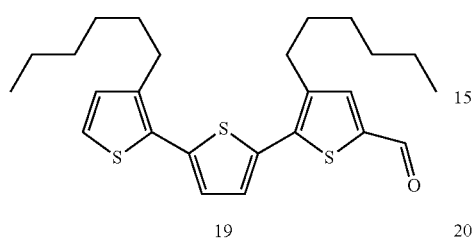

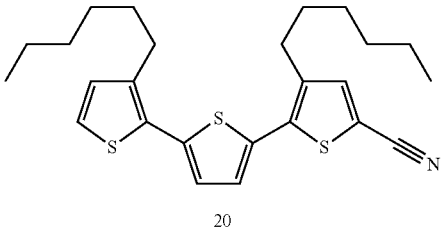

b) To a solution of 9.3 g N-formylmethylaniline in 150 ml toluene are added at 5° C. 19.5 g triflic anhydride, while a white precipitate forms. The reaction mixture is allowed to return to room temperature before 25.0 g of compound 18 are added, dissolved in 100 ml of toluene. The mixture is heated to 110° C. over night. After cooling to room temperature 25 ml of a 10% NaOH solution are added. The mixture is then extracted with water, dried and concentrated. Final purification is achieved by column chromatography on silica gel yielding 20.54 g of compound 19 as yellow oil. $^1$H-NMR data (ppm, CDCl$_3$): 9.83 1H s, 7.59 1H s, 7.23 1H d, 7.21 1H d, 7.10 1H d, 6.95 1H s, 2.82 2H t, 2.76 2H t, 1.60-1.74 4H m, 1.30-1.34 12H m, 0.89 3H t, 0.88 3H t.

c) A mixture of 18.5 g of aldehyde 19 and 4.1 g hydroxylamine sulfate in 100 mL of dimethyl formamide (DMF) is heated to 145° C. over night. After cooling to room temperature the mixture is diluted with diethyl ether, washed with water, dried and concentrated. The crude product is purified by filtration over a silica gel plug under reduced pressure affording 15.23 g of the desired nitrile 20 as dark oil. $^1$H-NMR data (ppm, CDCl$_3$): 7.44 1H s, 7.21 1H d, 7.14 1H d, 7.08 1H d, 6.95 1H s, 2.77 4H t, 1.59-1.69 4H m, 1.27-1.43 12H m, 0.89 3H t, 0.88 3H t.

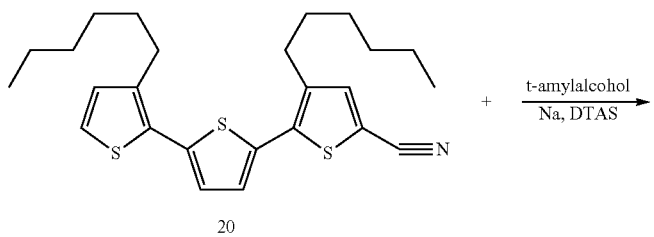

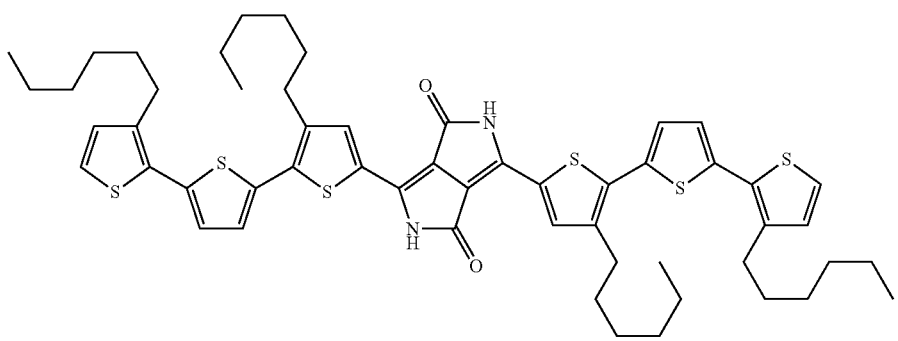

A mixture of 10 mg FeCl$_3$, 4.7 g sodium and 200 ml t-amylalcohol is heated to 110° C. for 30 minutes before a mixture of 32.0 g of nitrile 20 and 11.7 g ditertamylsuccinate (DTAS) is added drop wise. The reaction mixture is stirred at 110° C. over night before it is poured onto a water—methanol mixture. Büchner filtration and exhaustive washing with methanol affords 28.15 g of the desired DPP derivatives 21 as dark blue powder. ESI-MS m/z (% int.): 965.5 ([M+H]$^+$, 100%).

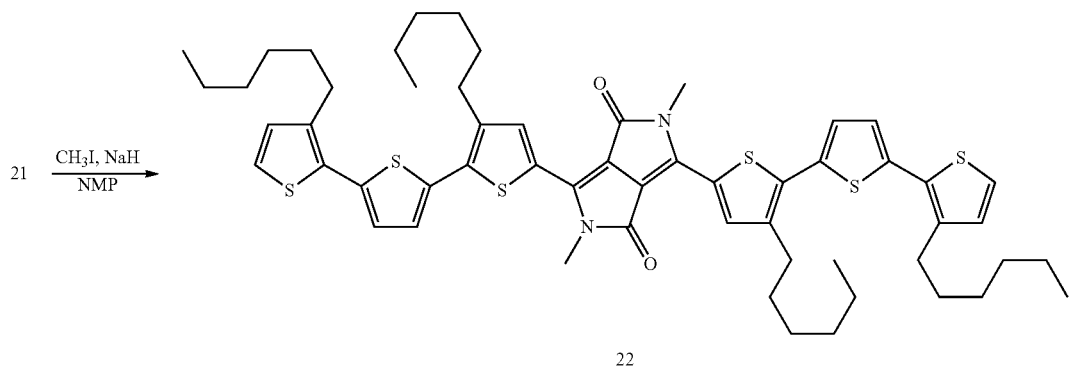

d) To 2.5 g of the 1,4-diketopyrrolo[3,4-c]pyrrole (DPP) derivative 21 in 40 ml N-methyl pyrrolidone (NMP) are added 0.3 g NaH (60% in mineral oil) at 5° C. The mixture is allowed to warm to room temperature and is stirred for 2 hours at this temperature. After cooling to 5° C. 1.1 g CH$_3$I are added. The stirring is continued over night at room temperature, then water is slowly added. The mixture is poured in dichloromethane, washed with water, concentrated and precipitated with methanol. The precipitate is collected by Büchner filtration and is washed several times with methanol to yield 2.37 g of the DPP 22 as dark blue powder. $^1$H-NMR data (ppm, CDCl$_3$): 8.89 2H s, 7.23 2H d, 7.21 2H d, 7.10 2H d, 6.95 2H d, 3.66 6H s, 2.89 4H t, 2.80 4H t, 1.64-1.83 8H m, 1.33-1.54 24H m, 0.91 6H t, 0.89 6H t.

EXAMPLE 9

Application of the Semiconducting Compound of the Formula 22

The semiconductor thin film is prepared either by spin-coating or drop casting the DPP derivative of the formula 22 obtained in example 8 in a 0.5% (w/w) solution in chloroform. The spin coating is accomplished at a spinning speed of 2000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and showed clear p-type transistor behavior. From a linear fit to the square root of the saturated transfer characteristics a field effect mobility of 9.9×10$^{-5}$ cm$^2$/Vs with an on/off current ratio of 6.0×10$^3$ can be determined. The threshold voltage is about 0 V to 2 V.

EXAMPLE 10

Manufacture of the Semiconducting Compound of the Formula 23

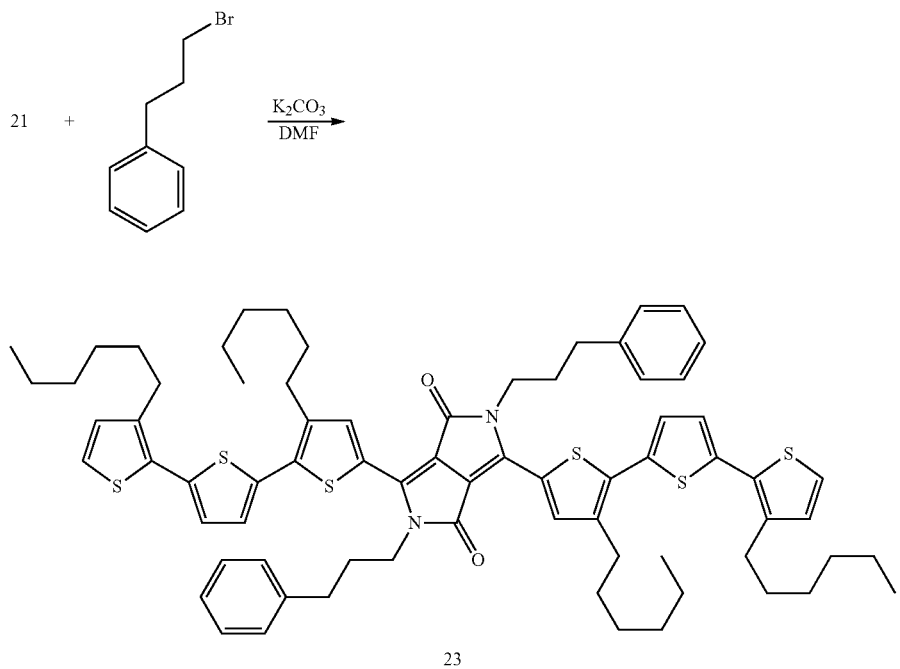

a) A mixture of 3.0 g of the 1,4-diketopyrrolo[3,4-c]pyrrole (DPP) derivative 21 and 1.7 g $K_2CO_3$ in 50 ml DMF is heated to 110° C. before 1.6 g 1-bromo-3-phenylpropane are added drop wise. The mixture is stirred over night at this temperature. After cooling to room temperature, the mixture is poured into dichloromethane, washed with water, concentrated and precipitated with methanol. The precipitate is collected by Büchner filtration and washed several times with methanol to yield 3.32 g of the DPP 23 as dark blue powder. $^1$H-NMR data (ppm, $CDCl_3$): 8.84 2H s, 7.21-7.26 10H m, 7.22 2H d, 7.15 2H d, 7.11 2H d, 6.96 2H d, 4.16 4H t, 2.77-2.90 12H m, 2.10 4H t, 1.62-1.78 8H m, 1.12-1.43 24H m, 0.90 6H t, 0.88 6H t.

EXAMPLE 11

Manufacture of the Semiconducting Compound of the Formula 24

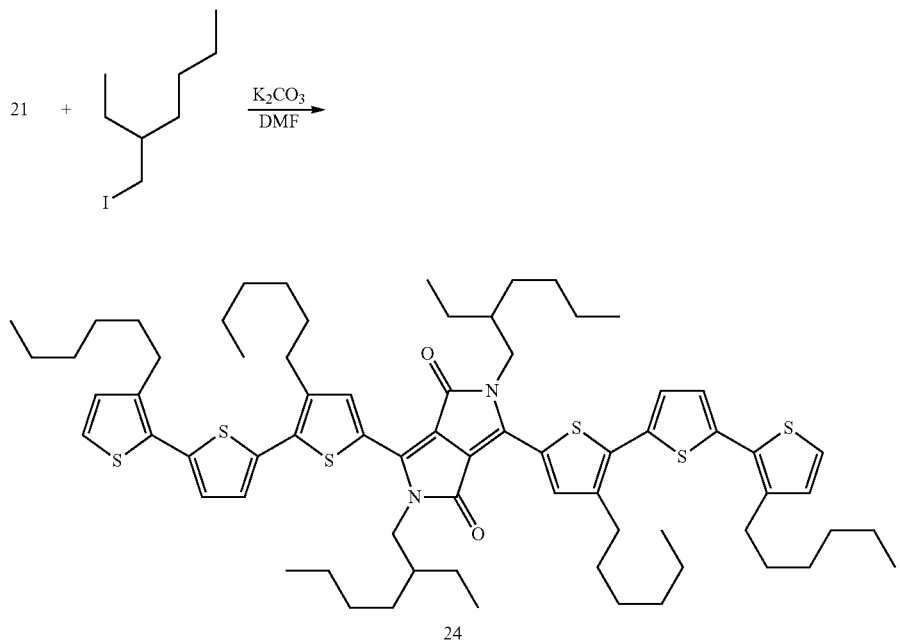

a) According to the procedure for the synthesis of compound 23, 2.0 g of the DPP 21 is reacted with 1.3 g 2-ethyl-1-hexyl iodide, 1.1 g $K_2CO_3$ in 50 ml DMF. Purification is achieved by column chromatography over silica gel and precipitation out of chloroform/methanol which affords 1.4 g of the desired DPP 24 as blue solid. $^1$H-NMR (ppm, $CDCl_3$): 8.84 2H s, 7.21 2H d, 7.20 2H d, 7.10 2H d, 6.95 2H d, 4.04 4H d, 2.89 4H t, 2.80 4H t, 1.93-1.97 2H m, 1.61-1.79 8H m, 1.28-1.34 40H m, 0.86-0.92 24H m.

EXAMPLE 12

Manufacture of the Semiconducting Compound of the Formula 25

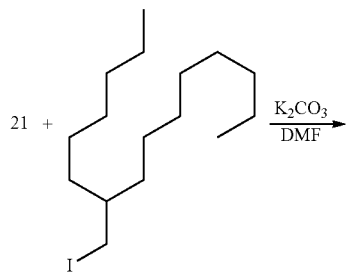

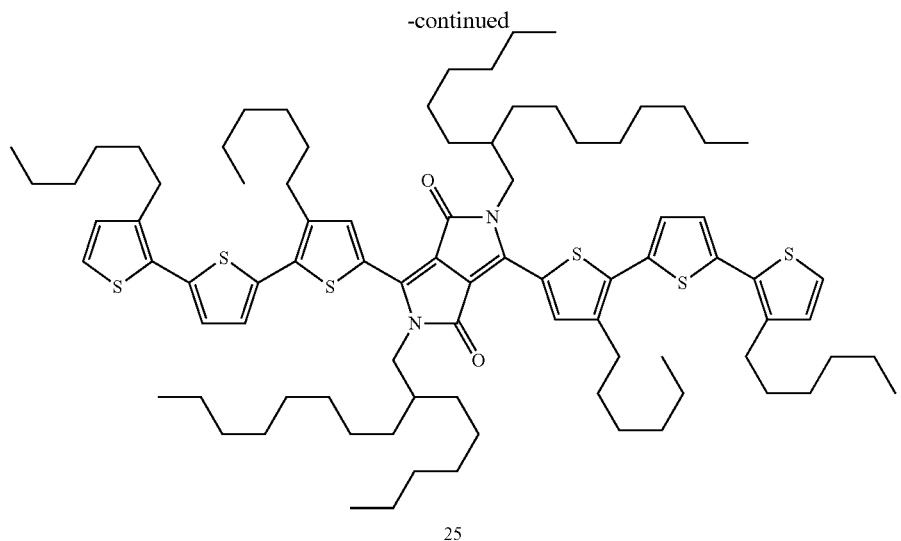

25 a) According to the procedure for the synthesis of compound 23, 2.0 g of the DPP 21 is reacted with 2.9 g 2-hexyl-1-decyl iodide, 1.1 g $K_2CO_3$ in 40 ml DMF. Purification is achieved by column chromatography over silica gel and precipitation out of chloroform/methanol which affords 2.4 g of the desired DPP 25 as blue solid.

$^1$H-NMR data (ppm, $CDCl_3$): 8.82 2H s, 7.21 2H d, 7.20 2H d, 7.10 2H d, 6.95 2H d, 4.05 4H d, 2.89 4H t, 2.80 4H t, 1.95-2.01 2H m, 1.58-1.78 8H m, 1.23-1.45 72H m, 0.86-0.92 24H m.

EXAMPLE 13

Manufacture of the Semiconducting Compound of the Formula 26

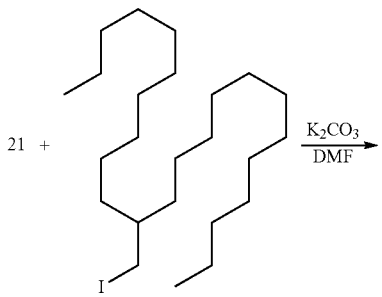

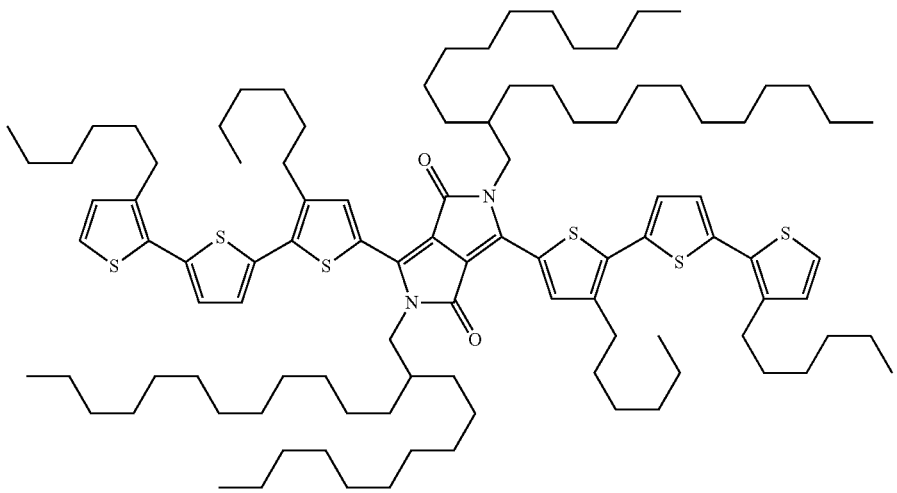

26

According to the procedure for the synthesis of compound 23, 10.0 g of the DPP 21 is reacted with 19.2 g 2-decyl-1-tetradecyl iodide, 5.7 g K$_2$CO$_3$ in 200 ml DMF. Purification is achieved by column chromatography over silica gel and precipitation out of chloroform/methanol which affords 8.6 g of the desired DPP 26. $^1$H-NMR data (ppm, CDCl$_3$): 8.84 2H s, 7.21 2H d, 7.20 2H d, 7.10 2H d, 6.95 2H d, 4.04 4H d, 2.89 4H t, 2.80 4H t, 1.93-1.97 2H m, 1.61-1.79 8H m, 1.28-1.34 104H m, 0.84-0.90 24H m.

EXAMPLE 14

Manufacture of the Semiconducting Compound of the Formula 32

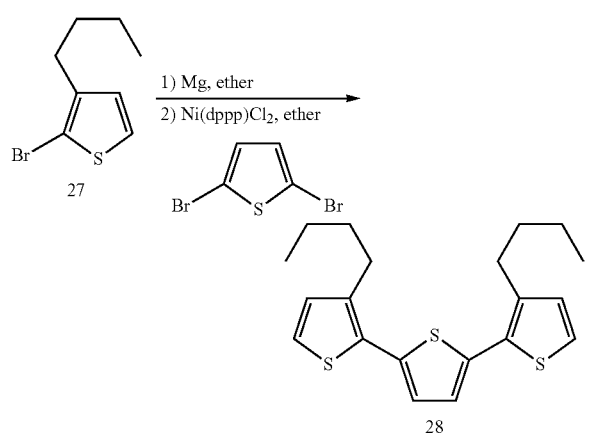

a) According to the procedure for the synthesis of compound 18, 140 g of adduct 27 was allowed to react first with 20.7 g magnesium in 300 ml diethyl ether and secondly with 1.4 g Ni(dppp) Cl$_2$ and 64.4 g 2,5-dibromothiopene in 300 ml diethyl ether. Microdestillation at reduced pressure gives 82.7 g of the desired compound 28. $^1$H-NMR data (ppm, CDCl$_3$): 7.17 2H d, 7.05 2H s, 6.93 2H d, 2.79 4H t, 1.65 4H quint, 1.40 4H sext, 0.93 6H t.

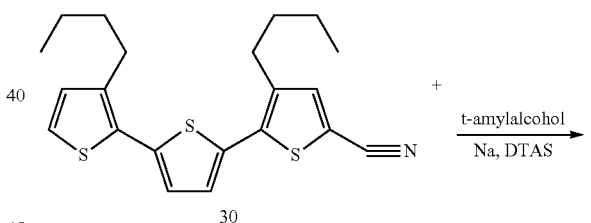

b) According to the procedure for the synthesis of 19, 60 g of the adduct 28 are reacted with 25.9 g N-formylmethylaniline, 54.0 g triflic anhydride in 500 ml toluene. Column chromatography on silica gel affords 51.3 g of the title compound 29. $^1$H-NMR data (ppm, CDCl$_3$): 9.83 1H s, 7.60 1H s, 7.24 1H d, 7.21 1H d, 7.10 1H d, 6.95 1H s, 2.84 2H t, 2.80 2H t, 1.61-1.72 4H m, 1.40-1.46 4H m, 0.97 3H t, 0.95 3H t.

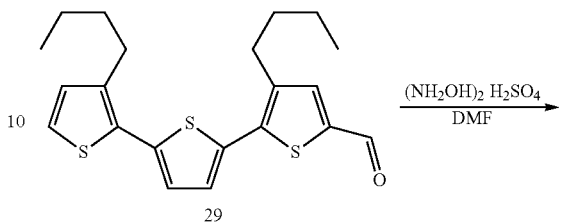

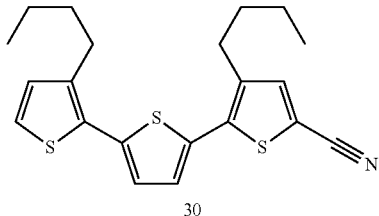

c) According to the procedure for the synthesis of 20, 60.0 g of the adduct 29 are reacted with 13.0 g hydroxylamine sulfate in 200 ml DMF. Filtration over a plug of silica gel affords 50.7 g of the desired nitril 30. $^1$H-NMR data (ppm, CDCl$_3$): 7.44 1H s, 7.21 1H d, 7.15 1H d, 7.09 1H d, 6.95 1H s, 2.78 4H t, 1.58-1.69 4H m, 1.34-1.46 4H m, 0.94 3H t, 0.93 3H t.

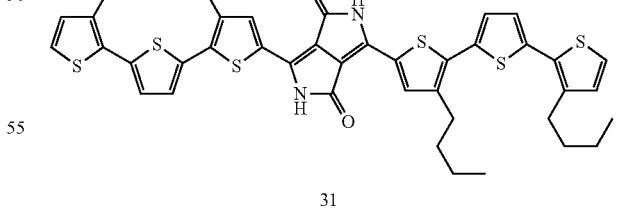

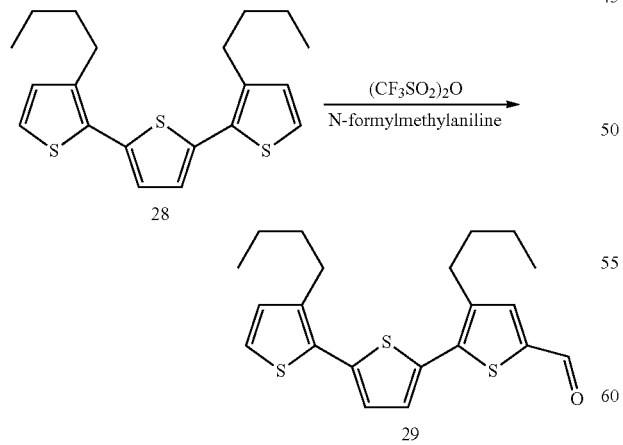

d) According to the procedure for the synthesis of 21, 50.0 g of the nitril 30 are reacted with freshly prepared sodium t-amylate (prepared from 400 ml t-amylalcohol, 8.4 g sodium and 40 mg FeCl$_3$) and 21.2 g ditertamylsuccinate. Precipitation of the crude DPP from NMP/methanol affords the desired compound 31 (47.6 g); ESI-MS m/z (% int.): 853.3 ([M+H]$^+$, 100%).

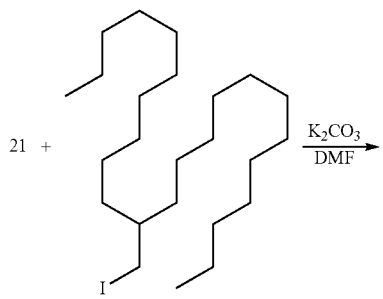

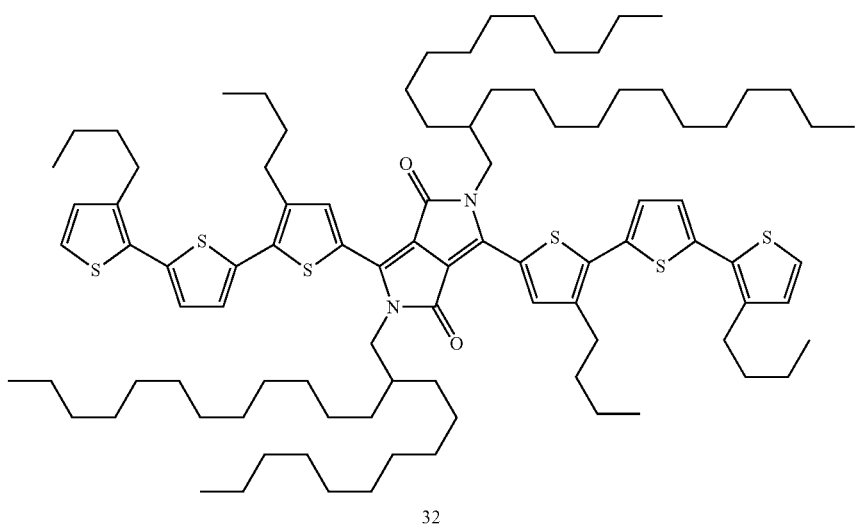

e) According to the procedure for the synthesis of compound 26, 12.5 g of the DPP 31 are reacted with 16.3 g 2-decyl-1-tetradecyl iodide and 4.5 g K$_2$CO$_3$ in 200 ml DMF. Purification is achieved by column chromatography over silica gel and precipitation from chloroform/methanol which affords 3.1 g of the desired DPP 32 as blue solid. $^1$H-NMR data (ppm, CDCl$_3$): 8.84 2H s, 7.21 2H d, 7.20 2H d, 7.10 2H d, 6.95 2H d, 4.04 4H d, 2.90 4H t, 2.81 4H t, 1.99-2.01 2H m, 1.62-1.78 8H m, 1.30-1.41 88H m, 0.84-1.00 24H m.

EXAMPLE 15

Manufacture of the Semiconducting Compound of the Formula 38

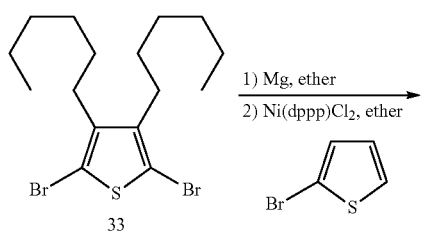

-continued

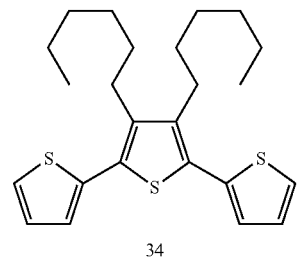

a) In a reactor 13.6 g of 2-bromothiophene is reacted with 2.4 g magnesium in 100 ml diethyl ether. The mixture is stirred first for 3 hours at room temperature then refluxed overnight to give the Grignard solution. Into a second reactor 1.4 g Ni(dppp)Cl$_2$ [dppp=propane-1,3-diylbis(diphenylphosphane)] and 14.3 g of adduct 33 are suspended in 100 ml diethyl ether and cooled to 15° C. To this suspension the freshly prepared Grignard solution is added drop wise at such a rate to keep the mixture below 20° C. The obtained dark mixture is thereafter stirred at room temperature over night. The reaction is quenched by the addition of 10% HCl. After completion the mixture is washed with water, dried and concentrated.

Column chromatography purification gave 7.01 g of the desired compound 34. $^1$H-NMR data (ppm, CDCl$_3$): 7.32 2H dd, 7.14 2H dd, 7.08 2H dd, 2.72 4H t, 1.56 4H quint, 1.30-1.45 12H m, 0.92 6H t.

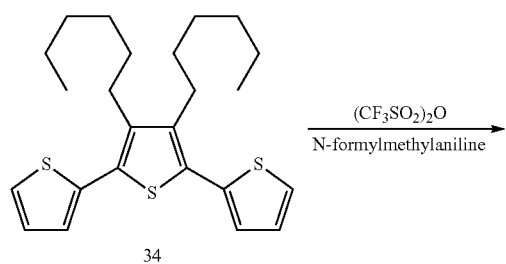

34

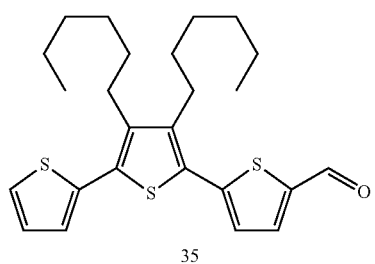

35 b) According to the procedure for the synthesis of 19, 7.0 g of the adduct 34 is allowed to react with 2.6 g N-formylmethylaniline and 5.5 g triflic anhydride in 75 ml toluene. Filtration over a silica gel plug affords 6.2 g of the desired aldehyd 35. $^1$H-NMR data (ppm, CDCl$_3$): 9.88 1H s, 7.70 1H d, 7.34 1H dd, 7.20 1H d, 7.19 1H dd, 7.08 1H dd, 2.77 2H t, 2.70 2H t, 1.53-1.58 4H m, 1.28-1.42 12H m, 0.90 3H t, 0.89 3H t;

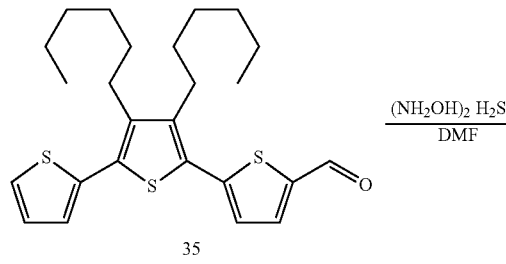

35

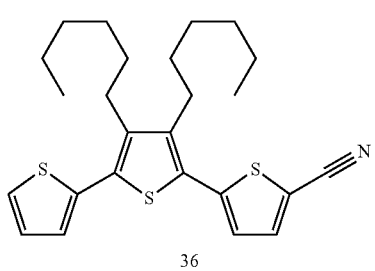

36 c) According to the procedure for the synthesis of 20, 6.0 g of the aldehyd 35 is allowed to react with 1.12 g hydroxylamine sulfate in 75 ml DMF. Column chromatography affords 4.9 g of the desired nitrile 36. $^1$H-NMR data (ppm, CDCl$_3$): 7.57 1H d, 7.35 1H dd, 7.15 1H dd, 7.09 1H dd, 7.07 1H d, 2.70 2H t, 2.69 2H t, 1.49-1.57 4H m, 1.28-1.43 12H m, 0.91 3H t, 0.89 3H t.

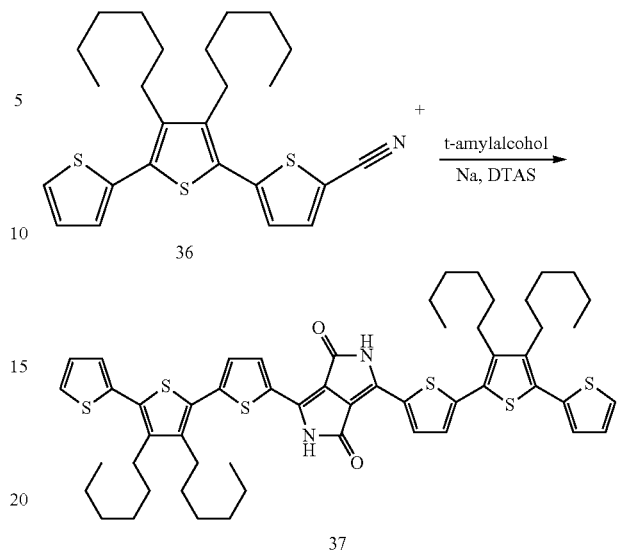

36

37 d) According to the procedure for the synthesis of 21, 4.8 g of the nitril 36 is allowed to react with freshly prepared sodium t-amylate (75 ml t-amylate, 0.7 g sodium and 5 mg FeCl$_3$) and 1.8 g ditertamylsuccinate. Precipitation from NMP and acetone affords 2.9 g of the desired DPP 37. ESI-MS m/z (% int.): 965.4 ([M+H]$^+$, 100%);

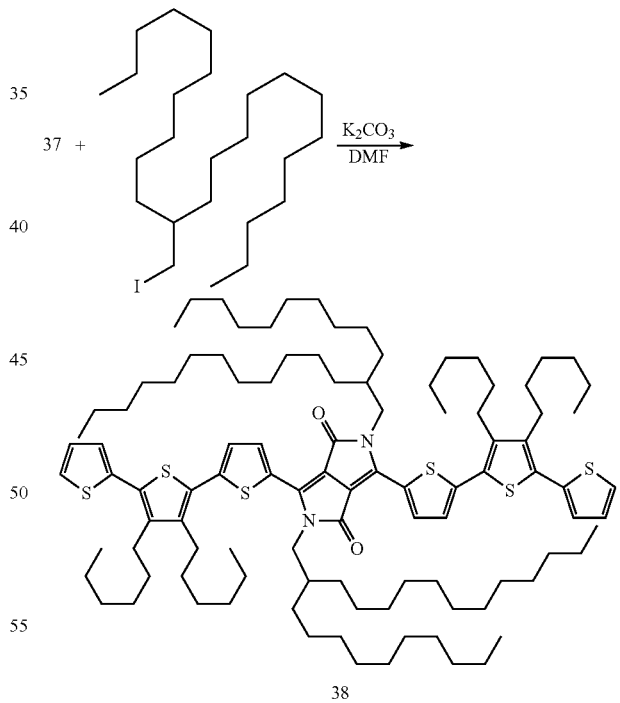

38 e) According to the procedure for the synthesis of 26, 2.8 g of the DPP 37 is allowed to react with 4.1 g 2-decyl-1-tetradecyl iodide and 1.3 g K$_2$CO$_3$ in 100 ml DMF. Precipitation from dichloromethane and methanol affords 2.8 g of the desired DPP 38. $^1$H-NMR data (ppm, CDCl$_3$): 9.03 2H d, 7.34 2H dd, 7.28 2H d, 7.17 2H dd, 7.08 2H dd, 4.06 4H d, 2.78 4H t, 2.71 4H t, 1.94-2.16 2H m, 1.23-1.61 112H m, 0.81-0.93 24H m.

EXAMPLE 16

Manufacture of the Semiconducting Compound of the Formula 44

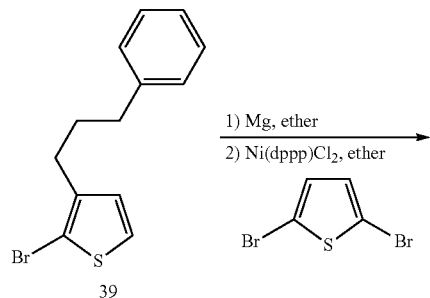

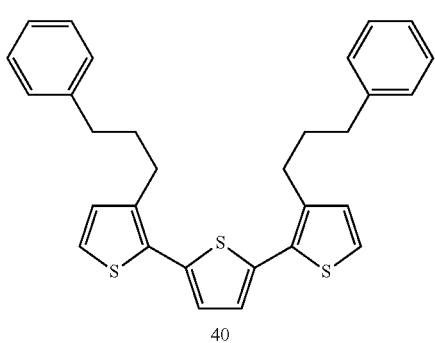

a) According to the procedure for the synthesis of compound 18, 40.0 g of adduct 39 are reacted first with 4.6 g magnesium in 200 ml diethyl ether and secondly with 0.3 g Ni(dppp)Cl₂ and 14.3 g 2,5-dibromothiopene in 200 ml diethyl ether. Filtration over silica gel gives 18.3 g of the desired compound 40. ¹H-NMR data (ppm, CDCl₃): 7.15-7.27 12H m, 6.96 2H s, 6.94 2H d, 2.82 4H t, 2.68 4H t, 1.99 4H quint.

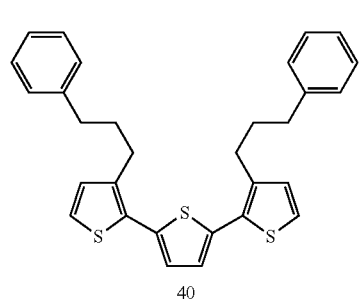

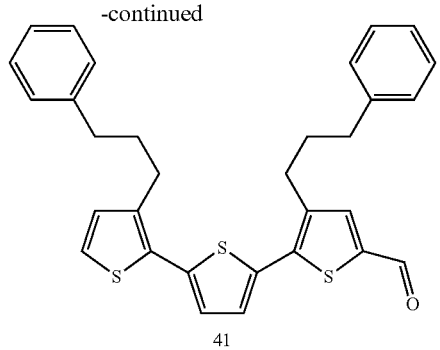

b) According to the procedure for the synthesis of 19, 18.2 g of the adduct 40 are reacted with 25.8 g N-formylmethylaniline and 12.2 g triflic anhydride in 150 ml toluene. Column chromatography on silica gel affords 16.2 g of the title compound 41. ¹H-NMR data (ppm, CDCl₃): 9.83 1H s, 7.59 1H s, 7.14-7.28 11H m, 7.12 1H d, 6.99 1H d, 6.98 1H d, 2.80-2.88 4H m, 2.66-2.74 4H m, 1.96-2.08 4H m.

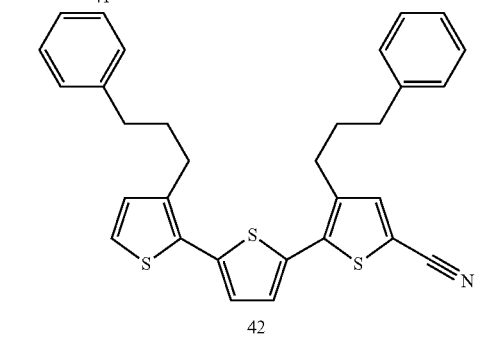

c) According to the procedure for the synthesis of 20, 16.2 g of the adduct 41 are reacted with 3.1 g hydroxylamine sulfate in 100 ml DMF. Column chromatography affords 10.0 g of the desired nitril 42; ¹H-NMR (ppm, CDCl₃): 7.43 1H s, 7.14-7.28 11H m, 7.04 1H d, 6.97 1H d, 6.95 1H d, 2.77-2.84 4H m, 2.67 4H t, 1.94-2.04 4H m.

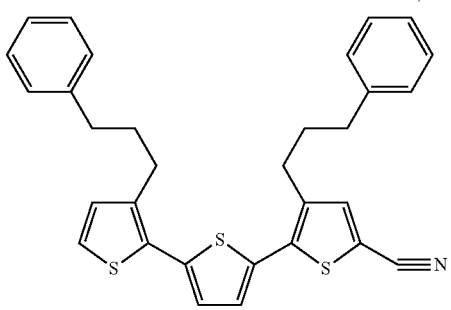

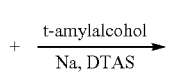

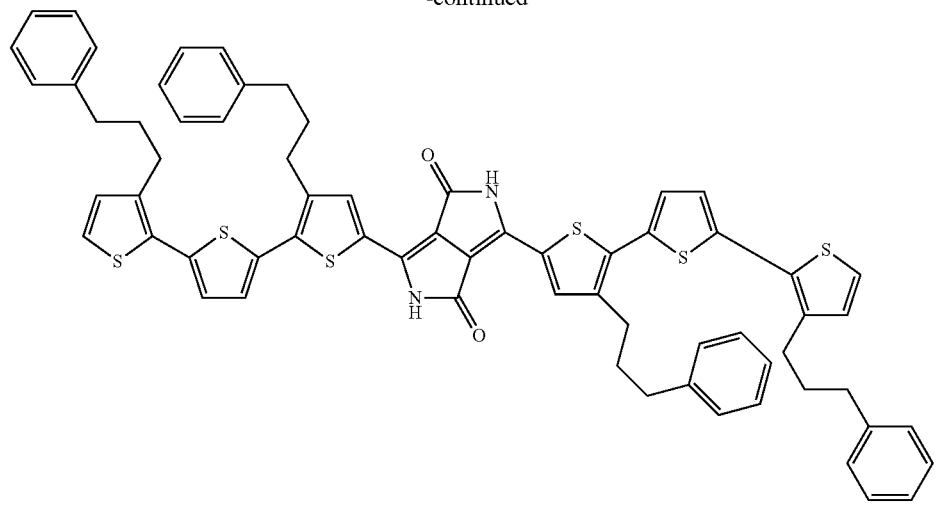

43 d) According to the procedure for the synthesis of 21, 9.9 g of the nitril 42 are reacted with freshly prepared sodium t-amylate (100 ml t-amylalcohol, 1.3 g sodium and 10 mg FeCl$_3$) and 3.2 g ditertamylsuccinate. Precipitation of the crude DPP from NMP/acetone affords the desired DPP 43 (7.2 g); ESI-MS m/z (% int.): 1101.3 ([M+H]$^+$, 100%).

e) According to the procedure for the synthesis of 25, 3.5 g of the DPP 43 are reacted with 4.5 g 2-hexyl-1-decyl iodide, 1.8 g K$_2$CO$_3$ in 120 ml DMF. Purification is achieved by precipitation from dichloromethane and methanol which affords 3.6 g of the desired DPP 44. $^1$H-NMR (ppm, CDCl$_3$): 8.88 2H s, 7.15-7.28 22H m, 7.07 2H d, 6.98 2H d, 6.96 2H d, 4.04 4H d, 2.93 4H t, 2.84 4H t, 2.76 4H t, 2.69 4H t, 1.94-2.16 8H m, 1.52-1.56 2H m, 1.22-1.34 48H m, 0.81-0.84 12H m.

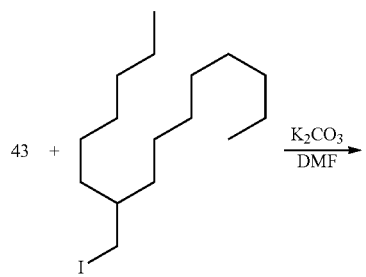

43 + → $\xrightarrow{\text{K}_2\text{CO}_3}{\text{DMF}}$

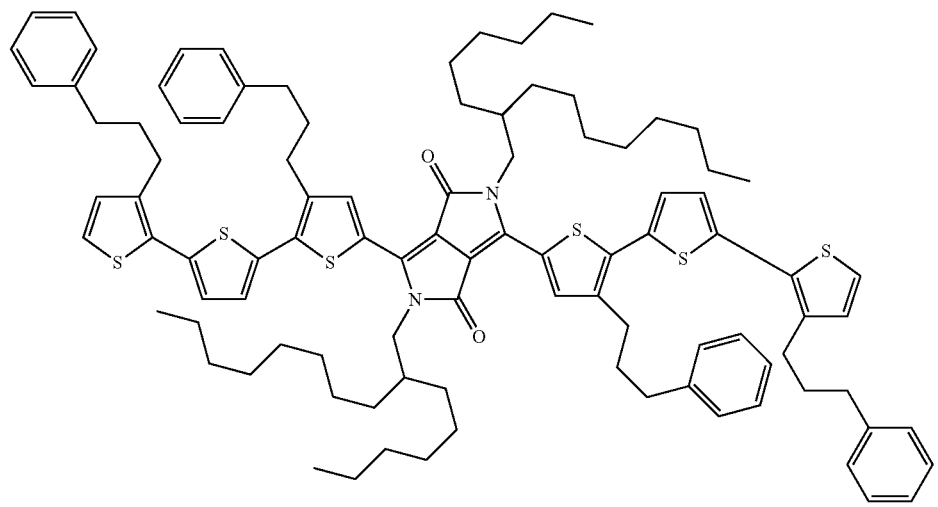

44

EXAMPLE 17

Manufacture of the Semiconducting Compound of the Formula 45

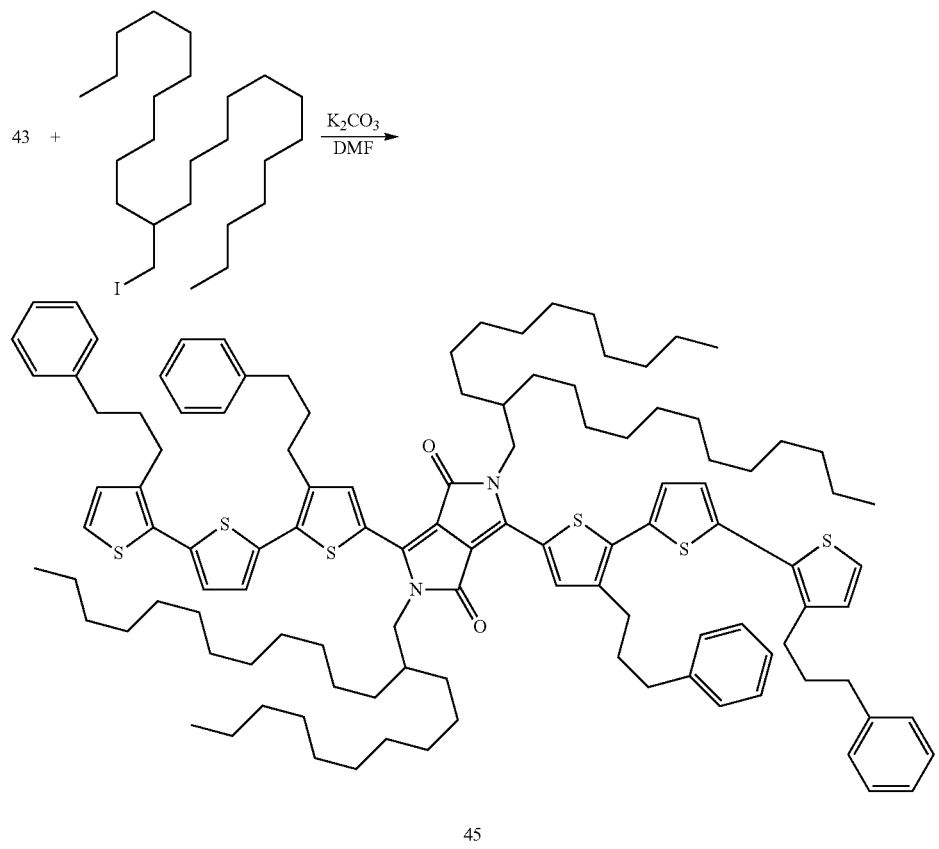

45 a) According to the procedure for the synthesis of 26, 3.5 g of the DPP 43 are reacted with 5.9 g 2-decyl-1-tetradecyl iodide and 1.8 g $K_2CO_3$ in 120 ml DMF. Purification is achieved by precipitation from dichloromethane and methanol which affords 3.1 g of the desired DPP 45. $^1$H-NMR (ppm, $CDCl_3$): 8.89 2H s, 7.15-7.27 22H m, 7.07 2H d, 6.98 2H d, 6.96 2H d, 4.04 4H d, 2.93 4H t, 2.84 4H t, 2.76 4H t, 2.69 4H t, 1.96-2.15 8H m, 1.52-1.56 2H m, 1.20-1.34 80H m, 0.83-0.87 12H m.

EXAMPLE 18

Manufacture of the Semiconducting Compound of the Formula 50

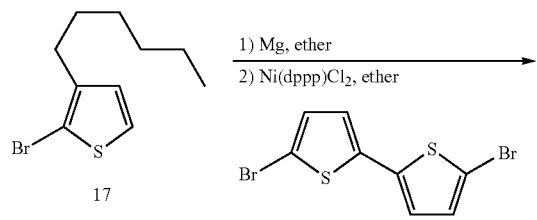

17

-continued

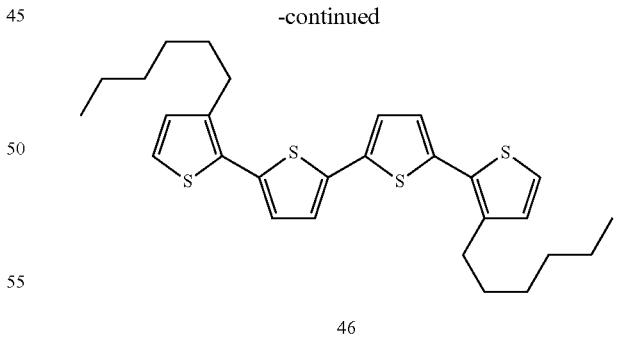

46 a) According to the procedure for the synthesis of 18, 18.3 g of adduct 17 is allowed to react first with 2.4 g magnesium in 100 ml diethyl ether and secondly with 0.2 g Ni(dppp)Cl$_2$, 10.0 g 5,5'-dibromo-2,2'-bithiophene in 100 ml diethyl ether. Column chromatography gives 15.1 g of the desired compound 46. $^1$H-NMR (ppm, $CDCl_3$): 7.17 2H d, 7.11 2H d, 7.01 2H d, 6.93 2H d, 2.78 4H t, 1.67 4H quint, 1.29-1.35 12H m, 0.89 6H t.

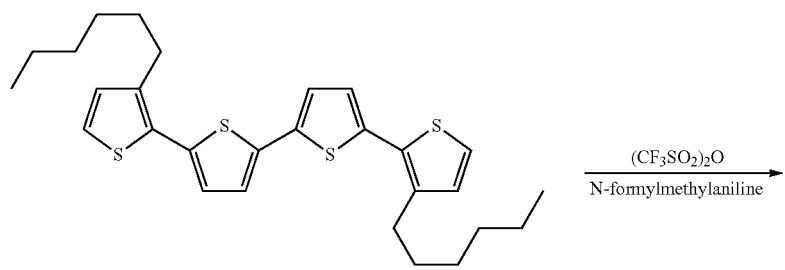

46

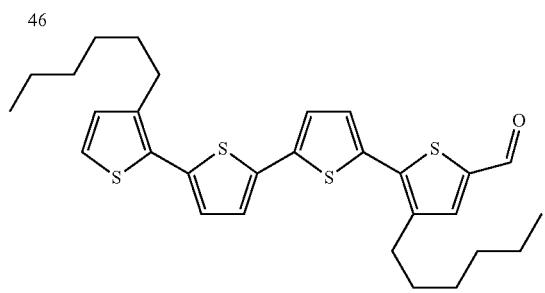

47 b) According to the procedure for the synthesis of 19, 15.0 g of the adduct 46 are reacted with 4.7 g N-formylmethylaniline and 9.8 g triflic anhydride in 100 ml toluene. Column chromatography on silica gel affords 9.1 g of compound 47. $^1$H-NMR (ppm, CDCl$_3$): 9.83 1H s, 7.59 1H s, 7.15-7.25 4H m, 7.03 1H d, 6.95 1H d, 2.82 2H t, 2.78 2H t, 1.54-1.72 4H m, 1.25-1.41 12H m, 0.90 3H t, 0.89 3H t.

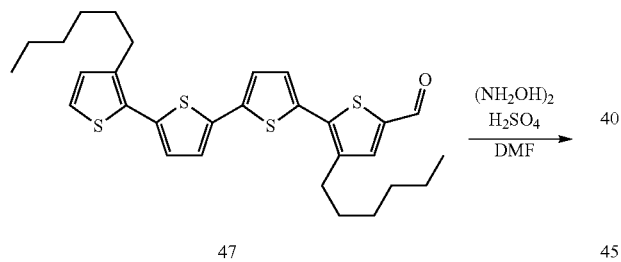

47

-continued

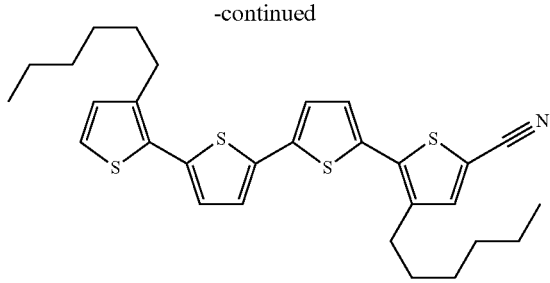

48 c) According to the procedure for the synthesis of 20, 9.1 g of the adduct 47 is reacted with 1.7 g hydroxylamine sulfate in 100 ml DMF. Column chromatography affords 4.9 g of the desired nitril 48. $^1$H-NMR data (ppm, CDCl$_3$): 7.44 1H s, 7.11-7.20 4H m, 7.03 1H d, 6.95 1H d, 2.78 4H t, 1.54-1.67 4H m, 1.33-1.43 12H m, 0.88-0.91 6H m.

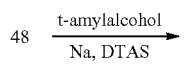

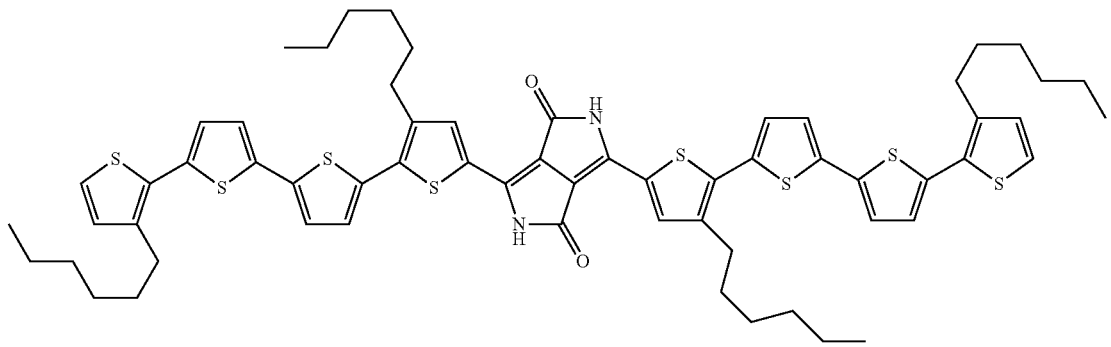

49 d) According to the procedure for the synthesis of 21, 4.8 g of the nitril 48 are reacted with freshly prepared sodium t-amylate (50 ml t-amylalcohol, 0.6 g sodium and 5 mg FeCl$_3$) and 1.5 g ditertamylsuccinate. Precipitation of the crude DPP from NMP/methanol affords the desired compound 49 (3.1 g); ESI-MS m/z (% int.): 1129.3 ([M+H]$^+$, 100%).

a) 228.06 g of 2-decyl-1-tetradecanol [58670-89-6] are mixed with 484.51 g 47% hydroiodic acid and the mixture is refluxed overnight. The product is extracted with t-butyl-methylether. Then the organic phase is dried and concentrated. The product is purified over a silica gel column to give 211.54 g of the desired compound 51 (73%). $^1$H-NMR (ppm, CDCl$_3$): 3.26 2H d, 1.26-1.12 41H m, 0.88 6H t.

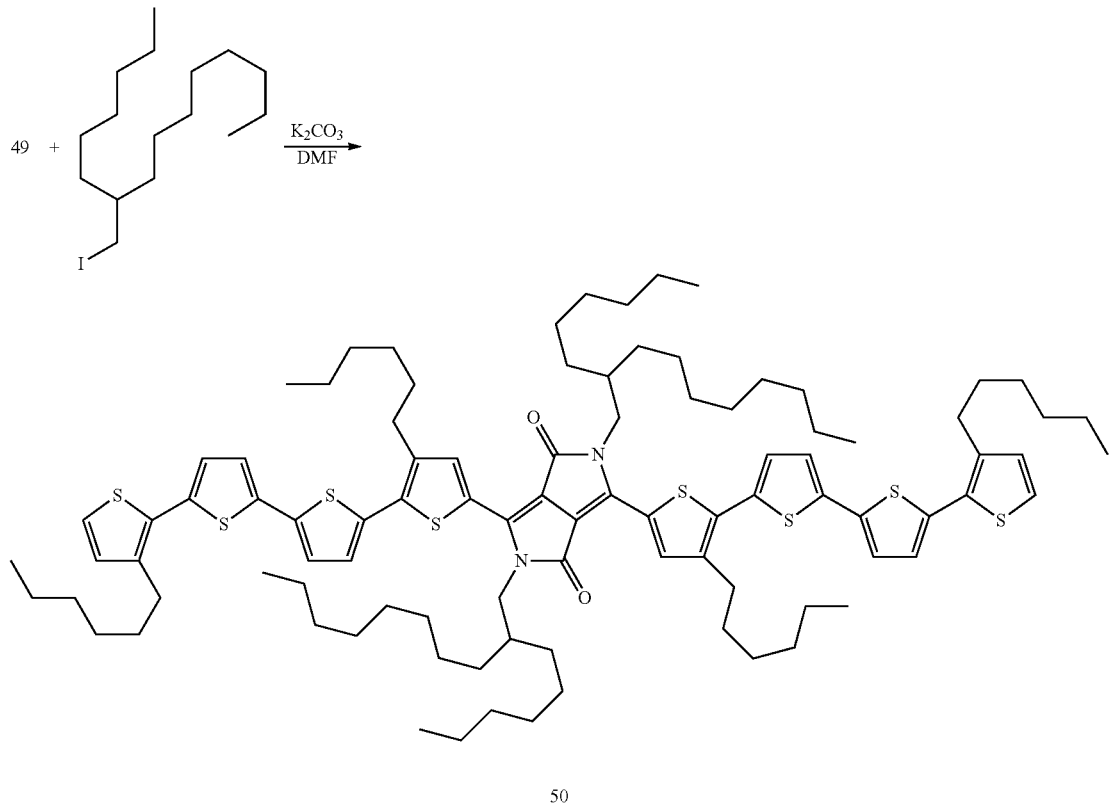

e) According to the procedure for the synthesis of 25, 3.0 g of the DPP 49 are reacted with 3.7 g 2-hexyl-1-decyl iodide and 1.5 g K$_2$CO$_3$ in 80 ml DMF. Purification is achieved by column chromatography over silica gel and precipitation from chloroform/methanol which afforded 2.9 g of the desired DPP 50. $^1$H-NMR (ppm, CDCl$_3$): 8.82 2H s, 7.14-7.21 8H m, 7.05 2H d, 6.95 2H d, 4.04 4H d, 2.88 4H t, 2.79 4H t, 1.99-2.01 2H m, 1.61-1.82 8H m, 1.24-1.42 104H m, 0.89 12H t. 0.84 12H t.

EXAMPLE 19

Manufacture of the Semiconducting Compound of the Formula 53

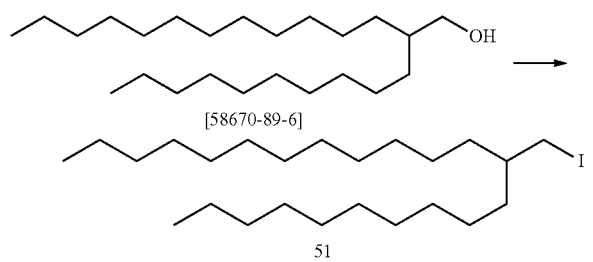

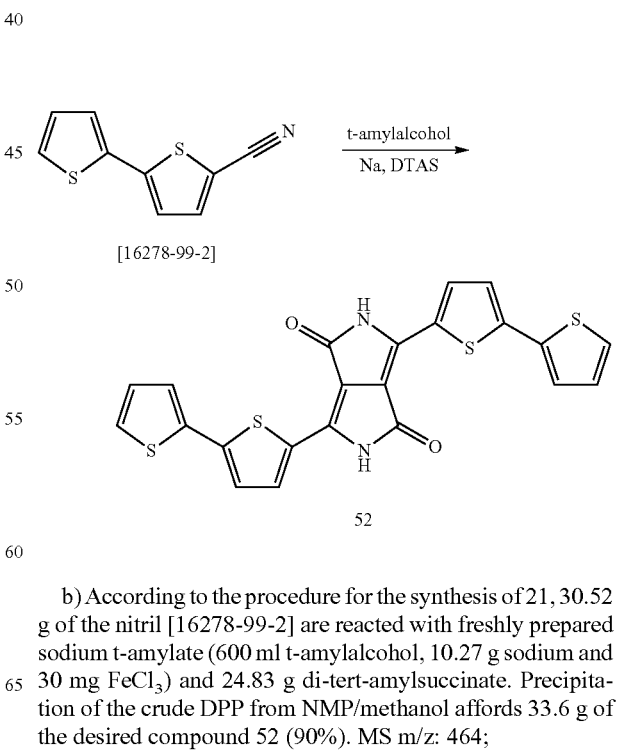

b) According to the procedure for the synthesis of 21, 30.52 g of the nitril [16278-99-2] are reacted with freshly prepared sodium t-amylate (600 ml t-amylalcohol, 10.27 g sodium and 30 mg FeCl$_3$) and 24.83 g di-tert-amylsuccinate. Precipitation of the crude DPP from NMP/methanol affords 33.6 g of the desired compound 52 (90%). MS m/z: 464;

51 + 52 ⟶

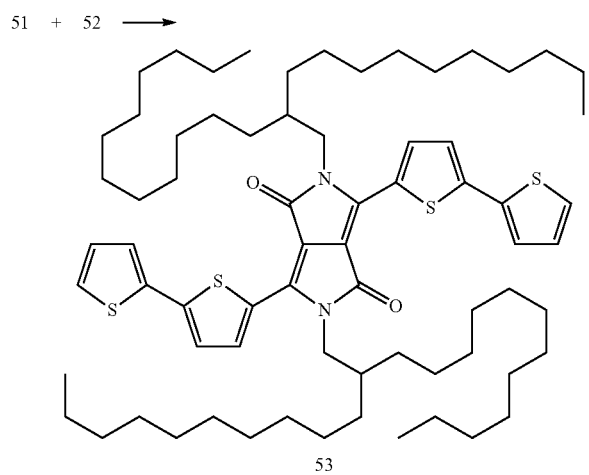

53 c) According to the procedure for the synthesis of 25, 33.55 g of the DPP 52 are reacted with 74.4 g 2-decyl-1-tetradecyl iodide, 1.27 g LiH in 1300 ml DMF. Purification is achieved by column chromatography over silica gel and affords 35.1 g of the desired DPP 53 (42.7%). $^1$H-NMR (ppm, CDCl$_3$): 8.91 2H d, 7.35-7.32 6H m, 7.09 2H dd, 4.05 4H d, 1.98 2H m, 1.35-1.20 80H m, 0.89 6H t, 0.87 6H t.

EXAMPLE 20

Manufacture of the Semiconducting Compound of the Formula 55

53 $\xrightarrow{\text{NBS}}$

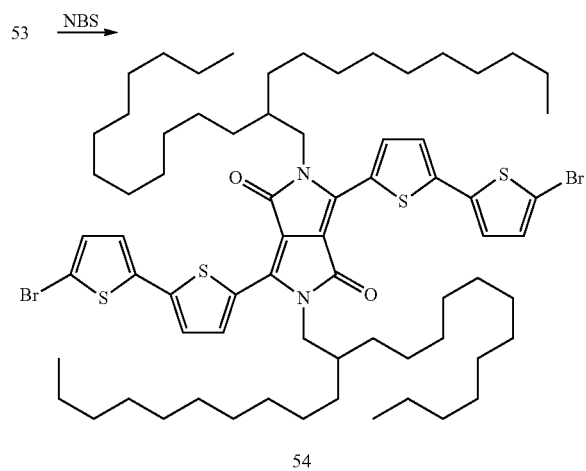

54 a) According to the procedure for the synthesis of 2, 10.00 g 53 are dissolved in 200 ml of chloroform, cooled down to 0° C. and 2 equivalents of N-bromosuccinimide (NBS) are then added portion wise over a period of 1 h. After the reaction is completed, the mixture is washed with water. The organic phase is extracted, dried and concentrated. The compound is then purified over a silica gel column to give 5.31 g of a dark violet powder of the DPP derivative of the formula 54 (47%). $^1$H-NMR data (ppm, CDCl$_3$): 8.85 2H d, 7.22 2H d, 7.03 4H dd, 4.00 4H d, 1.93 2H m, 1.29-1.21 80H m, 0.87 6H t, 0.85 6H t;

54 +

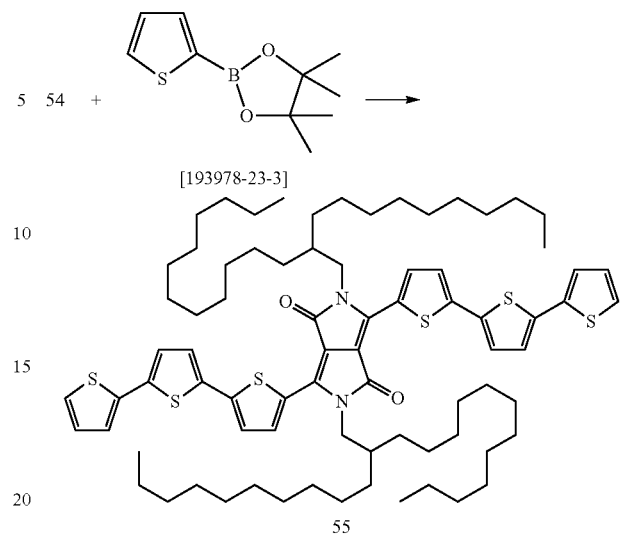

[193978-23-3]

55 b) 1 g of compound 54, 414 mg 2-thienylboronic acid pinacol ester [193978-23-3], 12 mg Pd$_2$(dba)$_3$ [Tris(dibenzylideneacetone)-di-palladium)] and 9.4 mg tri-tert-butyl-phosphonium-tetrafluoroborate are dissolved in 10 ml of tetrahydrofurane. This solution is degassed with 3 cycles of freeze/pump/thaw (Ar). 0.7 g of potassium phosphate are dissolved in 1.5 ml of water and degassed under argon. The water solution is added to the THF solution and the reaction mixture is refluxed over night. The reaction mixture is diluted with water and then extracted with methylene chloride. The organic phase is dried and evaporated. The residue is purified over silica gel and 480 mg of the desired product 55 is obtained as violet solid (50%); m.p. 150° C., $^1$H-NMR (ppm, CDCl$_3$): 8.91 2H d, 7.29 4H d, 7.21 4H d, 7.12 2H d, 7.03 2H dd, 4.04 4H d, 1.97 2H m, 1.33-1.19 80H m, 0.86 6H t, 0.84 6H t.

EXAMPLE 21

Application of the Semiconducting Compound of the Formula 55

The semiconductor thin film is prepared either by spin-coating or drop casting the DPP derivative of the formula 55 obtained in example 20 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and shows clear p-type transistor behavior. From a linear fit to the square root of the saturated transfer characteristics a field effect mobility of $1.6 \times 10^{-2}$ cm$^2$/Vs with an on/off current ratio of $1.3 \times 10^5$ is determined. The threshold voltage is about −2 V.

Electrochemical Measurements

Electrochemical data are obtained by cyclic voltammetry following exactly the same procedure as described in example 2, method B. The resulting level of the DPP derivative of formula 55 corresponds to a HOMO level of approx. −5.6 eV, respectively a LUMO (lowest unoccupied molecular orbital) level of −3.9 eV.

EXAMPLE 22

Photovoltaic Application of the Semiconducting Compound of Formula 55 DPP-Monomer Based Bulk Heterojunction Solar Cell The solar cell has the following structure: Al electrode/LiF layer/organic layer comprising compound 55 and [60] PCBM/[poly(3,4-ethylenedioxy-thiophene) (PEDOT) in admixture with poly(styrenesulfonic acid) (PSS)]/ITO electrode/glass substrate. The solar cells are made by spin coating a layer of the PEDOT-PSS on a pre-patterned ITO on glass substrate. Then a 1:1 mixture of the compound of formula 55 (1% by weight): [60]PCBM (a substituted $C_{60}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=8.3 mA/cm$^2$, FF=0.54 and $V_{oc}$=0.84 V for an estimated overall efficiency of 3.75%.

EXAMPLE 23

Manufacture of the Semiconducting Compound of the Formula 56

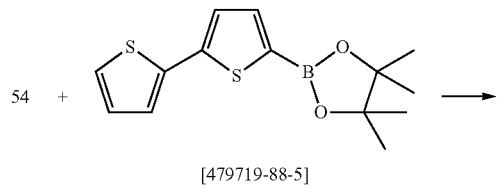

[479719-88-5]

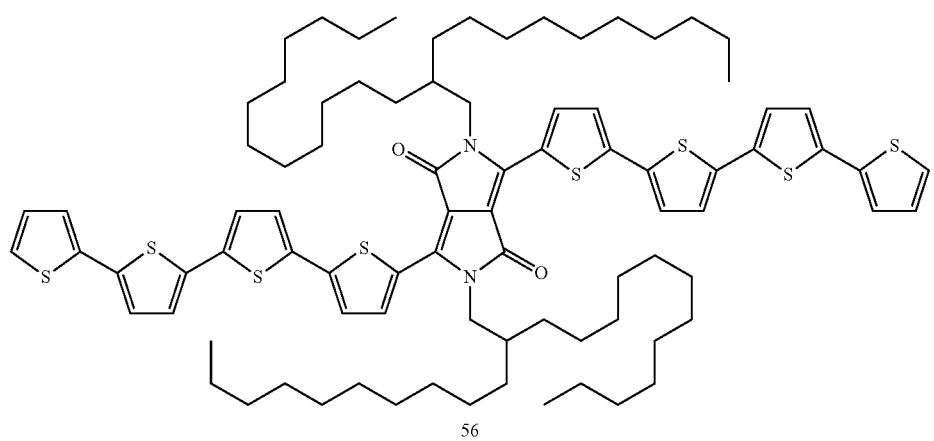

56

According to the procedure for the synthesis of compound 55, 2,2'-bithiophene-5-boronic acid pinacol ester [479719-88-5] and compound 54 have been reacted to give compound 56; m.p. 196° C.; $^1$H-NMR (ppm, CDCl$_3$): 8.87 2H d, 7.27 2H d, 7.25-7.17 6H m, 7.11-7.08 6H m, 7.02 2H dd, 4.03 4H d, 1.98 2H m, 1.34-1.18 80H m, 0.86 6H t, 0.84 6H t.

EXAMPLE 24

Application of the Semiconducting Compound of the Formula 56

The semiconductor thin film is prepared either by spin-coating or drop casting the DPP derivative of the formula 56 obtained in example 23 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and shows clear p-type transistor behavior. From a linear fit to the square root of the saturated transfer characteristics a field effect mobility of 1.9×10$^{-2}$ cm$^2$/Vs with an on/off current ratio of 3.4×10$^5$ is determined. The threshold voltage is about 0.7 V and 2 V.

Electrochemical Measurements

Electrochemical data are obtained by cyclic voltammetry following exactly the same procedure as described in example 2, method B.

The resulting level of the DPP derivative of formula 56 corresponds to a HOMO level of approx. −5.6 eV, respectively a LUMO (lowest unoccupied molecular orbital) level of −4.0 eV.

EXAMPLE 25

Photovoltaic Application of the Semiconducting Compound of Formula 56

DPP-Monomer Based Bulk Heterojunction Solar Cell

The solar cell has the following structure: Al electrode/LiF layer/organic layer, comprising compound 56 and [60]

PCBM/[poly(3,4-ethylenedioxy-thiophene) (PEDOT) in admixture with poly(styrenesulfonic acid) (PSS)]/ITO electrode/glass substrate. The solar cells are made by spin coating a layer of the PEDOT-PSS on a pre-patterned ITO on glass substrate. Then a 1:1 mixture of the compound of formula 56 (1% by weight): [60]PCBM (a substituted $C_{60}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=10.5 mA/cm$^2$, FF=0.55 and $V_{oc}$=0.76 V for an estimated overall efficiency of 4.4%.

EXAMPLE 26

Manufacture of the Semiconducting Compound of the Formula 58

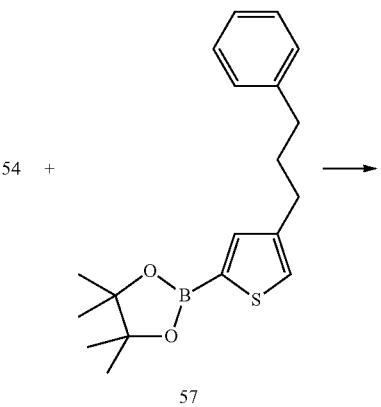

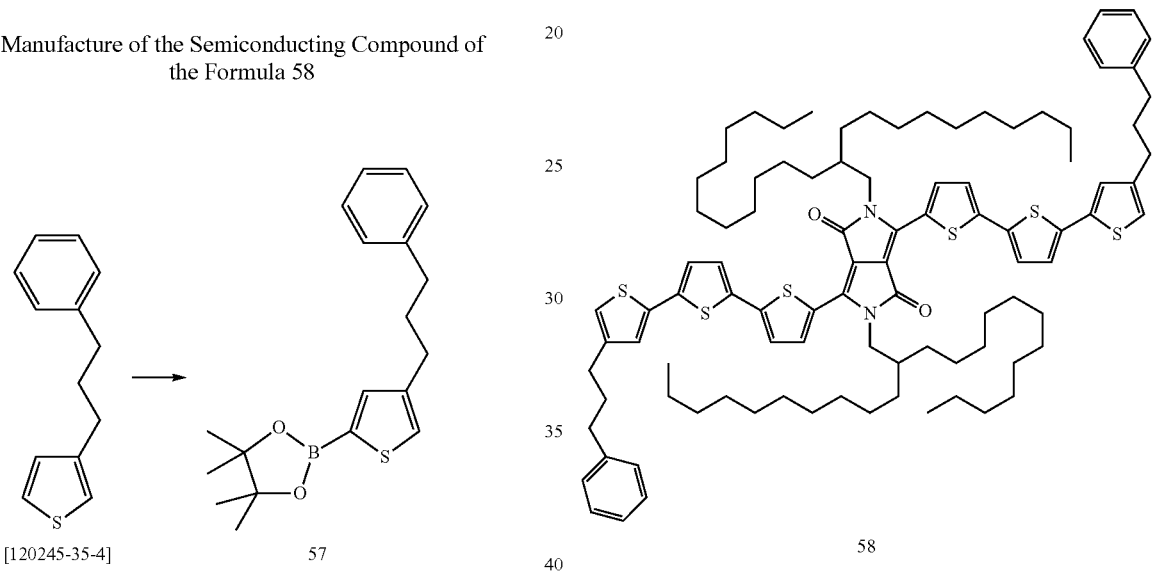

a) 370.1 ml 1.6 M n-BuLi (n-butyl lithium) is added under argon drop wise to a solution of 67.5 g diisopropylamine in 550 ml THF at −78° C. After stirring at −78° C. for 30 minutes the mixture is allowed to reach 0° C. where the stirring is continued for 2 hours, then the mixture is cooled to −78° C. 100.0 g 3-phenylpropylthiophene [120245-35-4] are then added drop wise and after 2 hours stirring 115.0 g 2-isopropoxy-4,4,5,5-tetramethyl-1,3,2-dioxaborolane [61676-62-8] are added dropwise. The reaction mixture is stirred at −78° C. for additional 30 minutes and is then gradually warmed to room temperature and stirred overnight. The solution is poured on 750 ml 1N HCl. The organic part is extracted with 900 ml ethyl acetate and is washed with 300 ml water. The organic layer is dried over $Na_2SO_4$ and the solvents are removed under reduced pressure. Column chromatography over silica gel gives 130.4 g of the desired compound 57: $^1$H-NMR (ppm, CDCl$_3$): 7.48 1H s, 7.30-7.26 2H m, 7.23 1H s, 7.20-7.16 3H m, 2.67 2H t, 2.64 2H t, 1.96 2H quint, 1.34 12H s.

b) According to the procedure for thesynthesis of compound 55, 4-(phenylpropyl)-thiophene-2-boronic acid pinacol ester 57 and compound 54 are reacted to give compound 58: $^1$H-NMR (ppm, CDCl$_3$): 8.91 2H d, 7.32-7.17 14H m, 7.06 2H d, 7.03 2H s, 6.85 2H s, 4.03 4H d, 2.68 4H t, 2.63 4H t, 2.03-1.93 6H m, 1.33-1.19 80H m, 0.85 6H t, 0.83 6H t.

EXAMPLE 27

Application of the Semiconducting Compound of the Formula 58

The semiconductor thin film is prepared either by spin-coating or drop casting the DPP derivative of the formula 58 obtained in example 26 in a 0.5% (w/w) solution in chloroform. The spin coating is accomplished at a spinning speed of 3000 rpm (rounds per minute) for about 20 seconds in ambient conditions. The devices are evaluated as deposited.

Transistor Performance

The transistor behavior is measured on an automated transistor prober (TP-10, CSEM Zürich) and showed clear p-type transistor behavior. From a linear fit to the square root of the saturated transfer characteristics a field effect mobility of $1.1 \times 10^{-4}$ cm$^2$/Vs with an on/off current ratio of $1.7 \times 10^4$ can be determined. The threshold voltage is about −5 V and −3 V.

EXAMPLE 28

Manufacture of the Semiconducting Compound of the Formula 59

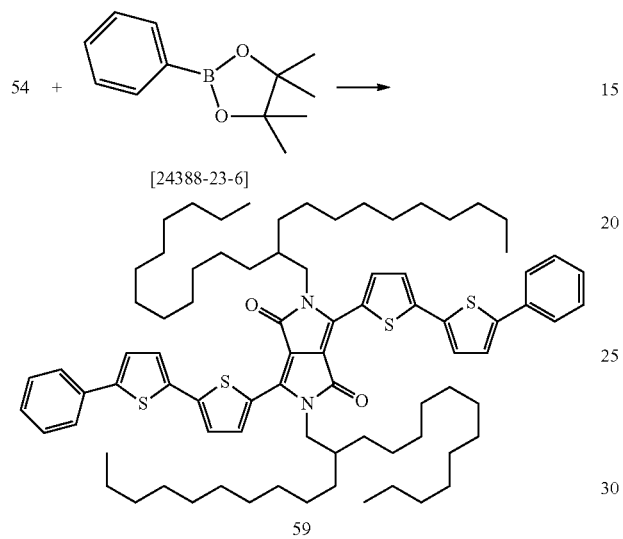

According to the procedure for the synthesis of compound 55, phenyl-boronic acid pinacol ester [24388-23-6] and compound 54 are reacted to give compound 59; m.p. 158° C.; $^1$H-NMR data (ppm, CDCl$_3$): 8.93 2H d, 7.61 4H d, 7.40 4H t, 7.33-7.26 8H m, 4.04 4H d, 1.98 2H m, 1.33-1.19 80H m, 0.87 6H t, 0.85 6H t.

EXAMPLE 28A

Application of the Semiconducting Compound of the Formula 59

The semiconductor thin film is prepared either by spin-coating or drop casting the DPP derivative of the formula 59 obtained in example 28 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and showed clear p-type transistor behavior. From a linear fit to the square root of the saturated transfer characteristics a field effect mobility of $5.2 \times 10^{-3}$ cm$^2$/Vs with an on/off current ratio of $1.2 \times 10^5$ can be determined. The threshold voltage is of about −3 V.

EXAMPLE 29

Manufacture of the Semiconducting Compound of the Formula 60

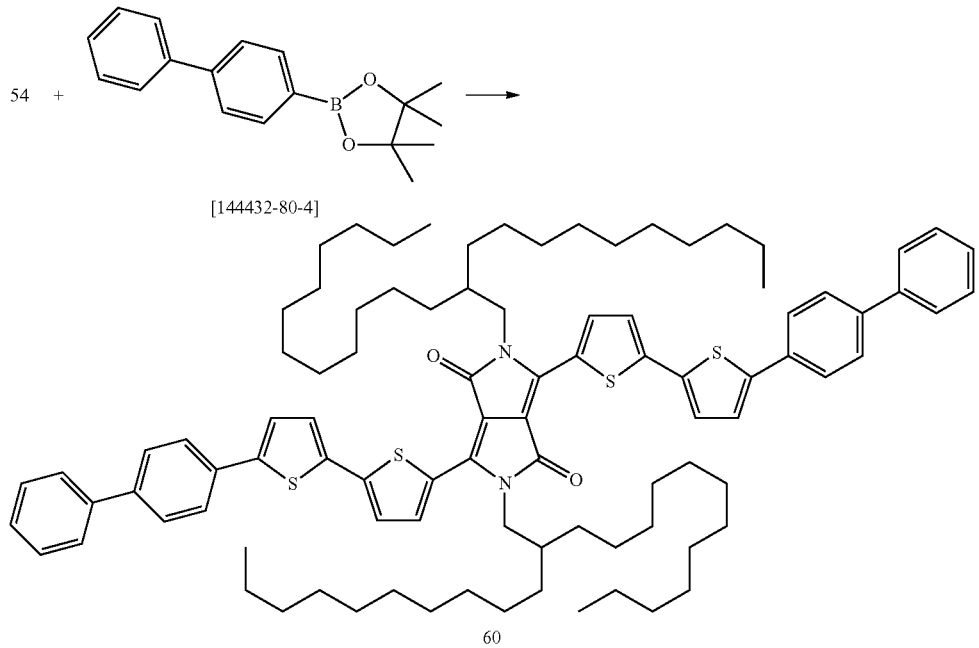

According to the procedure for the synthesis of compound 55, 4-biphenyl-boronic acid pinacol ester [144432-80-4] and compound 54 are reacted to give compound 60; m.p. 230° C.; $^1$H-NMR (ppm, CDCl$_3$): 8.89 2H d, 7.67 4H d, 7.66-7.60 4H m, 7.43 4H dd, 7.36-7.29 4H m, 7.24 4H s, 4.04 4H d, 1.99 2H m, 1.35-1.19 80H m, 0.85 6H t, 0.83 6H t.

EXAMPLE 29A

Application of the Semiconducting Compound of the Formula 60

The semiconductor thin film is prepared either by spin-coating or drop casting the DPP derivative of the formula 60 obtained in example 29 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.
Transistor Performance
The transistor behavior is measured on an automated transistor prober (TP-10, CSEM Zürich) and showed clear p-type transistor behavior. From a linear fit to the square root of the saturated transfer characteristics a field effect mobility of $1.3 \times 10^{-2}$ cm$^2$/Vs with an on/off current ratio of $2.0 \times 10^5$ can be determined. The threshold voltage is of about −6 V to −1.5 V.
Solar Cell Performance of the Bulk Heterojunction Solar Cell
The bulk heterojunction solar cell described in Example 7 wherein the compound of the formula 16 is replaced by compound 60 is measured under a solar light simulator. Then with the External Quantum Efficiency (EQE) graph the current is estimated under AM1.5 conditions. This leads to a value of $J_{sc}$=4.8 mA/cm$^2$, FF=0.59, $V_{oc}$=0.80 V and an overall efficiency of about 2.2%.

EXAMPLE 30

Manufacture of the Semiconducting Compound of the Formula 61

According to the procedure for the synthesis of compound 55, 5'-hexyl-2,2'-bithiophene-5-boronic acid pinacol ester [579503-59-6] and compound 54 are reacted to give compound 61; m.p. 135° C.; $^1$H-NMR (ppm, CDCl$_3$): 8.93 2H d, 7.25 2H d, 7.16 2H d, 7.04 4H dd, 6.97 4H dd, 6.67 2H d, 4.01 4H d, 2.79 4H t, 1.96 2H m, 1.67 4H txt, 1.34-1.18 92H m, 0.90 6H t, 0.86 6H t, 0.85 6H t.

EXAMPLE 31

Application of the Semiconducting Compound of the Formula 61

The semiconductor thin film is prepared either by spin-coating or drop casting the DPP derivative of the formula 61 obtained in example 30 in a 0.5% (w/w) solution in chloroform. The spin coating is accomplished at a spinning speed of 3000 rpm (rounds per minute) for about 20 seconds in ambient conditions. The devices are evaluated as deposited.
Transistor Performance
The transistor behavior is measured on an automated transistor prober (TP-10, CSEM Zürich) and shows clear p-type transistor behavior. From a linear fit to the square root of the saturated transfer characteristics a field effect mobility of 3.4×10−3 cm2/Vs with an on/off current ratio of 6.4×104 is determined. The threshold voltage is about −0.5 V to 2 V.

EXAMPLE 32

Photovoltaic Application of the Semiconducting Compound of Formula 61

DPP-Monomer Based Bulk Heterojunction Solar Cell
The solar cell has the following structure: Al electrode/LiF layer/organic layer, including the compound of the formula 61 and the fullerene [60]PCBM/poly(3,4-ethylenedioxy-thiophene) (PEDOT) in admixture with poly(styrenesulfonic acid) (PSS)]/ITO electrode/glass substrate. The solar cells are

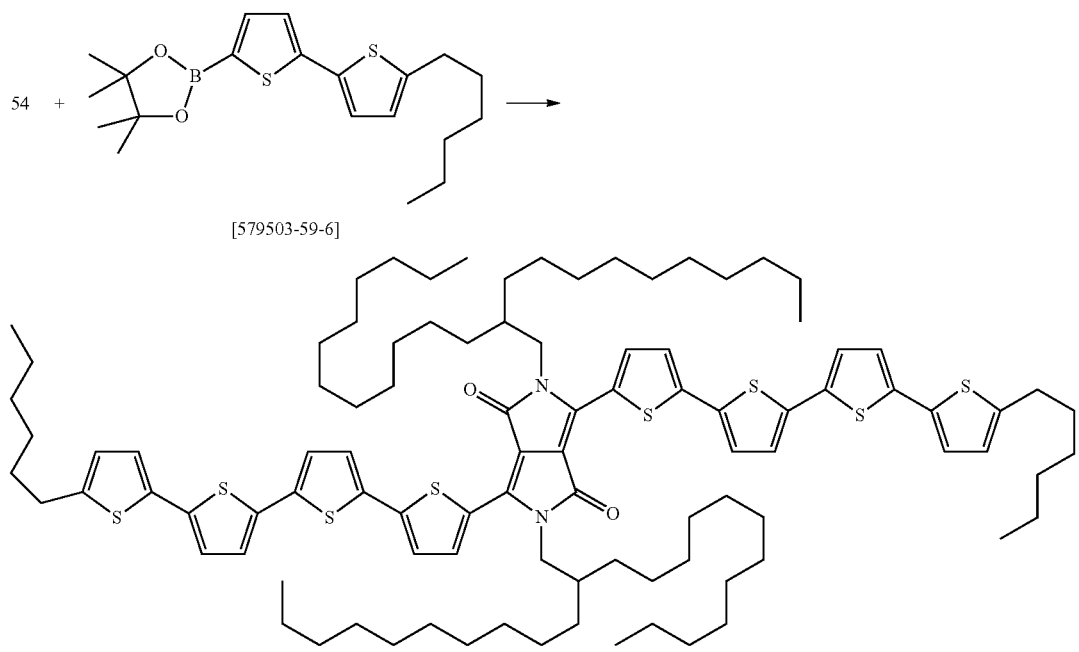

made by spin coating a layer of the PEDOT-PSS on a pre-patterned ITO on glass substrate. Then a 1:1 mixture by weight of compound 16 (1% by weight in chloroform) and [60]PCBM (a substituted $C_{60}$ fullerene) (also 1% by weight in chloroform) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=2.2 mA/cm², FF=0.66 and $V_{oc}$=0.74 V for an estimated overall efficiency of 1.1%.

EXAMPLE 33

Manufacture of the Semiconducting Compound of the Formula 63

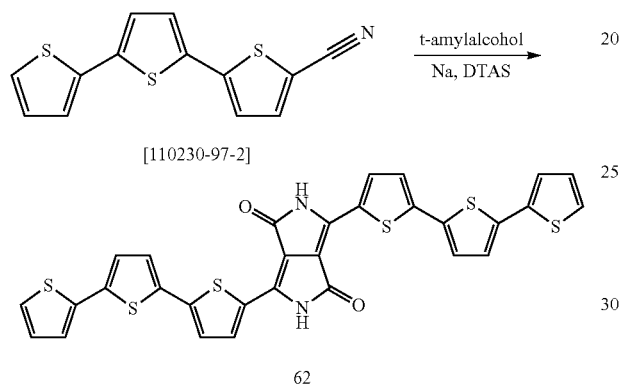

a) According to the procedure for the synthesis of compound 52, 5-Cyano-2,2':5',2''-Terthiophene [110230-97-2] is reacted to give insoluble compound 62: MS m/z: 628.

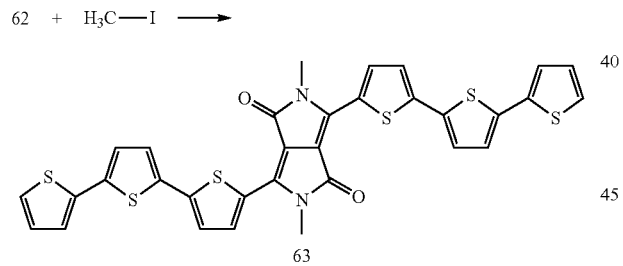

b) According to the procedure for the synthesis of 53, the DPP 62 is reacted with iodomethane [74-88-4] to give insoluble (i.e. insoluble in chloroform/toluene) compound 63. MS m/z: 656.

EXAMPLE 34

Manufacture of the Semiconducting Compound of the Formula 64

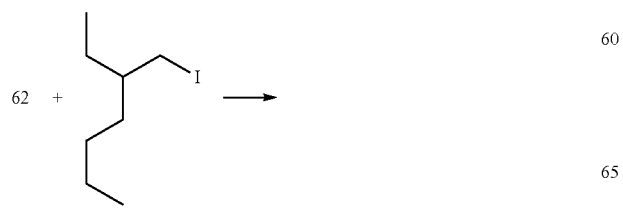

-continued

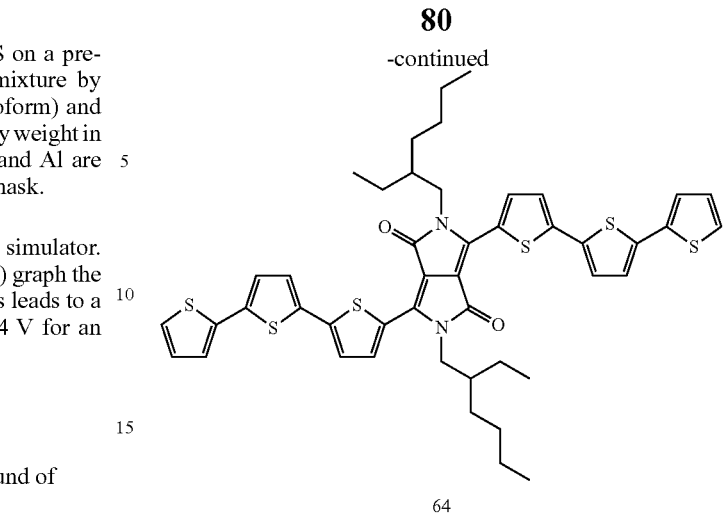

According to the procedure for the synthesis of 53, the DPP 62 is reacted with 2-ethyl-hexyl iodide [1653-16-3] to give compound 64. ¹H-NMR (ppm, CDCl₃): 8.94 2H d, 7.28-7.21 8H m, 7.12 2H d, 7.05 2H dd, 4.05 4H d, 1.94 2H m, 1.45-1.23 16H m, 0.93 6H t, 0.91 6H t.

EXAMPLE 35

Manufacture of the Semiconducting Compound of the Formula 67

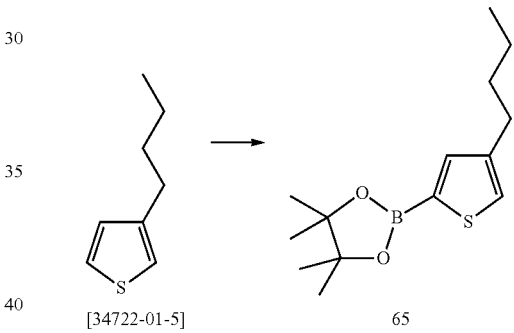

a) According to the procedure for the synthesis of compound 57, 3-butyl-thiophene [34722-01-5] and 2-isopropoxy-4,4,5,5-tetramethyl-1,3,2-dioxoborolane [61676-62-8] are reacted to give compound 65: ¹H-NMR (ppm, CDCl₃): 7.47 1H s, 7.21 1H s, 2.65 2H t, 1.63 2H quint, 1.38-1.31 2H m, 1.34 12H s, 0.91 3H t.

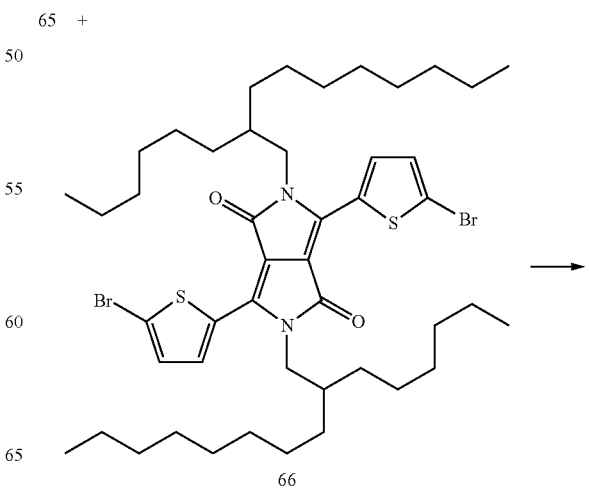

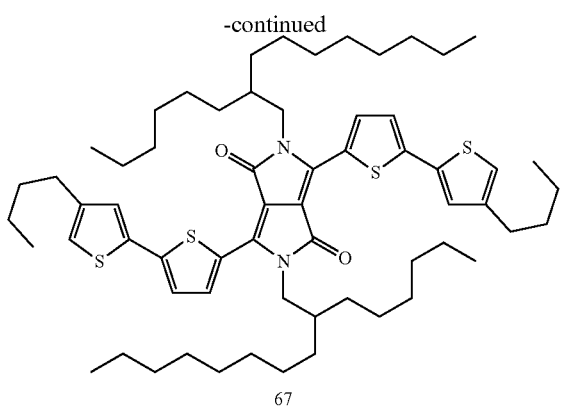

67 b) According to the procedure for the synthesis of compound 55, 4-butyl-2-thiophene-boronic acid pinacol ester 65 and the DPP derivative 66 (Example 2 of WO 2008/000664) are reacted to give compound 67: $^1$H-NMR (ppm, CDCl$_3$): 8.79 2H d, 7.19 2H d, 7.07 2H s, 6.84 2H s, 3.96 4H d, 2.54 4H t, 1.89 2H m, 1.61-1.14 56H m, 0.88 6H t, 0.77 6H t, 0.75 6H t.

EXAMPLE 36

Manufacture of the Semiconducting Compound of the Formula 68

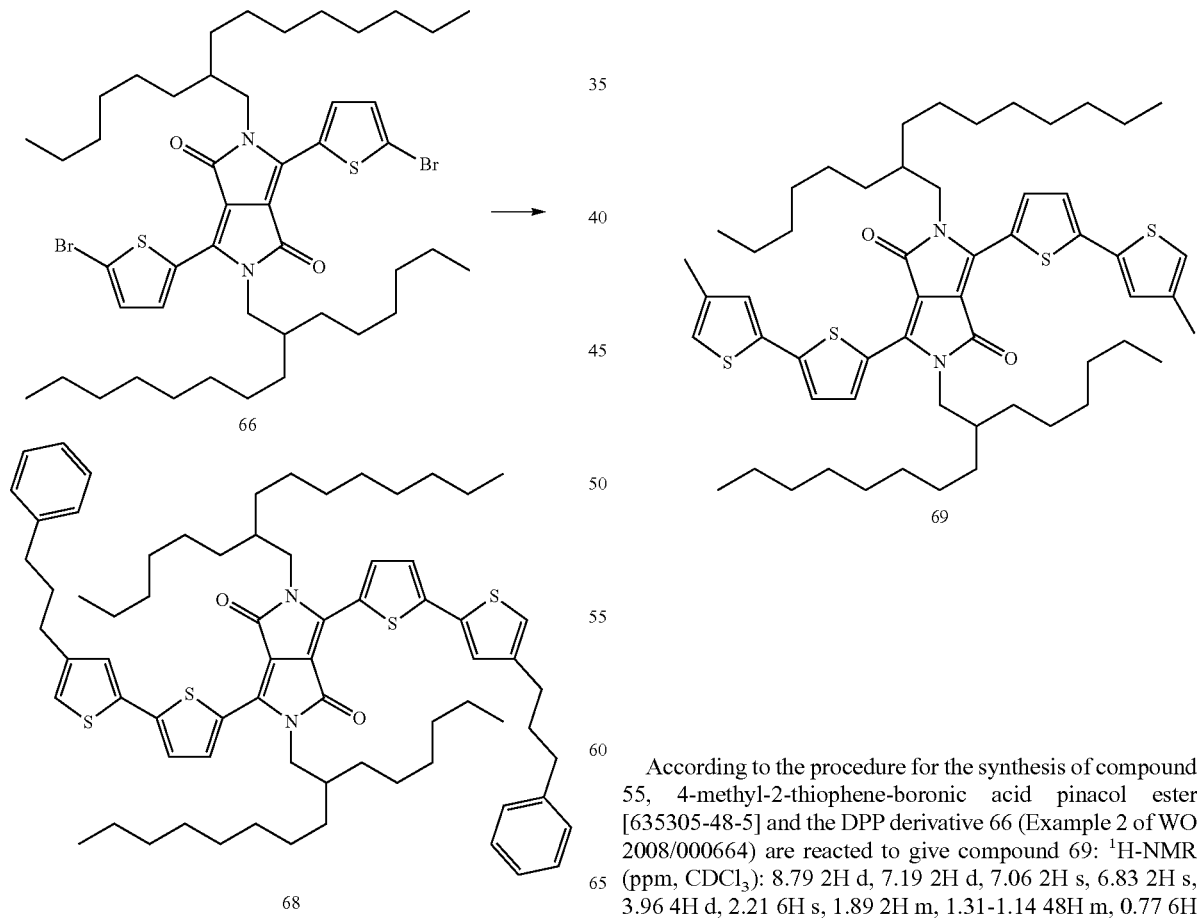

According to the procedure for the synthesis of compound 55, 4-(phenylpropyl)-2-thiophene-boronic acid pinacol ester 57 and the DPP derivative 66 (Example 2 of WO 2008/000664) are reacted to give compound 68: $^1$H-NMR (ppm, CDCl$_3$): 8.79 2H d, 7.25-7.09 12H m, 7.06 2H s, 6.84 2H s, 3.94 4H d, 2.63-2.54 8H m, 1.96-1.86 6H m, 1.29-1.13 48H m, 0.76 6H t, 0.74 6H t.

EXAMPLE 37

Manufacture of the Semiconducting Compound of the Formula 69

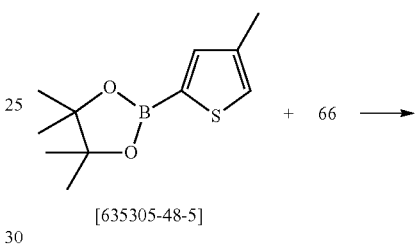

[635305-48-5]

According to the procedure for the synthesis of compound 55, 4-methyl-2-thiophene-boronic acid pinacol ester [635305-48-5] and the DPP derivative 66 (Example 2 of WO 2008/000664) are reacted to give compound 69: $^1$H-NMR (ppm, CDCl$_3$): 8.79 2H d, 7.19 2H d, 7.06 2H s, 6.83 2H s, 3.96 4H d, 2.21 6H s, 1.89 2H m, 1.31-1.14 48H m, 0.77 6H t, 0.75 6H t.

EXAMPLE 38

Manufacture of the Semiconducting Compound of the Formula 70

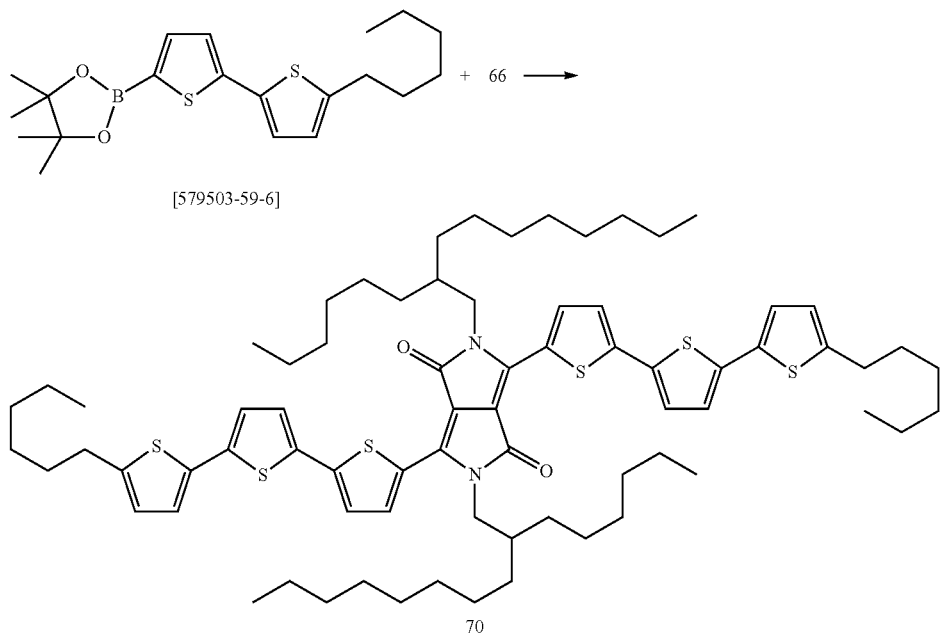

According to the procedure for the synthesis of compound 55, 5'-hexyl-2,2'-bithiophene-5-boronic acid pinacol ester [579503-59-6] and 66 are reacted to give compound 70: $^1$H-NMR (ppm, CDCl$_3$): 8.92 2H d, 7.28 2H d, 7.20 2H d, 7.04 4H dd, 6.71 2H d, 4.04 4H d, 2.81 4H t, 1.98 2H m, 1.67 4H m, 1.34-1.24 60H m, 0.92-0.82 18H m.

EXAMPLE 39

Application of the Semiconducting Compound of the Formula 70

The semiconductor thin film is prepared either by spin-coating or drop casting the DPP derivative of the formula 70 obtained in example 38 in a 0.5% (w/w) solution in chloroform. The spin coating is accomplished at a spinning speed of 3000 rpm (rounds per minute) for about 20 seconds in ambient conditions. The devices are evaluated as deposited.

Transistor Performance

The transistor behavior is measured on an automated transistor prober (TP-10, CSEM Zürich) and shows clear p-type transistor behavior. From a linear fit to the square root of the saturated transfer characteristics a field effect mobility of $8.7 \times 10^{-4}$ cm$^2$/Vs with an on/off current ratio of $2.9 \times 10^4$ is determined. The threshold voltage is about −5 V and −3 V.

EXAMPLE 40

Manufacture of the Semiconducting Compound of the Formula 74

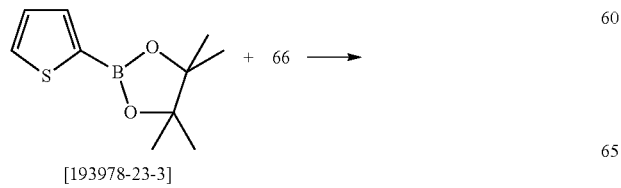

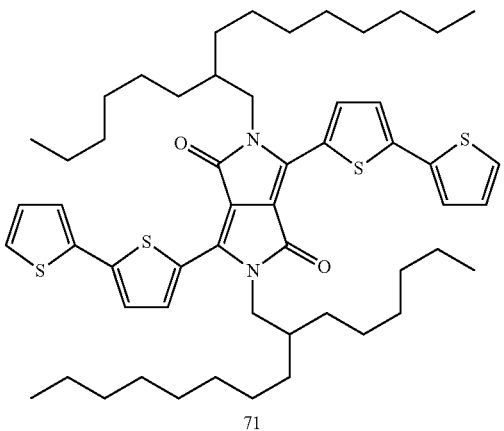

a) According to the procedure for the synthesis of compound 55, thiophene-2-boronic acid pinacol ester [193978-23-3] and 66 are reacted to give compound 71: $^1$H-NMR (ppm, CDCl$_3$): 8.90 2H d, 7.34-7.32 6H m, 7.08 2H dd, 4.04 4H d, 1.98 2H m, 1.35-1.20 48H m, 0.87-0.81 12H m.

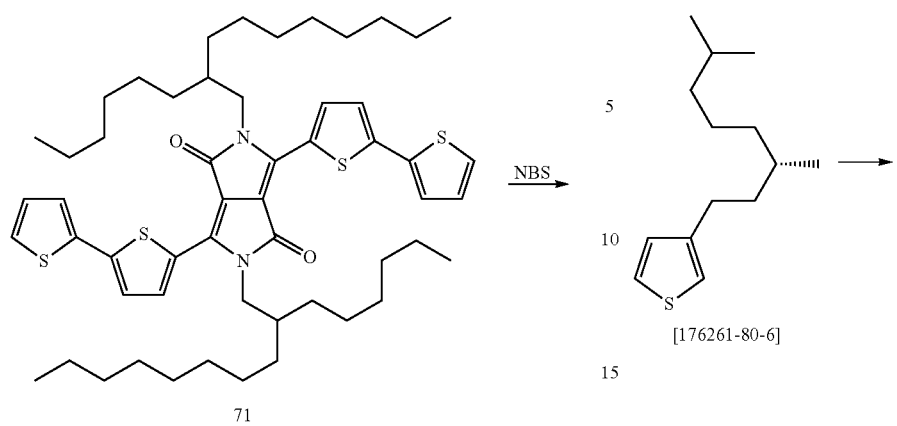

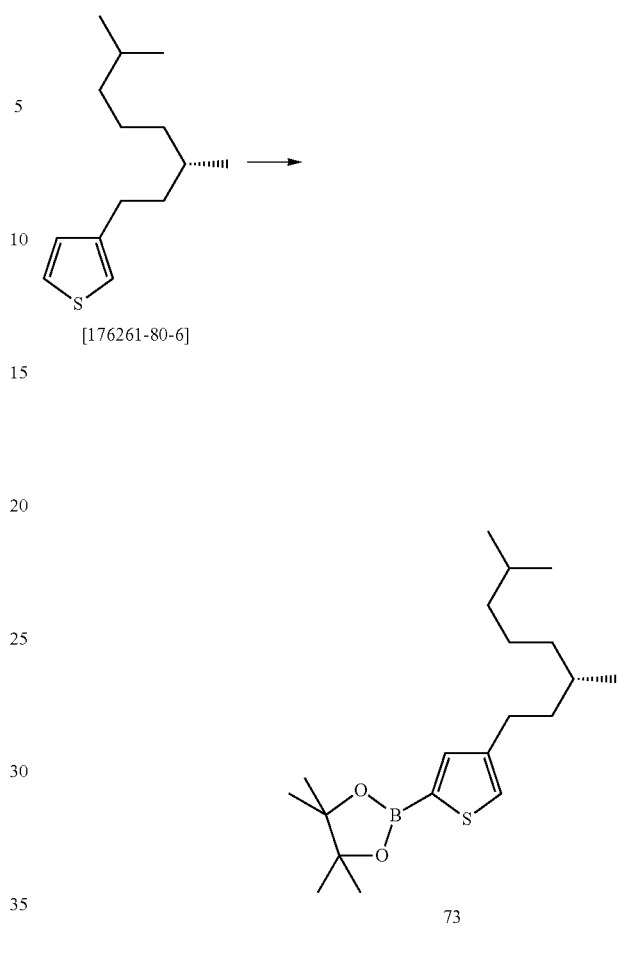

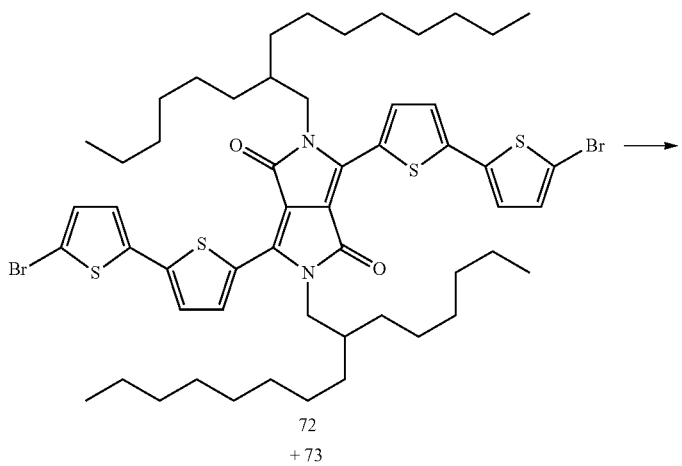

b) According to the procedure for the synthesis of compound 54, compound 71 and N-bromosuccinimide (NBS) are reacted to give compound 71: $^1$H-NMR data (ppm, CDCl$_3$): 8.86 2H d, 7.27 2H d, 7.04 4H dd, 4.01 4H d, 1.94 2H m, 1.32-1.21 48H m, 0.87-0.85 12H m.

c) According to the procedure for the synthesis of compound 57, (S)-3-(3,7-dimethyloctyl)-thiophene [176261-80-6] and 2-isopropoxy-4,4,5,5-tetramethyl-1,3,2-dioxoborolane [61676-62-8] are reacted to give compound 75: $^1$H-NMR (ppm, CDCl$_3$): 7.50 1H s, 7.23 1H s, 2.65 2H m; 1.70-1.10 68 10H m, 1.36 12H s, 0.93 3H d, 0.88 6H d.

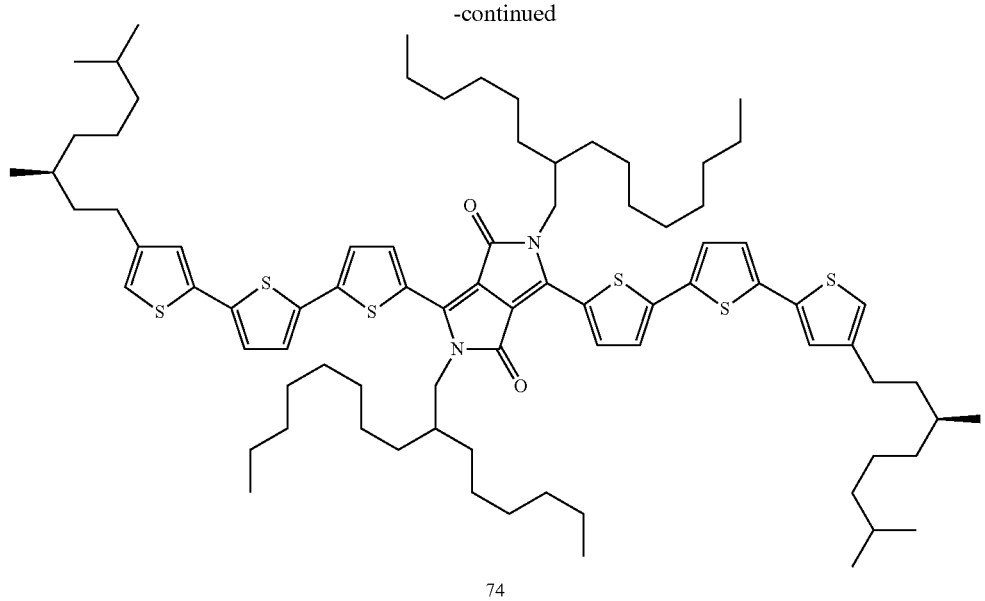

74 d) According to the procedure for the synthesis of compound 55, compounds 72 and 73 are reacted to give compound 74; m.p. 102.5° C.; $^1$H-NMR (ppm, CDCl$_3$): 8.92 2H d, 7.9 2H d, 7.21 2H d; 7.10 2H d, 7.06 2H s, 6.85 2H s, 4.05 4H d; 2.60 4H m; 1.98 2H m; 1.35-1.20 68H m 0.93 6H d, 0.89-0.81 24H m.

EXAMPLE 41
Application of the Semiconducting Compound of the Formula 74

The semiconductor thin film is prepared either by spin-coating or drop casting the DPP derivative of the formula 74 obtained in example 40 in a 0.5% (w/w) solution in chloroform. The spin coating is accomplished at a spinning speed of 3000 rpm (rounds per minute) for about 20 seconds in ambient conditions. The devices are evaluated as deposited.

Transistor Performance

The transistor behavior is measured on an automated transistor prober (TP-10, CSEM Zürich) and shows clear p-type transistor behavior. From a linear fit to the square root of the saturated transfer characteristics a field effect mobility of $1.3 \times 10^{-4}$ cm$^2$/Vs with an on/off current ratio of $9.1 \times 10^3$ is determined. The threshold voltage is about 1.7V.

EXAMPLE 42
Manufacture of the Semiconducting Compound of the Formula 76

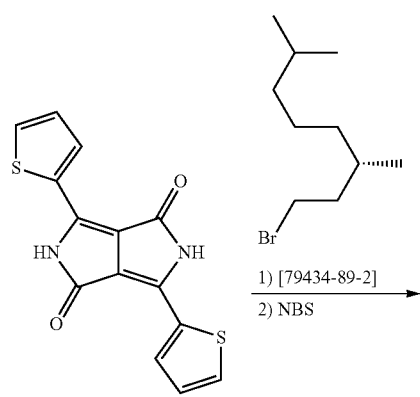

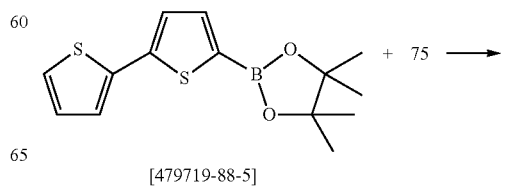

75 a) According to the procedure for the synthesis of compound 2, compound 1 and (S)-3-3,7-dimethyloctyl-bromide [79434-89-2] are reacted in DMF (instead of NMP) followed by the bromination with N-bromosuccinimide (NBS) yielding compound 75. $^1$H-NMR (ppm, CDCl$_3$): 8.65 2H d, 7.23 2H d, 4.02 4H m, 1.72-1.10 20H m, 1.00 6H d, 0.86 12H d.

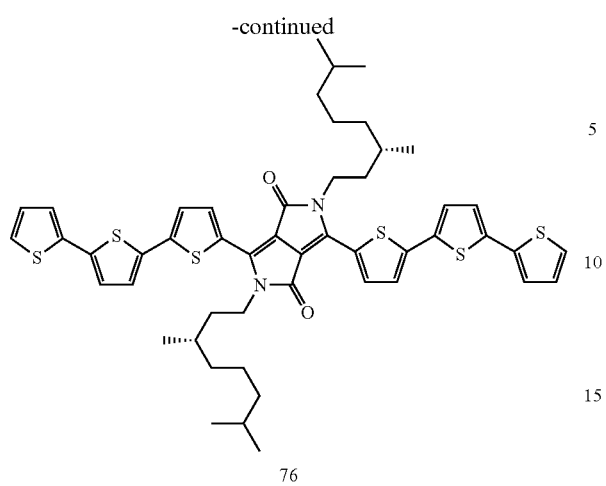

76 b) According to the procedure for the synthesis of compound 55, 2,2'-bithiophene-5-boronic acid pinacol ester [479719-88-5] and compound 75 are reacted to give compound 76; m.p. 239.8° C.; $^1$H-NMR (ppm, CDCl$_3$): 8.94 2H d, 7.31 2H d, 7.27 2H d, 7.23 4H dd, 7.13 2H d, 7.05 2H dd, 4.13 4H m, 1.75-1.10 20H m, 1.05 6H d, 0.85 12H d.

EXAMPLE 43

Application of the Semiconducting Compound of the Formula 76

The semiconductor thin film is prepared either by spin-coating or drop casting the DPP derivative of the formula 76 obtained in example 42 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and shows clear p-type transistor behavior. From a linear fit to the square root of the saturated transfer characteristics a field effect mobility of $6.5 \times 10^{-4}$ cm$^2$/Vs with an on/off current ratio of $4.1 \times 10^4$ is determined. The threshold voltage is about 1.6V.

EXAMPLE 44

Photovoltaic Application of the Semiconducting Compound of Formula 76

DPP-Monomer Based Bulk Heterojunction Solar Cell

The solar cell has the following structure: Al electrode/LiF layer/organic layer, including compound 76 and [60]PCBM/ [poly(3,4-ethylenedioxy-thiophene) (PEDOT)/poly(styrene-sulfonic acid) (PSS)]/ITO electrode/glass substrate. The solar cells are made by spin coating a layer of the PEDOT-PSS on a pre-patterned ITO on glass substrate. Then a 1:1 mixture of the compound of formula 76 (1% by weight): [60]PCBM (a substituted C$_{60}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=7.7 mA/cm$^2$, FF=0.34 and $V_{oc}$=0.70 V for an estimated overall efficiency of 1.8%.

EXAMPLE 45

Manufacture of the Semiconducting Compound of the Formula 77

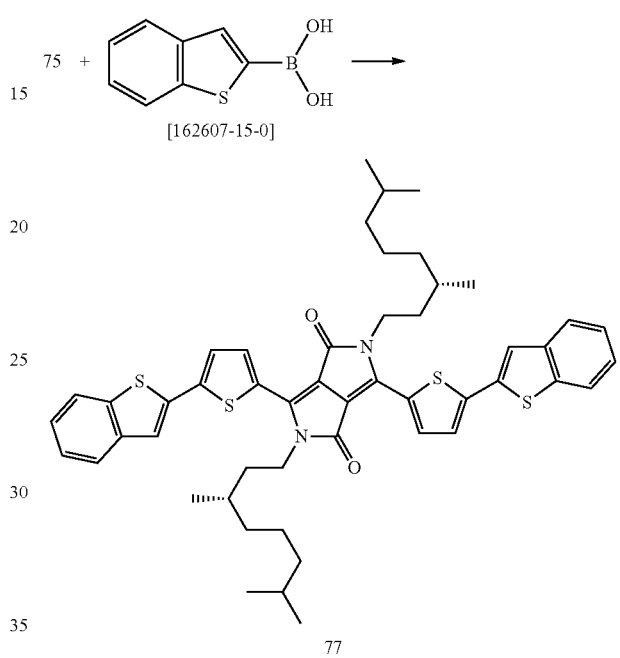

According to the procedure for the synthesis of compound 55, 1-benzothien-2-ylboronic acid [162607-15-0] and compound 75 are reacted to give compound 77; m.p. 275.0° C.; $^1$H-NMR (ppm, CDCl$_3$): 8.95 2H d, 7.31 2H d, 7.79 4H m, 7.55 2H s, 7.44 2H d, 7.37 4H m, 4.16 4H m, 1.85-1.10 20H m, 1.06 6H d, 0.85 12H d.

EXAMPLE 46

Application of the Semiconducting Compound of the Formula 77

The semiconductor thin film is prepared either by spin-coating or drop casting the DPP derivative of the formula 77 obtained in example 45 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and shows clear p-type transistor behavior. From a linear fit to the square root of the saturated transfer characteristics a field effect mobility of $1.8 \times 10^{-3}$ cm$^2$/Vs with an on/off current ratio of $2.7 \times 10^4$ is determined. The threshold voltage is about −4 V to 0 V.

EXAMPLE 47

Photovoltaic Application of the Semiconducting Compound of Formula 77

DPP-Monomer Based Bulk Heterojunction Solar Cell

The solar cell has the following structure: Al electrode/LiF layer/organic layer, including compound 77 and [60]PCBM/[poly(3,4-ethylenedioxy-thiophene) (PEDOT)/poly(styrenesulfonic acid) (PSS)]/ITO electrode/glass substrate. The solar cells are made by spin coating a layer of the PEDOT-PSS on a pre-patterned ITO on glass substrate. Then a 1:1 mixture of the compound of formula 77 (1% by weight): [60]PCBM (a substituted $C_{60}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=1.1 mA/cm$^2$, FF=0.30 and $V_{oc}$=0.25 V.

EXAMPLE 48

Manufacture of the Semiconducting Compound of the Formula 78

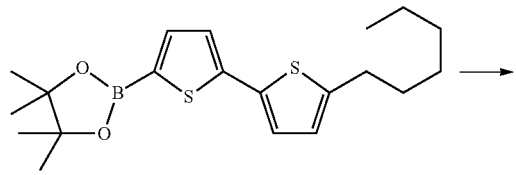

[579503-59-6]
+ 75

According to the procedure for the synthesis of compound 55, 5'-hexyl-2,2'-bithiophene-5-boronic acid pinacol ester [579503-59-6] and compound 75 are reacted to give compound 77: $^1$H-NMR (ppm, CDCl$_3$): 8.94 2H d, 7.27 2H d, 7.19 2H d, 7.02 4H dd, 6.70 2H d, 4.13 4H m, 2.80 4H t, 1.81-1.20 36 H m, 1.05 6H d, 0.91 6H t, 0.85 12H d.

EXAMPLE 49

Application of the Semiconducting Compound of the Formula 78

The semiconductor thin film is prepared either by spin-coating or drop casting the DPP derivative of the formula 78 obtained in example 48 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and shows clear p-type transistor behavior. From a linear fit to the square root of the saturated transfer characteristics a field effect mobility of 1.8×10$^{-3}$ cm$^2$/Vs with an on/off current ratio of 1.9×10$^4$ is determined. The threshold voltage is about −0.5 V.

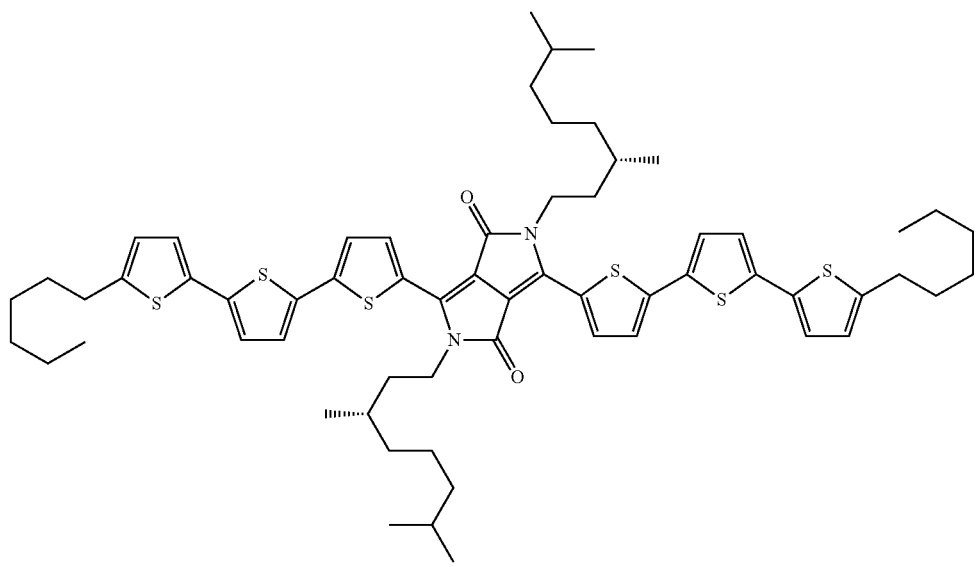

78

EXAMPLE 50

Manufacture of the Semiconducting Compound of the Formula 80

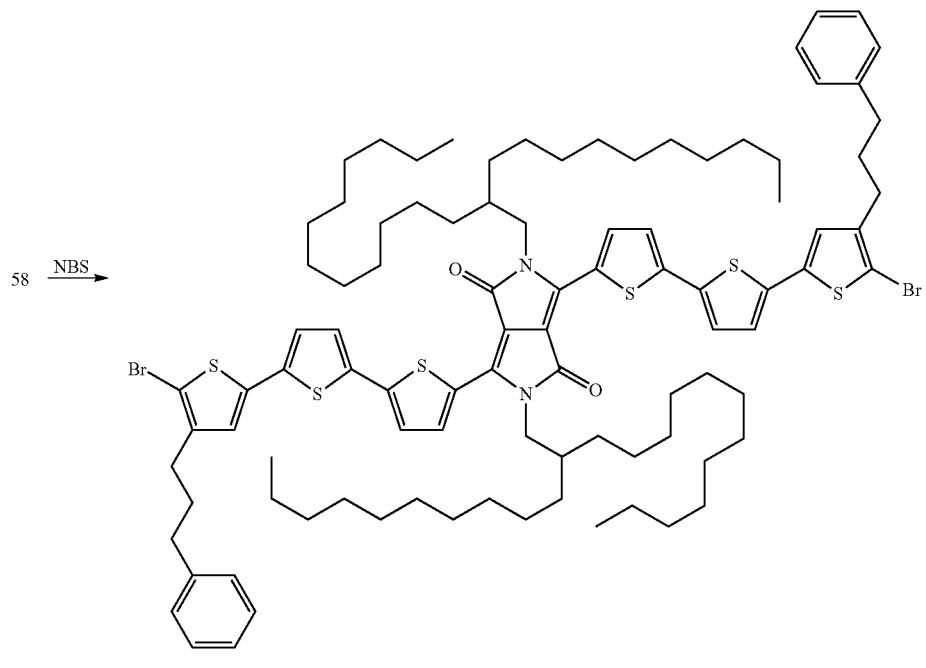

79 a) Analogous to the procedure for the synthesis of compound 54, compound 58 is dissolved in chloroform, cooled down to 0° C. and 2 equivalents of N-bromosuccinimide (NBS) are then added portion wise over a period of 1 h. After the reaction is completed, the mixture is washed with water. The organic phase is extracted, dried and concentrated. The compound is then purified over a silica gel column to give the compound of the formula 79; $^1$H-NMR (ppm, CDCl$_3$): 8.90 2H broad s, 7.33-7.15 14H m, 7.00 2H d, 6.87 2H s, 4.00 4H d, 2.69 4H dxd, 2.59 4H dxd, 2.00-1.90 6H m, 1.33-1.21 80H m, 0.87 6H t, 0.85 6H t.

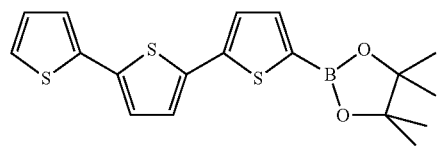

79 —[849062-17-5]→

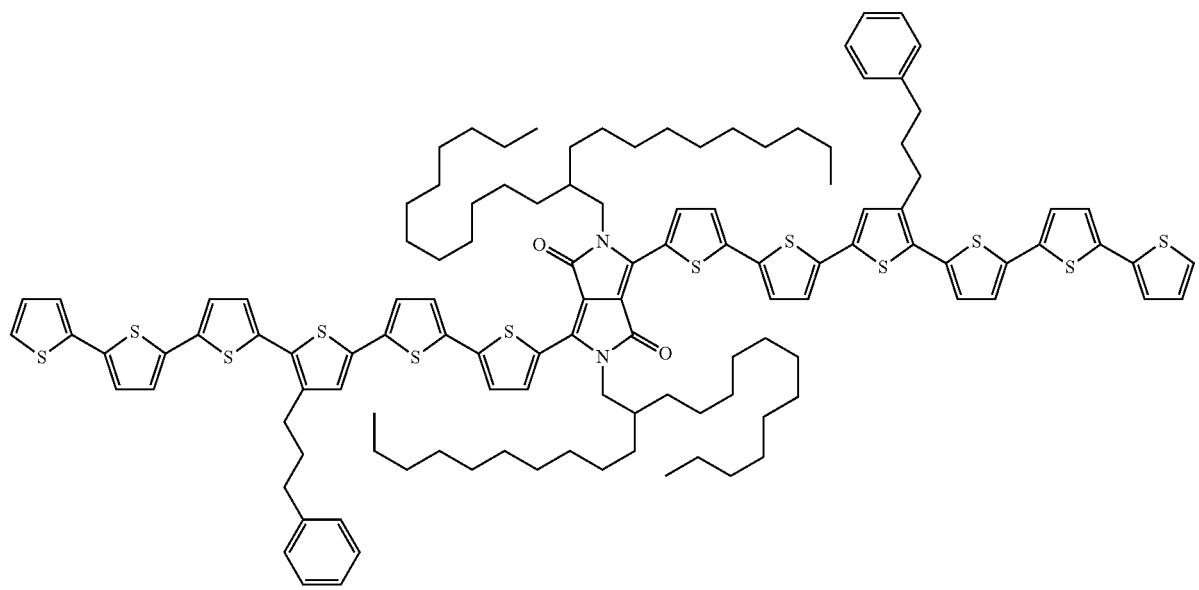

80

Analogous to the procedure for the synthesis of compound 55, 2,2':5',2''-terthiophene-5-boronic acid pinacol ester [849062-17-5] and compound 79 are reacted to give compound 80; 1H-NMR (ppm, CDCl$_3$): 8.93 2H d, 7.33-6.89 32H m, 4.00 4H d, 2.78-2.71 8H m, 2.05-1.97 6H m, 1.34-1.18 80H m, 0.85 12H t.

Transistor Performance

The transistor behavior of compound 80 is measured on an automated transistor prober (TP-10, CSEM Zürich) and shows clear p-type transistor behavior. From a linear fit to the square root of the saturated transfer characteristics a field effect mobility of $1.3 \times 10^{-2}$ cm$^2$/Vs with an on/off current ratio of $1 \times 10^5$ can be determined. The threshold voltage is about 10 V.

EXAMPLE 51

Manufacture of the Semiconducting Compounds of the Formulae 81 to 85

Using the methods described herein before the following compounds are obtained:

EXAMPLE 51a

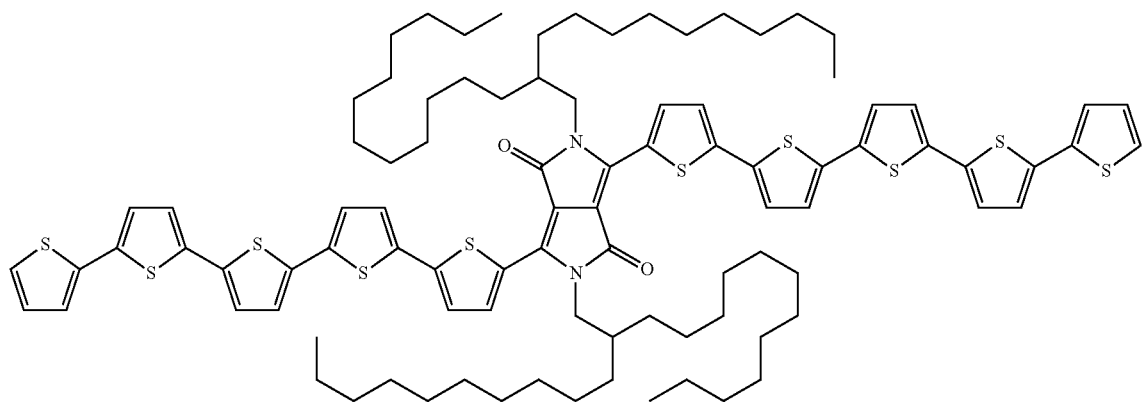

81

EXAMPLE 51b
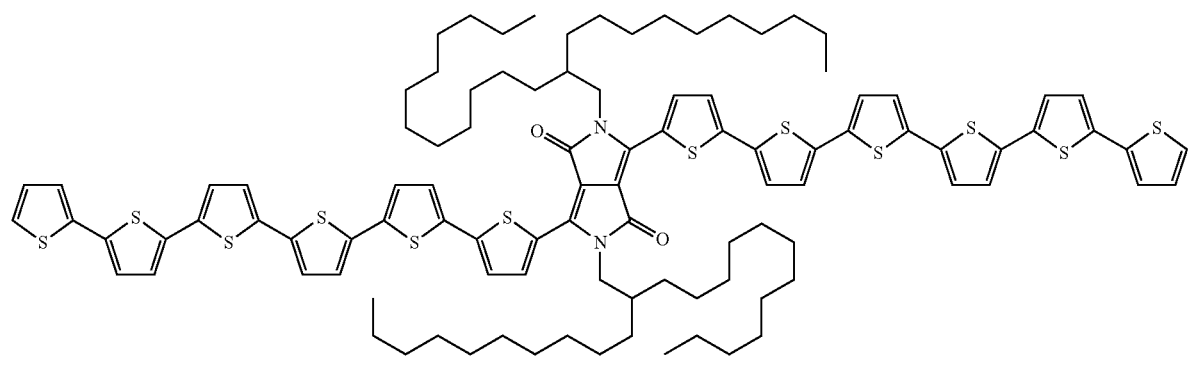
EXAMPLE 51c
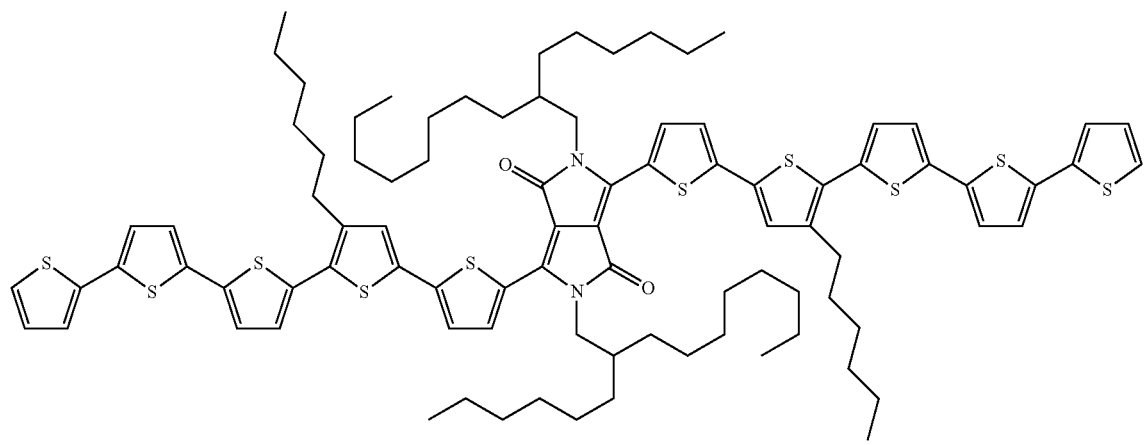
EXAMPLE 51d
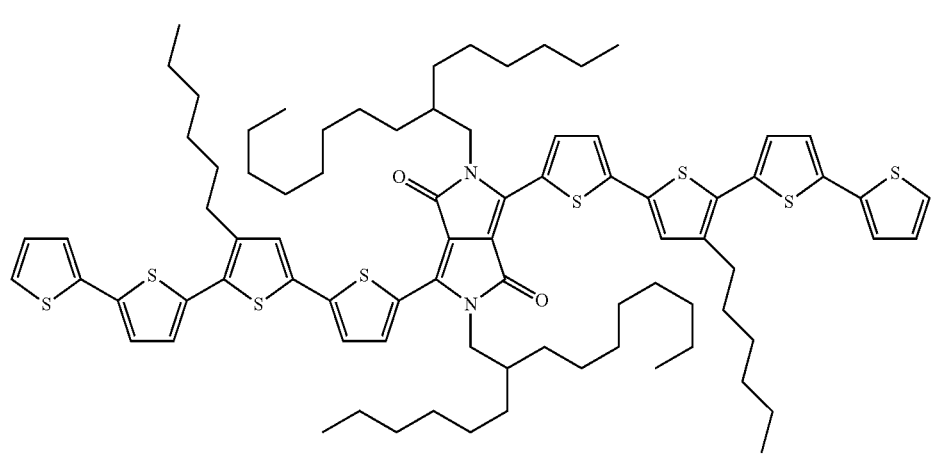

EXAMPLE 51e
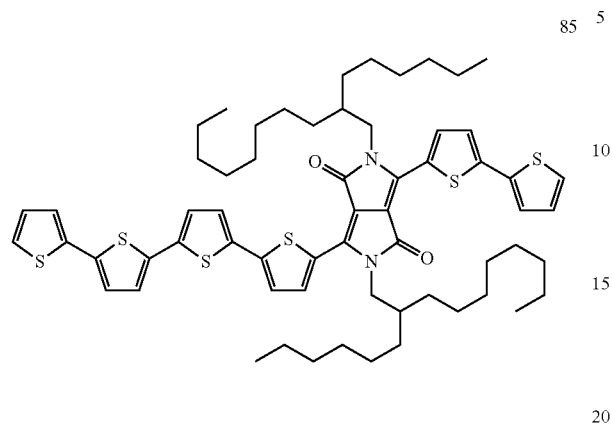
85
EXAMPLE 51f
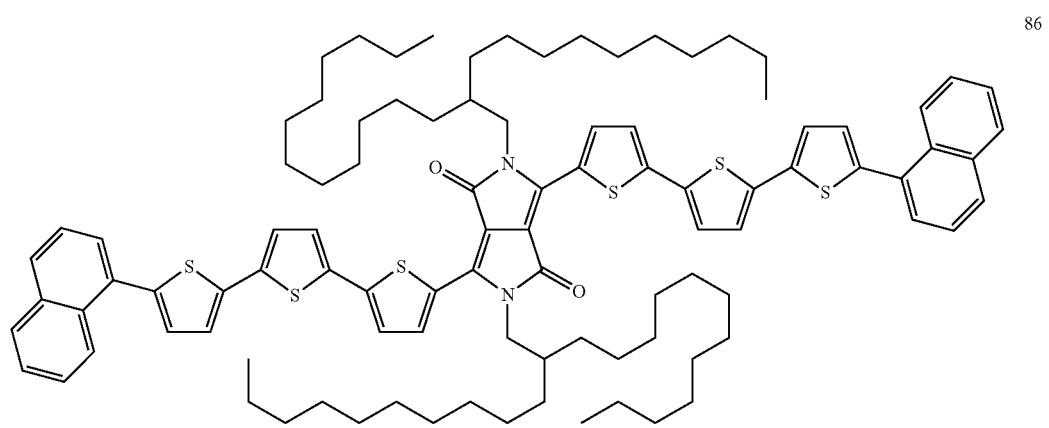 [SMILES: CCCCCCCCCCCCC(CCCCCCCCCC)CN1C(=O)C2=C(c3ccc(-c4ccc(-c5ccc(-c6cccc7ccccc67)s5)s4)s3)N(CC(CCCCCCCCCC)CCCCCCCCCCCC)C(=O)C2=C1c1ccc(-c2ccc(-c3ccc(-c4cccc5ccccc45)s3)s2)s1]
86
EXAMPLE 51g
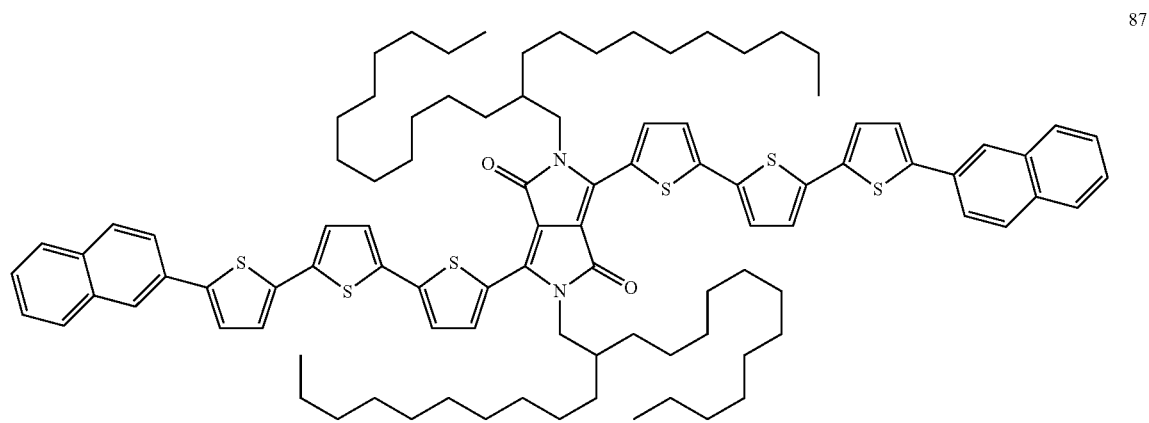 [SMILES: CCCCCCCCCCCCC(CCCCCCCCCC)CN1C(=O)C2=C(c3ccc(-c4ccc(-c5ccc(-c6ccc7ccccc7c6)s5)s4)s3)N(CC(CCCCCCCCCC)CCCCCCCCCCCC)C(=O)C2=C1c1ccc(-c2ccc(-c3ccc(-c4ccc5ccccc5c4)s3)s2)s1]
87

EXAMPLE 51h

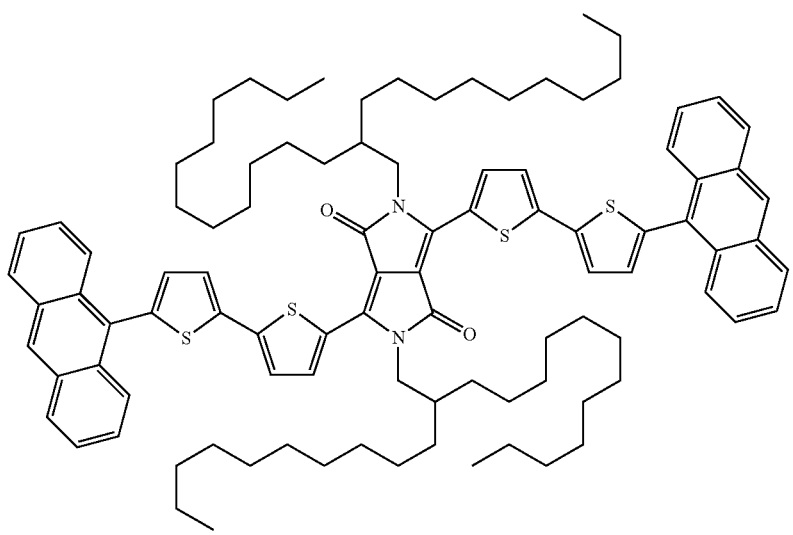

EXAMPLE 51i

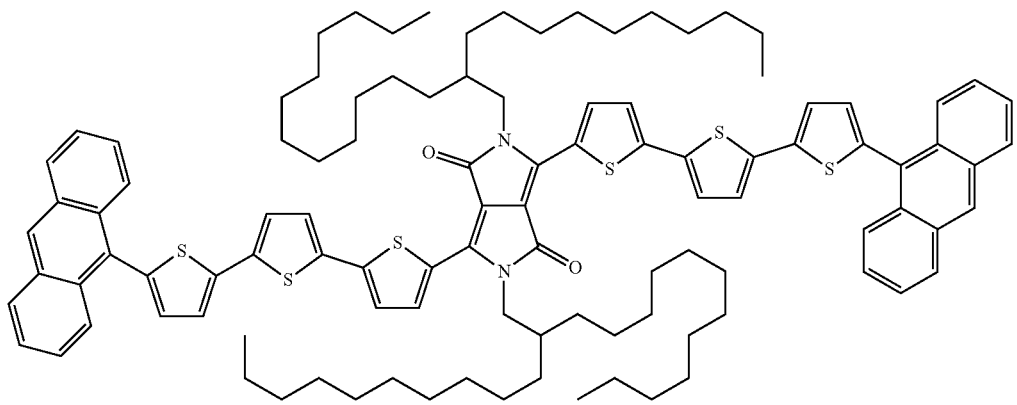

The invention claimed is:

1. A compound of the formula I

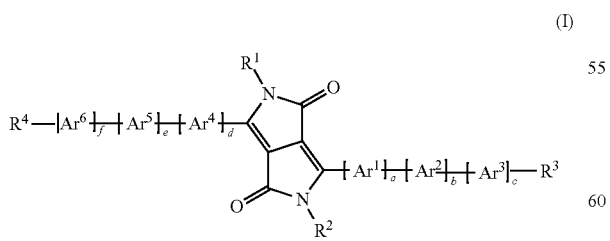

wherein $R^1$ and $R^2$ are independently of each other an aliphatic, cycloaliphatic, cycloaliphatic-aliphatic, aromatic, aromatic-aliphatic, heteroaromatic or heteroaromatic-aliphatic group having up to 49 carbon atoms, a and d independently of each other are 0, 1, 2 or 3, $Ar^1$ and $Ar^4$ are independently of each other a bivalent group of the formula II or IV

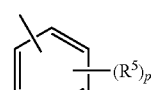

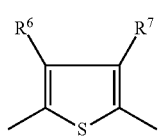

wherein
R⁶ and R⁷ are as defined below,
p represents 0, 1, or 2,
R⁵ is an aliphatic hydrocarbon group having up to 25 carbon atoms, or two vicinal groups R⁵ together represent alkylene or alkenylene having up to 7 carbon atoms, it being possible that two groups R⁵ present in the group of formula II differ from each other,
b, c, e, and f independently of each other represent 1, 2 or 3,
Ar², Ar³, Ar⁵, and Ar⁶ are independently of each other a bivalent group of one of the formulae IV to X and L,

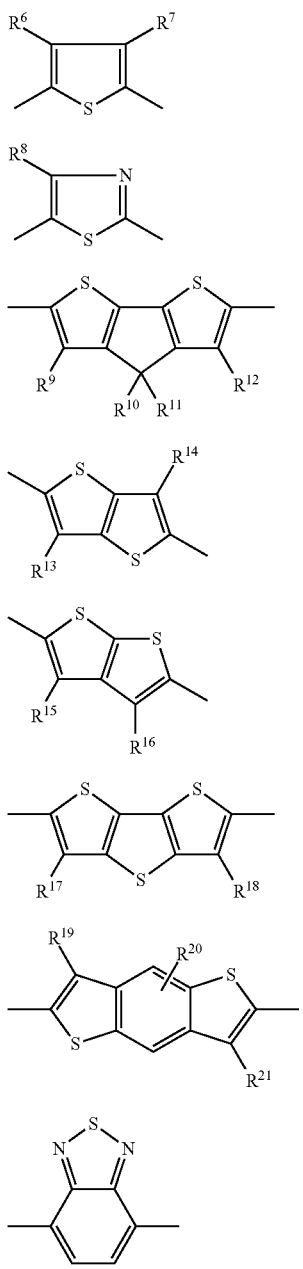

wherein $R^6, R^7, R^8, R^9, R^{12}, R^{13}, R^{15}, R^{16}, R^{17}, R^{18}, R^{19}, R^{20}$ and $R^{21}$ are independently of each other hydrogen, $C_1$-$C_{25}$alkyl, $C_1$-$C_{15}$alkoxy, $C_6$-$C_{24}$aryl, $C_7$-$C_{25}$aralkyl, or heteroaryl, or R⁶ and R⁷ together represent alkylene or alkenylene which may be both bonded via oxygen and/or sulfur to the thienyl residue and which may both have up to 25 carbon atoms, $R^{10}$ and $R^{11}$ are independently of each other hydrogen, $C_1$-$C_{15}$alkyl, $C_6$-$C_{24}$aryl, heteroaryl, or $R^{10}$ and $R^{11}$ together represent oxo or form a five or six membered ring, which is unsubstituted or substituted by a) an aliphatic hydrocarbon group having up to 18 carbon atoms, b) $C_1$-$C_{18}$alkoxy or $C_2$-$C_{18}$alkylenedioxy in both of which carbon atoms which are not adjacent to oxygen may be replaced by oxygen, or c) $C_6$-$C_{24}$aryl, $C_7$-$C_{25}$aralkyl, heteroaryl, $C_3$-$C_{12}$cycloalkyl or $C_4$-$C_{12}$cycloalkyl-alkyl, and R³ and R⁴ are independently of each other a group of one of formulae XI, XV, XVI, XVII, XVIII, and XIX,

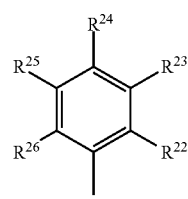

(XI)

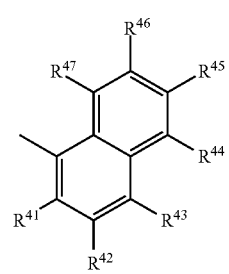

(XV)

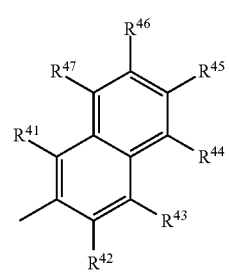

(XVI)

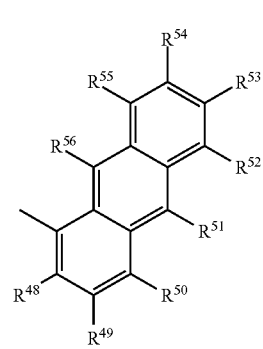

(XVII)

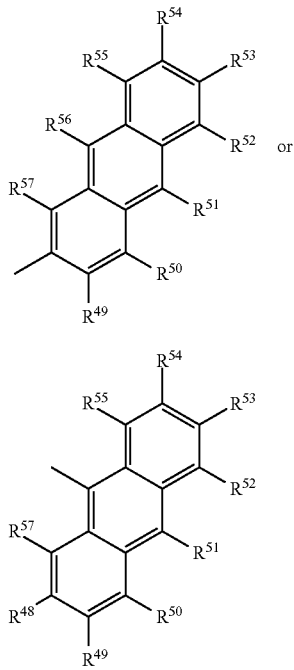

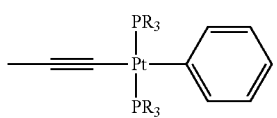

wherein $R^{22}$ to $R^{26}$ and $R^{41}$ to $R^{57}$ represent independently of each other hydrogen, an aliphatic hydrocarbon group having up to 25 carbon atoms, alkoxy or alkenyloxy having up to 18 carbon atoms, halogen, a cycloaliphatic, cycloaliphatic-aliphatic, aromatic, aromatic-aliphatic, heteroaromatic or heteroaromatic-aliphatic group having up to 25 carbon atoms, or a group of the formula (III)

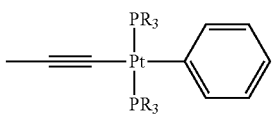

wherein $R_3$ represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{15}$alkoxy, $C_6$-$C_{24}$aryl, $C_7$-$C_{25}$aralkyl, heteroaryl, or a group of the formula (III) shown above, wherein $R_3$ represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms.

2. A compound of the formula I according to claim 1 wherein
$R^1$ and $R^2$ are independently of each other an aliphatic, cycloaliphatic, cycloaliphatic-aliphatic, aromatic, aromatic-aliphatic, heteroaromatic or heteroaromatic-aliphatic group having up to 25 carbon atoms,
wherein $R^{22}$ to $R^{26}$ and $R^{41}$ to $R^{57}$ represent independently of each other hydrogen, an aliphatic hydrocarbon group having up to 25 carbon atoms, or a group of the formula (III)

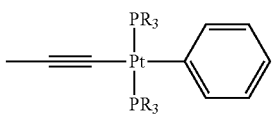

wherein $R_3$ represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein $R_3$ represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms,
and the remaining substituents are as defined in claim 1.

3. A compound of the formula I according to claim 1 wherein $R^1$ and $R^2$ are independently of each other an aliphatic, cycloaliphatic or cycloaliphatic-aliphatic hydrocarbon group having up to 25 carbon atoms,
a and d represent 0,
b, c, e, and f represent 1,
$Ar^2$, $Ar^3$, $Ar^5$, and $Ar^6$ are independently of each other a bivalent group of the formula IV,

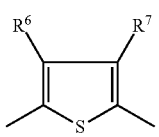

wherein $R^6$ and $R^7$ are independently of each other hydrogen or $C_1$-$C_{25}$alkyl.

4. A compound of the formula I according to claim 1 wherein $R^1$ and $R^2$ are independently of each other an aliphatic, cycloaliphatic or cycloaliphatic-aliphatic hydrocarbon group having up to 25 carbon atoms,
a and d represent 0,
b, c, e, and f represent 1,
$Ar^2$ and $Ar^5$ are independently of each other a bivalent group of the formula IV,

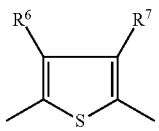

wherein one of $R^6$ and $R^7$ represents $C_1$-$C_{25}$alkyl while the other of $R^6$ and $R^7$ represents hydrogen or $C_1$-$C_{25}$alkyl,
$Ar^3$ and $Ar^6$ are a bivalent group of the formula IV, wherein each of $R^6$ and $R^7$ represents hydrogen.

5. A compound of the formula I according to claim 1 wherein
$R^1$ and $R^2$ are independently of each other an alkyl group having up to 49 carbon atoms,
a and d are independently of each other 0, 1 or 2, Ar$^1$ and Ar$^4$ are independently of each other a bivalent group of the formula IV

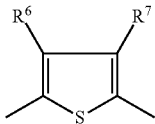
(IV)

wherein

R$^6$ and R$^7$ are independently of each other hydrogen or C$_1$-C$_{25}$alkyl, b, c, e, and f independently of each other represent 1, 2 or 3

Ar$^2$, Ar$^3$, Ar$^5$, and Ar$^6$ are independently of each other a bivalent group of the formula IV,

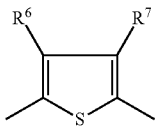
(IV)

wherein R$^6$ and R$^7$ are independently of each other hydrogen, C$_1$-C$_{25}$alkyl, or C$_7$-C$_{25}$aralkyl, and R$^3$ and R$^4$ are independently of each other a group of one of the formulae XI, XV, XVI, XVII, XVIII, and XIX

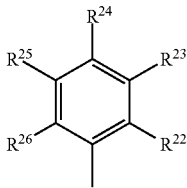
(XI)

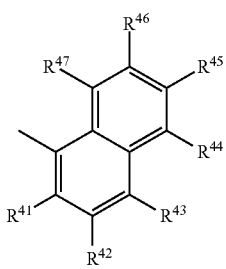
(XV)

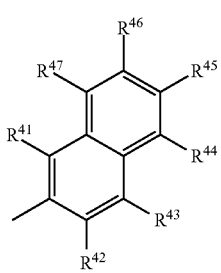
(XVI)

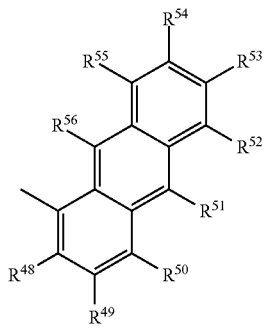
(XVII)

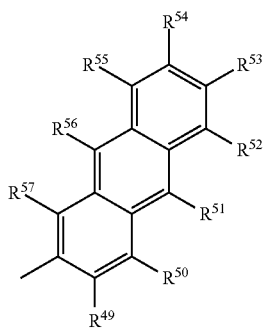
(XVIII)

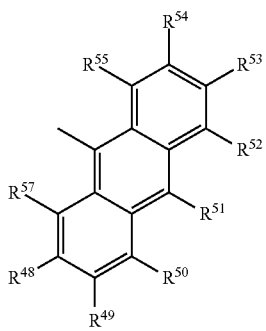
(XIX)

wherein R$^{22}$ to R$^{26}$, R$^{41}$ to R$^{55}$, R$^{57}$ and R$^{58}$ represent independently of each other hydrogen, an aliphatic hydrocarbon group having up to 25 carbon atoms, aryl, alkoxy having up to 18 carbon atoms, or halogen, or two groups R$^{22}$ to R$^{26}$ which are in the neighborhood of each other, together represent alkylene or alkenylene having up to 8 carbon atoms, thereby forming a ring.

6. A compound of the formula I according to claim 1 wherein R$^1$ and R$^2$ have the same meaning and the side chains of the formulae XLV and XLVI are identical to each other

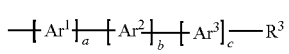
(XLV)

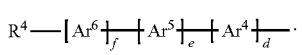
(XLVI)

7. A compound of the formula I according to claim 1 selected from the compounds having the following formulae
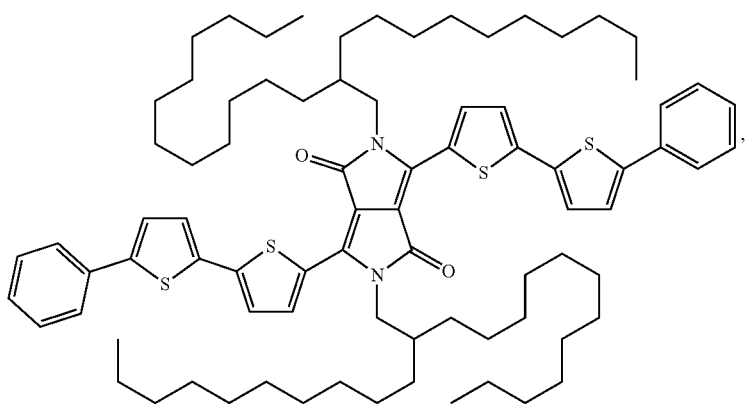
59,
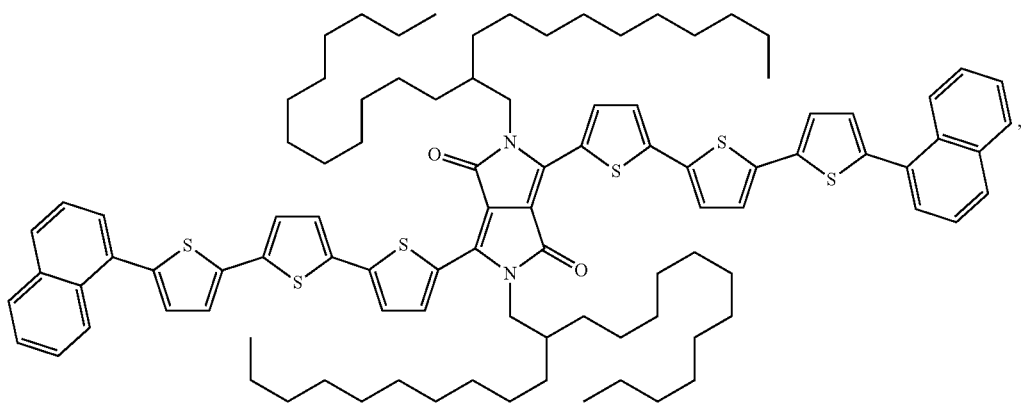
86,
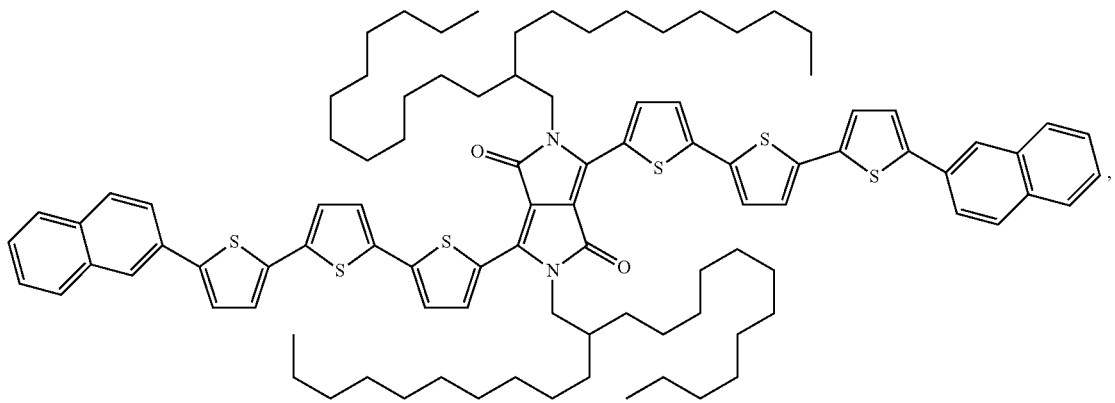
87, -continued
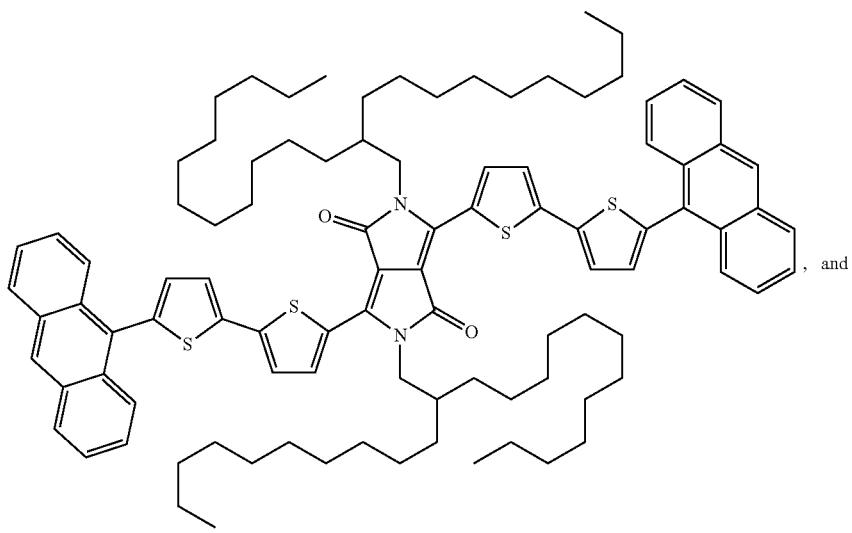, and
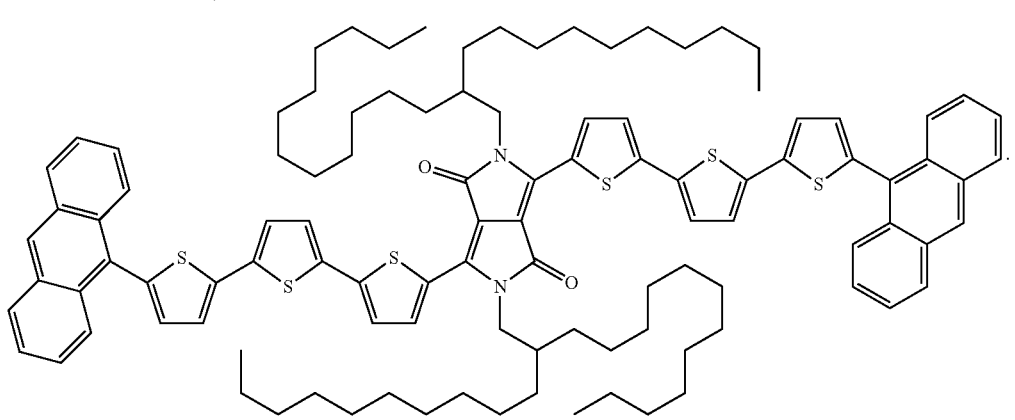.
* * * * *